US009517248B2

(12) United States Patent
Meiron et al.

(10) Patent No.: US 9,517,248 B2
(45) Date of Patent: *Dec. 13, 2016

(54) ADHERENT CELLS FROM ADIPOSE OR PLACENTA TISSUES AND USE THEREOF IN THERAPY

(71) Applicant: Pluristem Ltd., Haifa (IL)

(72) Inventors: Moran Meiron, Zikhron-Yaakov (IL); Amir Toren, Zikhron-Yaakov (IL); Rachel Ofir, Mitzpe Adi (IL); Zami Aberman, Tel-Mond (IL); Nirit Drori-Carmi, Doar-Na Hof HaCarmel (IL)

(73) Assignee: Pluristem Ltd., Haifa (IL)

( * ) Notice: Subject to any disclaimer, the term of this patent is extended or adjusted under 35 U.S.C. 154(b) by 144 days.

This patent is subject to a terminal disclaimer.

(21) Appl. No.: 14/180,039

(22) Filed: Feb. 13, 2014

(65) Prior Publication Data
US 2014/0242039 A1 Aug. 28, 2014

Related U.S. Application Data

(63) Continuation of application No. 13/958,706, filed on Aug. 5, 2013, which is a continuation of application No. 12/678,756, filed as application No. PCT/IL2008/001185 on Sep. 2, 2008, now Pat. No. 8,529,888.

(60) Provisional application No. 60/960,184, filed on Sep. 19, 2007.

(51) Int. Cl.
| *A01N 63/00* | (2006.01) |
| *A61K 35/50* | (2015.01) |
| *A61K 35/28* | (2015.01) |
| *A61K 35/36* | (2015.01) |
| *A61K 35/35* | (2015.01) |

(52) U.S. Cl.
CPC .............. *A61K 35/50* (2013.01); *A61K 35/28* (2013.01); *A61K 35/35* (2013.01); *A61K 35/36* (2013.01)

(58) Field of Classification Search
None
See application file for complete search history.

(56) References Cited

U.S. PATENT DOCUMENTS

| 4,846,835 | A | * | 7/1989 | Grande .......................... 128/898 |
| 5,108,989 | A | * | 4/1992 | Amento et al. ................. 514/8.9 |
| 5,474,687 | A | * | 12/1995 | Van Vlasselaer ............. 210/782 |
| 5,877,295 | A | * | 3/1999 | Diamond et al. ........ 530/388.73 |
| 5,962,325 | A | | 10/1999 | Naughton et al. |
| 6,911,201 | B1 | | 6/2005 | Merchav et al. |
| 7,045,148 | B2 | | 5/2006 | Hariri |
| 7,255,879 | B2 | | 8/2007 | Hariri |
| 7,311,904 | B2 | | 12/2007 | Hariri |
| 7,311,905 | B2 | | 12/2007 | Hariri |
| 7,468,276 | B2 | | 12/2008 | Hariri |
| 7,498,171 | B2 | | 3/2009 | Hariri et al. |
| 7,534,609 | B2 | | 5/2009 | Merchav et al. |
| 7,638,141 | B2 | | 12/2009 | Hariri |
| 7,678,573 | B2 | | 3/2010 | Merchav et al. |
| 8,524,496 | B2 | | 9/2013 | Meiron et al. |
| 8,529,888 | B2 | | 9/2013 | Meiron et al. |
| 9,096,827 | B2 | | 8/2015 | Meiron et al. |
| 2002/0076400 | A1 | | 6/2002 | Katz et al. |
| 2003/0032179 | A1 | | 2/2003 | Hariri et al. |
| 2003/0235563 | A1 | | 12/2003 | Strom et al. |
| 2004/0253241 | A1 | | 12/2004 | Cosgrove |
| 2005/0054098 | A1 | | 3/2005 | Mistry et al. |
| 2005/0118712 | A1 | | 6/2005 | Tsai et al. |
| 2005/0176143 | A1 | | 8/2005 | Merchav et al. |
| 2005/0181504 | A1 | | 8/2005 | Merchav et al. |
| 2005/0209231 | A1 | | 9/2005 | Wu et al. |
| 2005/0239897 | A1 | | 10/2005 | Pittenger et al. |
| 2005/0244421 | A1 | | 11/2005 | Strittmatter et al. |
| 2006/0030039 | A1 | | 2/2006 | Chen et al. |
| 2006/0083720 | A1 | | 4/2006 | Fraser et al. |
| 2007/0160588 | A1 | | 7/2007 | Kihm |
| 2007/0275362 | A1 | | 11/2007 | Edinger et al. |
| 2008/0075699 | A1 | * | 3/2008 | Buhring et al. ............. 424/93.7 |
| 2008/0138415 | A1 | | 6/2008 | Hussain et al. |
| 2009/0004738 | A1 | | 1/2009 | Merchav et al. |
| 2009/0324609 | A1 | * | 12/2009 | Lodie et al. ................ 424/158.1 |
| 2010/0209403 | A1 | | 8/2010 | Meiron et al. |

(Continued)

FOREIGN PATENT DOCUMENTS

| CN | 1649621 A | 8/2005 |
| CN | 1901802 A | 1/2007 |

(Continued)

OTHER PUBLICATIONS

Falanga V et al. 2007. Autologous Bone Marrow—Derived Cultured Mesenchymal Stem Cells Delivered in a Fibrin Spray Accelerate Healing in Murine and Human Cutaneous Wounds. Tissue Eng 13: 1299-1312.*
Miao Z et al. 2006. Isolation of mesenchymal stem cells from human placenta: Comparison with human bone marrow mesenchymal stem cells. Cell Biol Int'l 30: 681-687.*
Bain BJ et al. 2003. A-Z of Hematology. Blackwell Publishing (Malden, MA). p. 123.*
European Patent Office, Notice of Opposition to European Patent No. EP2200622, May 8, 2013.
Crystal Research Associates. "Pluristem Life Systems, Inc.—Executive Informational Overview," Apr. 20, 2007.

(Continued)

*Primary Examiner* — Lora E Barnhart Driscoll
(74) *Attorney, Agent, or Firm* — Wolf, Greenfield & Sacks, P.C.

(57) ABSTRACT

A method of treating ischemia in a subject in need thereof is disclosed. The method comprising administering to the subject a therapeutically effective amount of adherent cells of a tissue selected from the group consisting of a placenta and an adipose tissue, thereby treating the ischemia in the subject. A method of treating a medical condition requiring connective tissue regeneration and/or repair is also disclosed.

24 Claims, 27 Drawing Sheets

(56) References Cited

U.S. PATENT DOCUMENTS

| | | | |
|---|---|---|---|
| 2011/0129447 | A1 | 6/2011 | Meretzki et al. |
| 2011/0129486 | A1 | 6/2011 | Meiron |
| 2011/0171182 | A1 | 7/2011 | Abelman |
| 2011/0256108 | A1 | 10/2011 | Meiron et al. |
| 2011/0256159 | A1 | 10/2011 | Meiron et al. |
| 2011/0256160 | A1 | 10/2011 | Meiron et al. |
| 2011/0293583 | A1 | 12/2011 | Aberman |
| 2012/0122220 | A1 | 5/2012 | Merchav et al. |
| 2013/0004465 | A1 | 1/2013 | Aberman |
| 2013/0039892 | A1 | 2/2013 | Aberman |
| 2013/0259843 | A1 | 10/2013 | Duda et al. |
| 2013/0323213 | A1 | 12/2013 | Meiron et al. |
| 2013/0337558 | A1 | 12/2013 | Meiron et al. |
| 2014/0017209 | A1 | 1/2014 | Aberman et al. |
| 2014/0030805 | A1 | 1/2014 | Kasuto et al. |
| 2015/0125138 | A1 | 5/2015 | Karnieli et al. |
| 2015/0216907 | A1 | 8/2015 | Chajut et al. |
| 2015/0232797 | A1 | 8/2015 | Kasuto et al. |

FOREIGN PATENT DOCUMENTS

| | | |
|---|---|---|
| EP | 1845154 | 10/2007 |
| EP | 1878789 A1 | 1/2008 |
| JP | 2007-504204 A | 3/2007 |
| JP | 2007-505904 | 3/2007 |
| JP | 4554940 B2 | 9/2010 |
| WO | WO 01/82991 A2 | 11/2001 |
| WO | WO 02/064755 | 8/2002 |
| WO | WO 03/068937 A2 | 8/2003 |
| WO | WO 03/105908 | 12/2003 |
| WO | WO 2005/001076 A2 | 1/2005 |
| WO | WO 2005/001079 A2 | 1/2005 |
| WO | WO 2005/001080 A2 | 1/2005 |
| WO | WO 2005/025584 A1 | 3/2005 |
| WO | WO 2005/034843 A2 | 4/2005 |
| WO | WO 2006/071802 A2 | 7/2006 |
| WO | WO 2006/112390 A1 | 10/2006 |
| WO | WO 2006/121532 A2 | 11/2006 |
| WO | WO 2006/138552 | 12/2006 |
| WO | WO 2007/047465 A1 | 4/2007 |
| WO | WO 2007/061750 | 5/2007 |
| WO | WO 2007/083093 A1 | 7/2007 |
| WO | WO 2007/091255 A2 | 8/2007 |
| WO | WO 2007/108003 | 9/2007 |
| WO | WO 2008/100498 | 8/2008 |
| WO | WO 2009/037690 | 3/2009 |
| WO | WO 2010/026573 A1 | 3/2010 |
| WO | WO 2010/026574 A2 | 3/2010 |
| WO | WO 2010/026575 A2 | 3/2010 |

OTHER PUBLICATIONS

Globenewswire News Releases, "Crystal research Associates, LLC Issues Executive Informational Overview on Pluristem Life Systems, Inc.," Apr. 23, 2007.
Pluristem Life Systems, Inc., "Pluristem's PLX Cells Show Promise in Treating Limb Ischemia," Jul. 23, 2007, http://www.pluristem.com/old press/23 07 2007.htm (last accessed May 8, 2013).
Pluristem Life Systems, Inc., "Form 10-KSB, Annual Report Pursuant to Section 13 or 15(d) of the Securities Exchange Act of 1934," Submission to the United States Securities and Exchange Commission, Sep. 5, 2007.
Ayoub, "Interview: Pluristem Life Systems VP Dr. Prather," Seeking Alpha, Sep. 16, 2007.
Scherberich et al., "Three-dimensional perfusion culture of human adipose tissue-derived endothelial and osteoblastic progenitors generates osteogenic constructs with intrinsic vascularization capacity," Stem Cells 25:1823-29 (Apr. 19, 2007).
Garcia-Olmo et al., "A Phase I Clinical Trial of the Treatment of Crohn's Fistula by Adipose Mesenchymal Stem Cell Transplantation," Disease of the Colon & Rectum, 48(7): 1416-23 (published online May 17, 2005).
Garcia-Olmo et al., "Autologous Stem Cell Transplantation for Treatment of Rectovaginal Fistula in Perianal Crohn's Disease: A New Cell-Based Therapy," Int. J. Colorectal Disorders, 18:451-54 (published online May 20, 2003).
United States National Institutes of Health, Clinicaltrials.gov. Clinical Trial No. NCT0042688, Jan. 24, 2007.
Vyas et al., "A Technique for Increasing Yields in Bioreactors and Disposable Cell-Culture Systems," Nature Methods Application Notes 2007, pp. an7-an8 (Jan. 7, 2007).
Japanese Patent Office, Notice of Reason for Rejection, Patent Application No. 2010-525491, Mar. 15, 2013.
International Preliminary Report on Patentability Dated Jan. 22, 2009 From the International Bureau of WIPO Re.: Application No. PCT/IL2007/000380.
Communication Relating to the Results of the Partial International Search Dated Feb. 3, 2010 From the European Patent Office Re.: Application No. PCT/IL2009/000846.
Communication Relating to the Results of the Partial International Search Dated Feb. 12, 2010 From the International Searching Authority Re.: Application No. PCT/IL2009/000845.
International Preliminary Report on Patentability Dated Apr. 1, 2010 From the Intenational Bureau of WIPO Re.: Application No. PCT/IL2008/001185.
International Search Report and the Written Opinion Dated Jan. 25, 2010 From the International Searching Authority Re.: Application No. PCT/IL2009/000844.
International Search Report Dated Aug. 12, 2008 From the International Searching Authority Re.: Application No. PCT/IL2007/000380.
International Search Report Dated Dec. 30, 2008 From the International Searching Authority Re.: Application No. PCT/IL2008/001185.
Search Report and the Written Opinion Dated Dec. 8, 2009 From the Intellectual Property Office of Singapore Re.: Application No. 200807095-5.
Written Opinion Dated Aug. 12, 2008 From the International Searching Authority Re.: Application No. PCT/IL2007/000380.
Written Opinion Dated Dec. 30, 2008 From the Intenational Searching Authority Re.: Application No. PCT/IL2008/001185.
Barlow et al. "Comparison of Human Placenta- and Bone Marrow-Derived Multipotent Mesenchymal Stem Cells", Stem Cells and DevelopmentXP002563129, 17(6): 1095-1107, Dec. 2008. p. 1096-1100, Fig. 4.
Brooke et al. "Therapeutic Applications of Mesenchymal Stromal Cells", Seminars in Cell & Developmental Biology, XP022372977, 18(6): 846-858, Dec. 1, 2007.
Fibbe et al. "Mesenchymal Stem Cells and Hematopoietic Stem Cell Transplantation", Annals of the New York Academy of Sciences, 996:235-244, 2003.
Horwitz et al. "Clarification of the Nomenclature for MSC: The International Society for Cellular Therapy Position Statement", Cytotherapy, 7(5): 393-395, 2005.
Iwase et al., "Comparison of Angiogenic Potency Between Mesenchymal Stem Cells and Mononuclear Cells in A Rat Model of Hindlimb Ischemia", Cardiovascular Research, 66: 543-551, 2005.
Le Blanc et al. "HLA Expression and Immunologic Properties of Differentiated and Undifferentiated Mesenchymal Stem Cells", Experimental Hematology, 31:890-896, 2003.
Li et al. "Mesenchymal Stem Cells Derived From Human Placenta Suppress Allogeneic Umbilical Cord Blood Lymphocyte Proliferation", Cell Research, XP009080356, 15(7): 539-547, Jul. 1, 2005. p. 514-542.
Minguell et al., "Mesenchymal Stem Cells", Minireview, Experimental and Biological Medicine, 226(6): 507-520, 2001.
Moon et al., "Human Adipose Tissue-Derived Mesenchymal Stem Cells Improve Postnatal Neovascularization in A Mouse Model of Hindlimb Ischemia", Cellular Physiology and Biochemistry, 17: 279-290, Mar. 2006.
Nakagami et al., "Adipose Tissue-Derived Stromal Cells as A Novel Option for Regenerative Cell Therapy", Journal of Atheroselerosis and Thrombosis, 13(2): 77-81, Dec. 2005.
Pluristem "Pluristem Demonstrates the Potential of Its PLX Cells to Treat Crohn's Disease and Ulcerative Colitis", Pluristem Home Page, Press Releases, XP002553068, p. 1-2, May 2008. Abstract.

(56) References Cited

OTHER PUBLICATIONS

Prather et al., "Placental-Derived and Expanded Mesenchymal Stromal Cells (PLX-I) to Enhance the Engraftment of Hematopoietic Stem Cells Derived From Umbilical Cord Blood", *Expert Opinion on Biological Therapy*, XP009128193, 8(8): 1241-1250, Aug. 2008.
Prather et al., "The Role of Placental-Derived Adherent Stromal Cell (PLX-PAD) in the Treatment of Critical Limb Ischemia", *Cytotherapy*, XP009127935, 11 ( 4 ): 427-434, Jan. 1, 2009.
Ramot et al., "Safety and Biodistribution Profile of Placental-Derived Mesenchymal Stromal Cells (PLX-PAD) Following Intramuscular Delivery", *Toxicologic Pathology*, XP009127728, 37(5): 606-616, Aug. 1, 2009.
Tyndall et al., "Multipotent Mesenchymal Stromal Cells for Autoimmune Diseases: Teaching New Dogs Old Tricks", *Bone Marrow Transplantation*, XP002553067, 43(11): 821-828, Jun. 1, 2009.
Ventura et al., "Hyaluronan Mixed Esters of Batyric and Retinoic Acid Drive Cardiac and Endothelial Fate in Term Placenta Human Mesenchymal Stem Cells and Enhance Cardiac Repair in Infarcted Rat Hearts", *The Journal of Biological Chemistry* 282(19): 14243-14252, May 2007.
Wulf et al., "Mesemgenic Progenitor Cells Derived From Human Placenta", *Tissue Engineering*, XP001206075, 10(7/8): 1136-1147, Jul. 1, 2004, Table 1.
Yen et al., "Isolation of Multipotent Cells From Human Term Placenta", *Stem Cells*, 23: 3-9, 2005.
Zhang et al., "Human Placenta-Derived Mesenchymal Progenitor Cells Support Culture Expansion of Long-Term Culture-Initiating Cells From Cord Blood CD34+ Cells", *Experimental Hematology*, 32: 657-664, 2004.
Zhag et al., "Perfusion Bioreactor System for Human Mesenchymal Stem Cell Tissue Engineering: Dynamic Cell Seeding and Construct Development", *Biotechnology and Bioengineering*, XP002457538, 91(4): 482-493, Aug. 1, 2005.
Zhou et al., "Therapeutic Neovascularization for Peripheral Arterial Diseases: Advances and Perspectives", *Histology and Histopathology*, XP009127650, 22(6): 677-686, Jun. 1, 2007. Abstract.
Zimmet et al., "Emerging Role for Bone Marrow Derived Mesenchymal Stem Cells in Myocardial Regenerative Therapy", *Basic Research in Cardiology*, 100(6): 471-481, 2005.
Reponse Dated May 4, 2010 to Search Report and the Written Opinion Dated Dec. 8, 2009 From the Intellectual Property Office of Singapore Issued by the Danish Patent and Trademark Office Re.: Application No. 200807095-5.
Maurice et al., "Isolation of progenitor cells from cord blood using adhesion matrices," *Cytotechnology*, 54:121-133, Jun. 30, 2007.
Horita et al., "Intravenous Administration of Glial Cell Line-Derived Neurotrophic Factor Gene-Modified Human Mesenchymal Stem Cells Protects Against Injury in a Cerebral Ischemia Model in the Adult Rat," *J. Neurosci, Res*, 84(7): 1495-1504, Nov. 15, 2006.
Ukai et al., "Mesenchymal Stem Cells Derived from Peripheral Blood Protects Against Ischemia," *J. Neurotrauma*, 24(3): 508-520, Mar. 2007.
Traktuev et al., "Adipose Stromal Cells—Plastic Type of Cells with High Therapeutic Potential," *Tshologiya*, 48(2): 83-94, Feb. 2006.
Mitchell et al., "Immunophenotype of Human Adipose-Derived Cells: Temporal Changes in Stromal-Associated and Stem Cell-Associated Markers," *Stem Cells*, 24(2): 376-85, Feb. 2006.
Dominici et al., "Minimal Criteria for Defining Multipotent Mesenchymal Stromal Cells. The International Society for Cellular Therapy Position Statement," *Cytotherapy*, 8(4): 315-17. Aug. 2006.
Igura et al., "Isolation and Characterization of Mesenchymal Progenitor Cells from Chorionic Villi of Human Placenta," *Cytotherapy*, 6(6): 543-53, Jun. 2004.
Kern et al., Comparative analysis of mesenchymal stem cells from bone marrow, umbilical cord blood, or adipose tissue. Stem Cells. May 2006;24(5):1294-301. Epub Jan. 12, 2006.
Meinel et al., Bone tissue engineering using human mesenchymal stem cells: effects of scaffold material and medium flow. Ann Biomed Eng. Jan. 2004;32(1):112-22.
Portmann-Lanz et al., Placental mesenchymal stem cells as potential autologous graft for pre-and perinatal neuroregeneration. Am J Obstet Gynecol. Mar. 2006;194(3):664-73.
Delorme et al., Specific plasma membrane protein phenotype of culture-amplified and native human bone marrow mesenchymal stem cells. Blood. Mar. 1, 2008;111(5):2631-5. Epub Dec. 17, 2007.
Im et al., Do adipose tissue-derived mesenchymal stem cells have the same osteogenic and chondrogenic potential as bone marrow-derived cells? Osteoarthritis Cartilage. Oct. 2005;13(10):845-53.
Koh et al. Implantation of human umbilical cord-derived mesenchymal stem cells as a neuroprotective therapy for ischemic stroke in rats,Brain Res. Sep. 10, 2008;1229:233-48. doi: 10.1016/j.brainres.2008.06.087. Epub Jul. 2, 2008.
Pittenger et al., Multilineage potential of adult human mesenchymal stem cells. Science. Apr. 2, 1999;284(5411):143-7.
Young et al., Use of mesenchymal stem cells in a collagen matrix for Achilles tendon repair. J Orthop Res. Jul. 1998;16(4):406-13.
Zhang et al., Comparison of mesenchymal stem cells from human placenta and bone marrow. Chin Med J (Engl). Jun. 2004;117(6):882-7.
Zhao et al., Effects of oxygen transport on 3-d human mesenchymal stem cell metabolic activity in perfusion and static cultures: experiments and mathematical model. Biotechnol Prog. Jul.-Aug. 2005;21(4): 1269-80.
Wu et al., Mesenchymal stem cells enhance wound healing through differentiation and angiogenesis. Stem Cells. Oct. 2007;25(10):2648-59. Epub Jul. 5, 2007.

\* cited by examiner

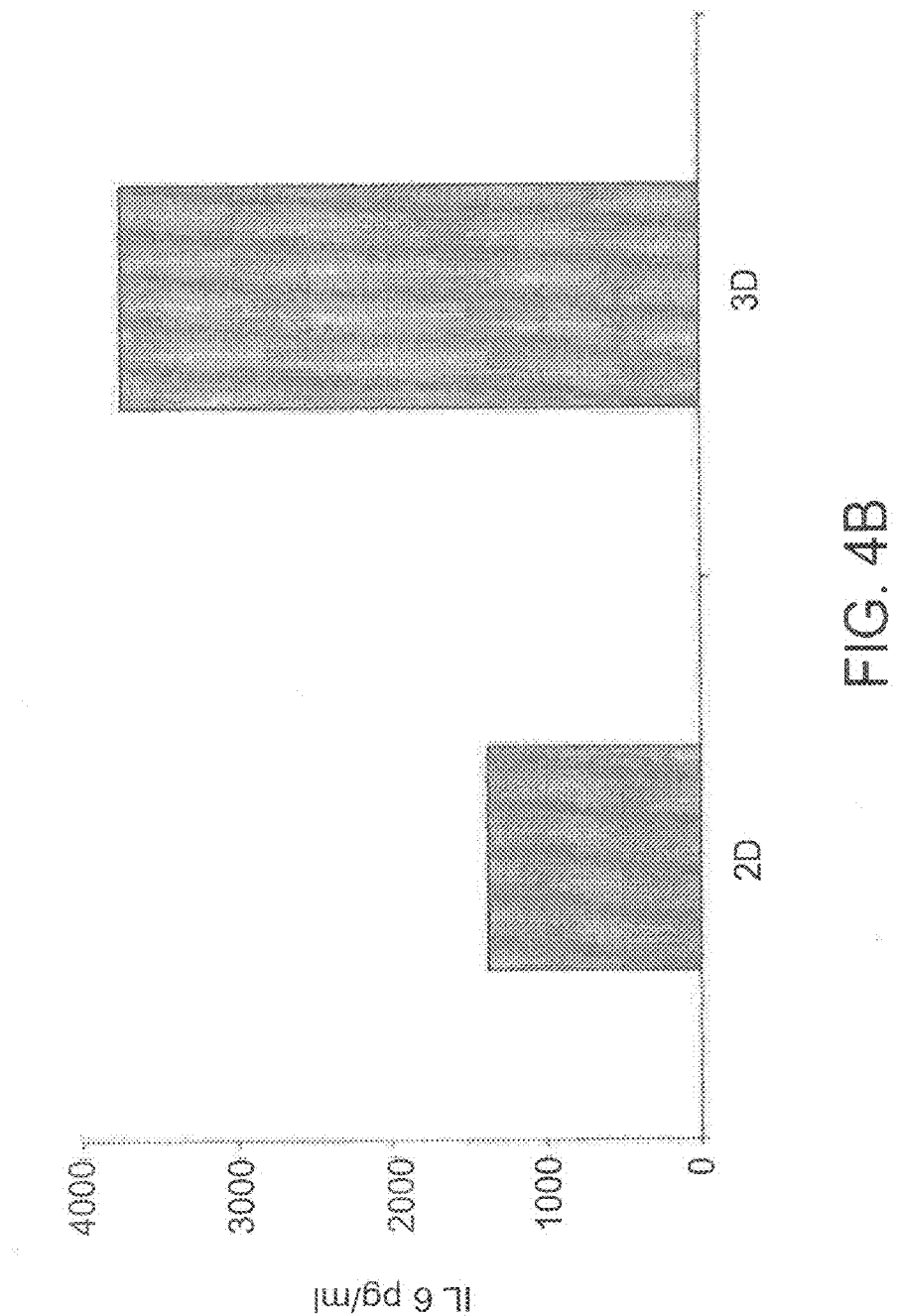

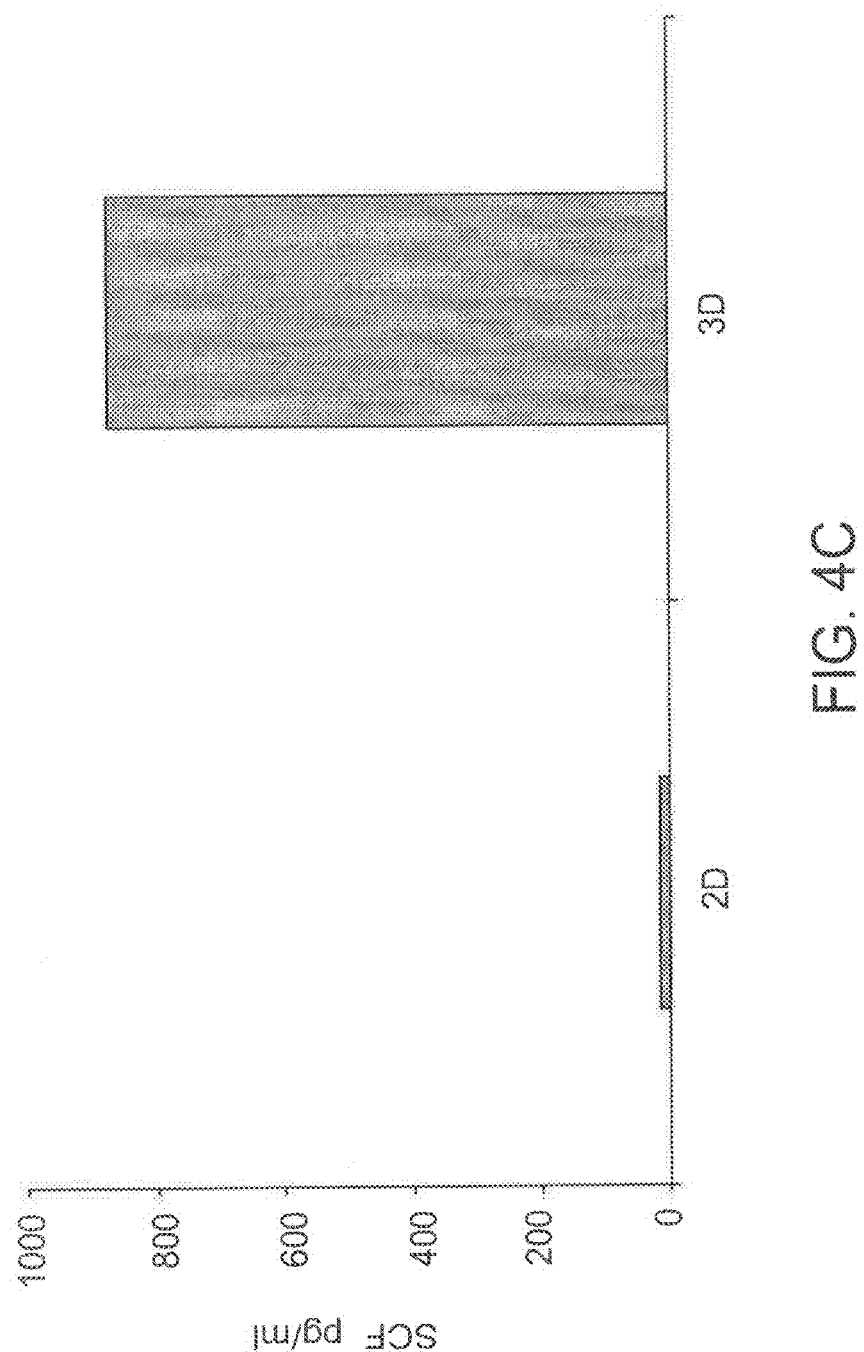

Human CD45+ (%)
Mouse CD45+ (%)

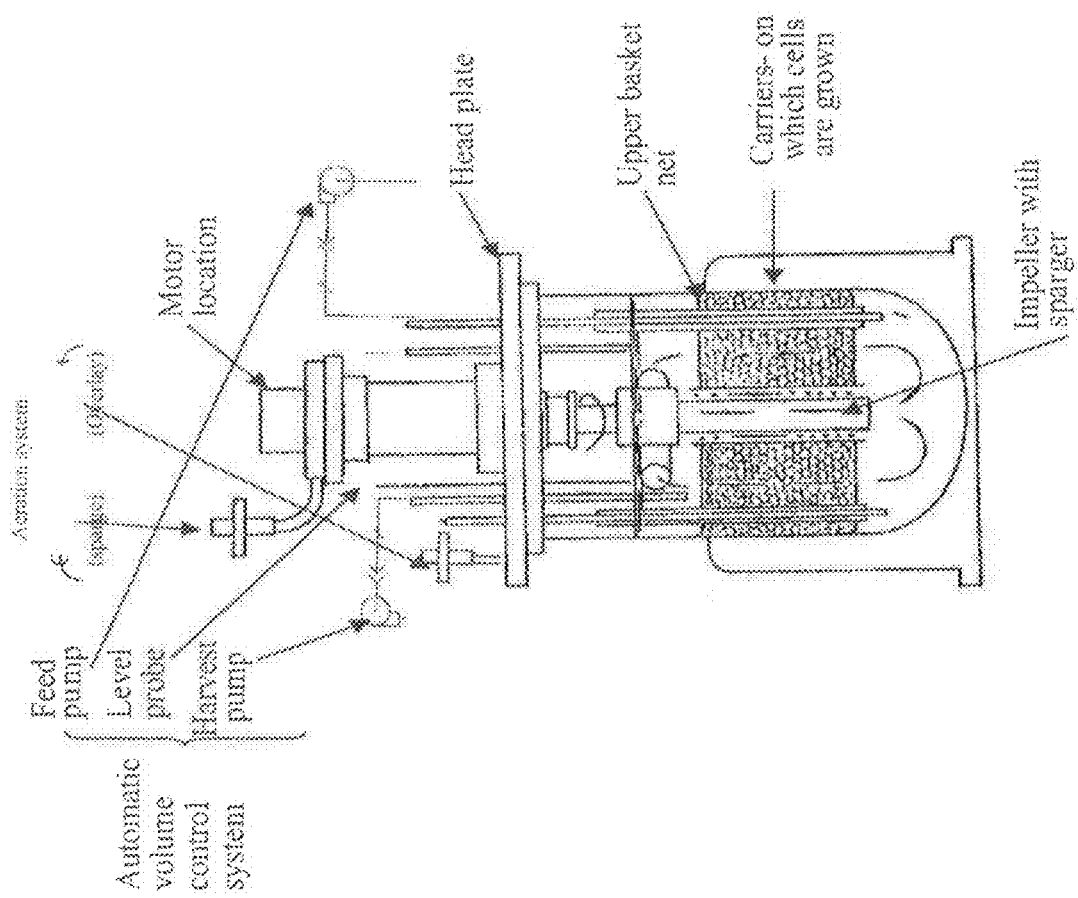

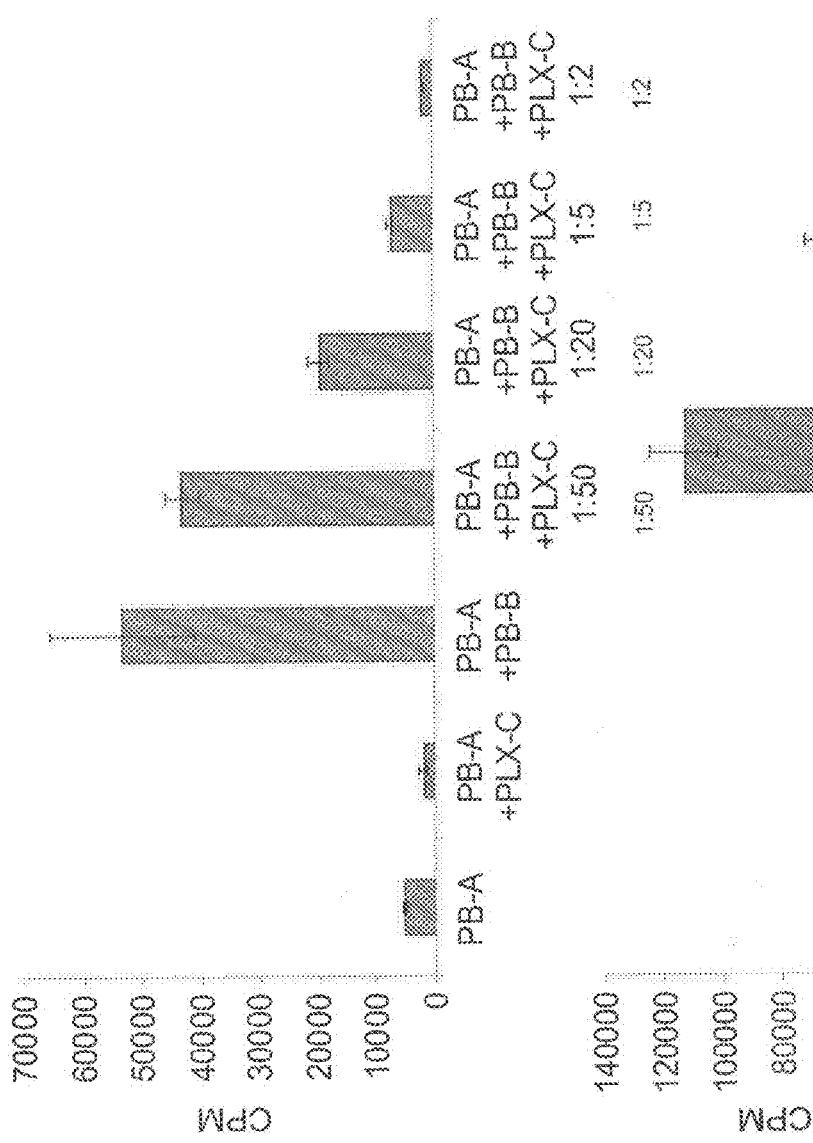

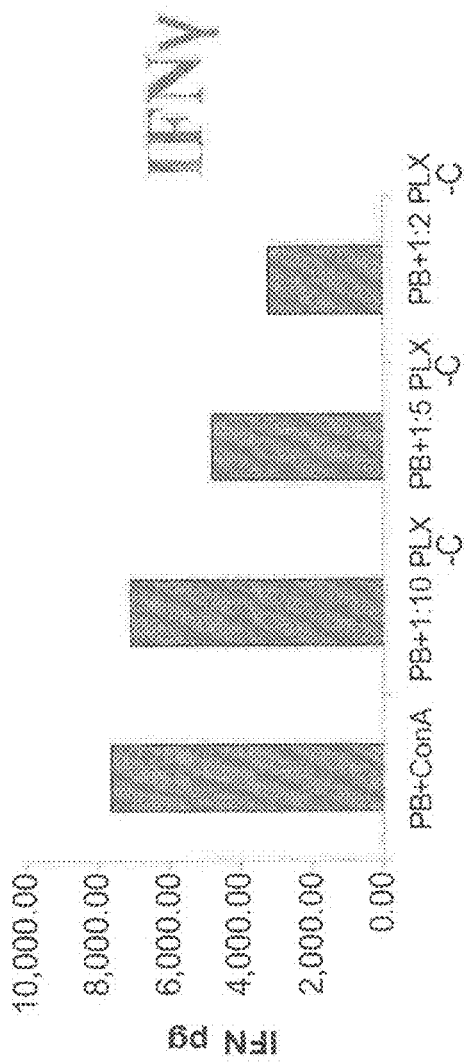
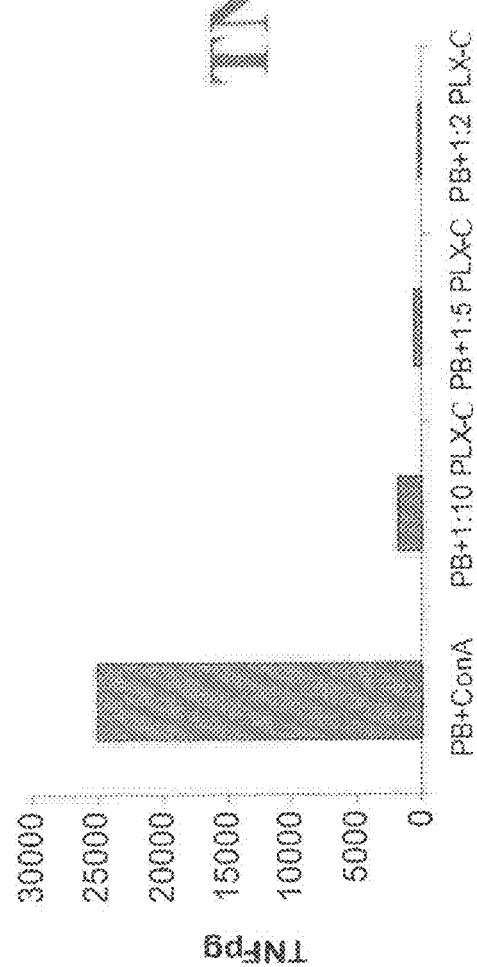
FIG. 13A
FIG. 13B

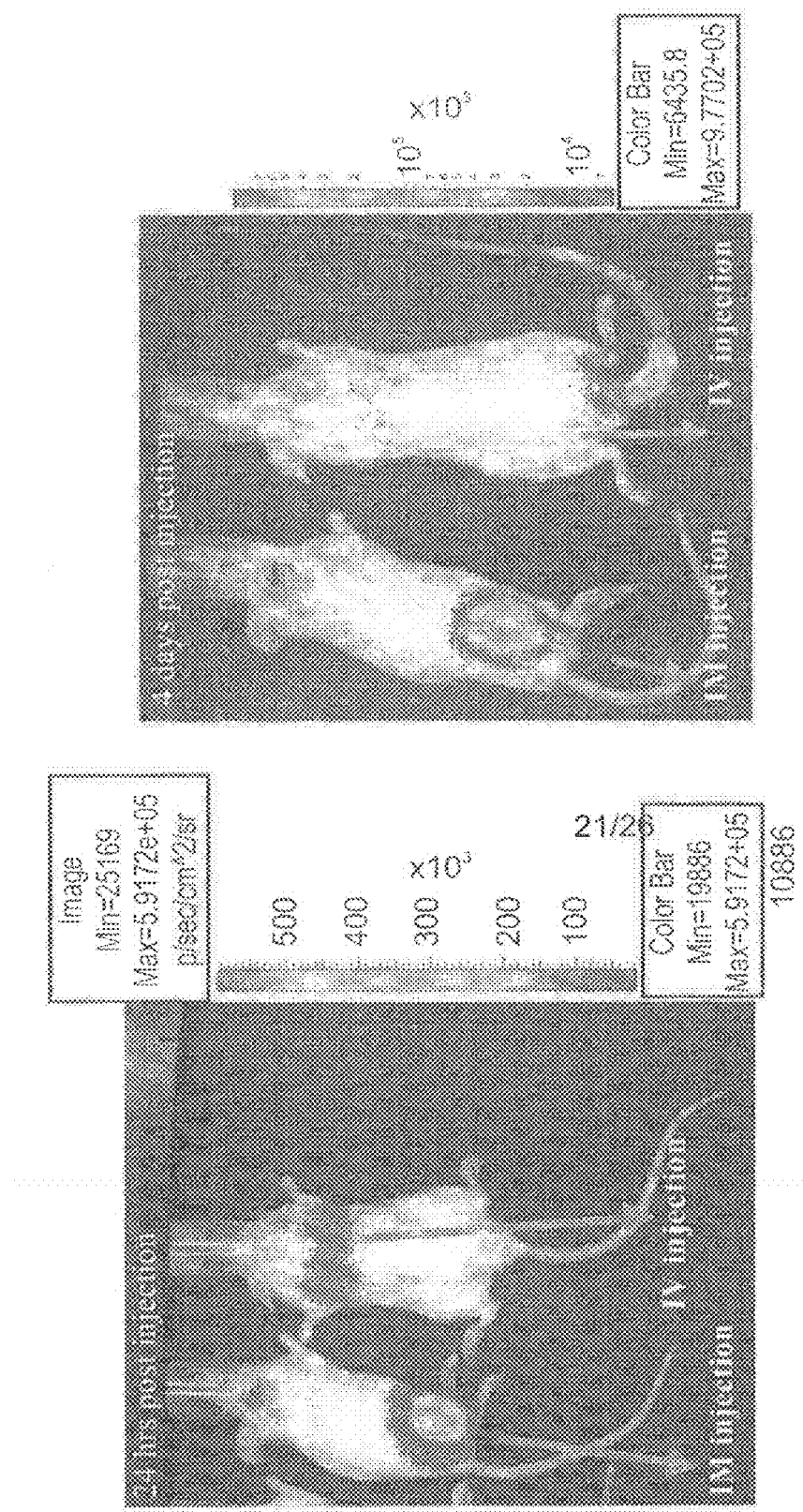

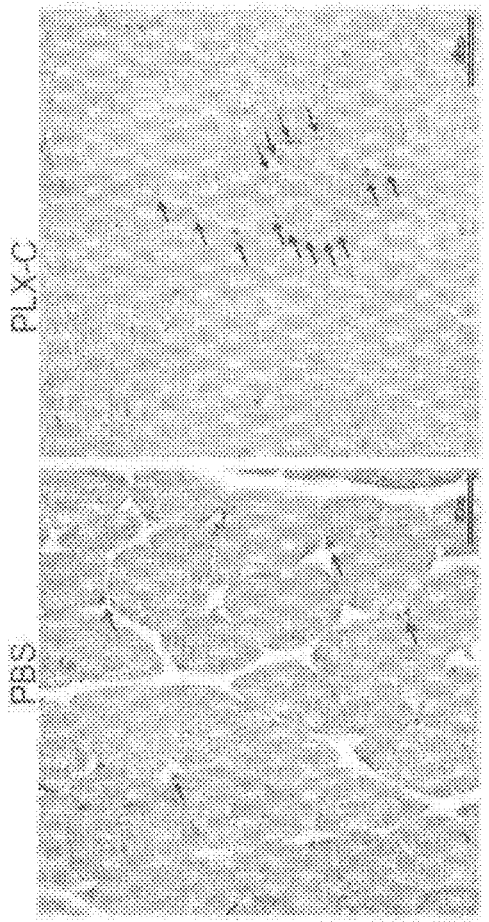
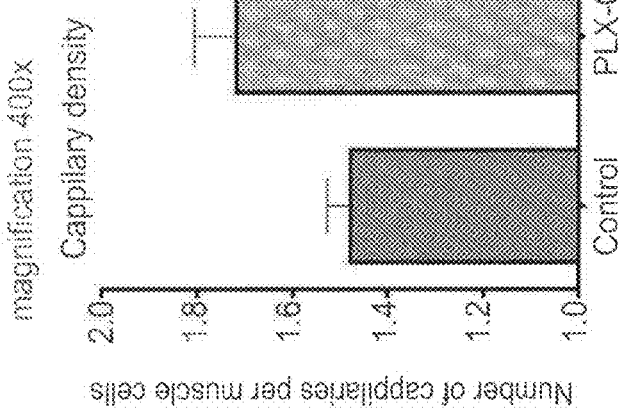
FIG. 19A
FIG. 19B
FIG. 19C

ADHERENT CELLS FROM ADIPOSE OR PLACENTA TISSUES AND USE THEREOF IN THERAPY

This is a continuation application of application Ser. No. 13/958,706, filed Aug. 5, 2013, pending, which is a continuation application of application Ser. No. 12/678,756, filed Mar. 18, 2010, now U.S. Pat. No. 8,529,888, which is a national stage application under 35 U.S.C. §371 of international application PCT/IL2008/01185, filed Sep. 2, 2008, which claims the benefit of U.S. Provisional Application Ser. No. 60/960,184, filed Sep. 19, 2007, each of which is incorporated by reference herein.

FIELD AND BACKGROUND OF THE INVENTION

The invention relates to methods of treating diseases using adherent cells from adipose or placenta tissues, more specifically, to methods of treating ischemia and/or medical conditions requiring connective tissue regeneration and/or repair using the adherent cells.

In the developing medical world a growing need exists for large amounts of adult stem cells for the purpose of cell engraftment and tissue engineering. In addition, adult stem cell therapy is continuously developing for treating and curing various conditions such as hematopoietic disorders, heart disease, Parkinson's disease, Alzheimer's disease, stroke, burns, muscular dystrophy, autoimmune disorders, diabetes and arthritis.

In recent years, considerable activity has focused on the therapeutic potential of mesenchymal stromal cells (MSCs) for various medical applications including tissue repair of damaged organs such as the brain, heart, bone and liver and in support of bone marrow transplantations (BMT). MSCs, a heterogeneous population of cells obtained from e.g. bone marrow, adipose tissue, placenta, and blood, is capable of differentiating into different types of mesenchymal mature cells (e.g. reticular endothelial cells, fibroblasts, adipocytes, osteogenic precursor cells) depending upon influences from various bioactive factors. Accordingly, MSCs have been widely studied in regenerative medicine as the foundation to build new tissues such as bone, cartilage and fat for the repair of injury or replacement of pathologic tissues and as treatment for genetic and acquired diseases [Fibbe and Noort, Ann N Y Acad Sci (2003) 996: 235-44; Horwitz et al., Cytotherapy (2005) 7(5): 393-5; Zimmet and Hare, Basic Res Cardiol (2005) 100(6): 471-81]. Furthermore, the multipotent ability of MSCs, their easy isolation and culture, as well as their high ex vivo expansion potential make them an attractive therapeutic tool [Fibbe and Noort, supra; Minguell et al. Exp Biol Med (Maywood) (2001) 226(6): 507-20].

Placental derived MSCs exhibit many markers common to MSCs isolated from other tissues, e.g. CD105, CD73, CD90 and CD29, and the lack of expression of hematopoietic, endothelial and trophoblastic-specific cell markers. Adipogenic, osteogenic, and neurogenic differentiation have been achieved after culturing placental derived MSCs under appropriate conditions [Yen et al., Stem Cells (2005) 23(1): 3-9]. Furthermore, MSCs isolated from placenta and cultured in vitro have been demonstrated to be immune privileged in a similar fashion as MSCs. Thus, the placenta provides an ethically non-controversial and easily accessible source of MSCs for experimental and clinical applications [Zhang et al., Exp Hematol (2004) 32(7): 657-64].

The present inventors have previously devised three dimensional (3D) culturing conditions suitable for expansion of placental derived MSCs (PCT Application No. IL2007/000380) fully incorporated herein by reference in its entirety.

Leading clinical uses of MSCs are summarized infra.

Ischemia

Peripheral Arterial Disease (PAD)

Peripheral arterial disease (PAD) is a chronic disease that progressively restricts blood flow in the limbs that can lead to serious medical complications. This disease is often associated with other clinical conditions, including hypertension, cardiovascular disease, hyperlipidemia, diabetes, obesity and stroke. Critical Limb Ischemia (CO) is used to describe patients with chronic ischemia induced pain, ulcers, tissue loss or gangrene in the limb. CO represents the end stage of PAD patients who need comprehensive treatment by a vascular surgery or vascular specialist. In contrast to coronary and cerebral artery disease, peripheral arterial disease (PAD) remains an under-appreciated condition that despite being serious and extremely prevalent is rarely diagnosed and even less frequently treated. Consequently, CO often leads to amputation or death and mortality rates in PAD patients exceed that of patients with myocardial infarction and stroke.

In attempts to treat ischemic conditions, various adult stem cells have been used. Thus, co-culturing of adipose tissue derived stromal cells (ADSC) and endothelial cells (EC) resulted in a significant increase in EC viability, migration and tube formation mainly through secretion of VEGF and HGF. Four weeks after transplantation of the stromal cells into the ischemic mouse hind limb the angiogenic scores were improved [Nakagami et al., J Atheroscler Thromb (2006) 13(2): 77-81]. Moon et al. [Cell Physiol Biochem. (2006) 17: 279-90] have tested the ability of adipose tissue-derived progenitor cells (ADSC) to treat limb ischemia in immunodeficient mice and demonstrated a significant increase in the laser Doppler perfusion index in ADSC-transplanted group.

In addition, when umbilical cord blood (UCB)-derived mesenchymal stem cells were transplanted into four men with Buerger's disease who had already received medical treatment and surgical therapies, ischemic rest pain, suddenly disappeared from their affected extremities [Kim et al., Stem Cells (2006) 24(6): 1620-6], Moreover, transplantation of human mesenchymal stem cells isolated from fetal membranes of term placenta (FMhMSC) into infracted rat hearts was associated with increased capillary density, normalization of left ventricular function, and significant decrease in scar tissue, which was enhanced when the stem cells were preconditioned with a mixed ester of hyaluronan with butyric and retinoic acid [Ventura et al., (2007) J. Biol. Chem., 282: 14243-52].

Stroke

Stroke is one of the leading causes of death around the world, causing approximately 9% of all deaths and consuming about 2-4% of total health-care costs. Although there has been a constant reduction in stroke mortality in developed countries, probably due improved control of stroke risk factors (especially high blood pressure, diabetes and cigarette smoking), stroke still leads to permanent damage (e.g. tissue damage, neurological damage).

New treatment regimens for stroke include stem cell therapy. Transplantation of stem cells or progenitors into the injured site, either locally or via intravenous routes, to replace nonfunctional cells, enhance proliferation and/or differentiation of endogenous stem or progenitor cells and supply necessary immune modulators has been contemplated and stand as the major cell-based strategy. Potential sources of stem/progenitor cells for stroke include fetal neural stem cells, embryonic, stem cells, neuroteratocarcinoma cells, umbilical cord blood-derived non-hematopoietic stem cells, bone marrow-derived stem cells and placenial-derived mesenchymal stem cells [Andres et al., Neurosurg Focus (2008) 24(3-4): E16].

In a recent study. Koh et. al. [Koh et al., Brain Res. (2008)] examined the neuroprotective effects and mechanisms of implanted human umbilical cord-derived mesenchymal stem cells (hUC-MSCs) in an ischemic stroke rat model. Twenty days after the induction of in-vitro neuronal differentiation, hUC-MSCs displayed morphological features of neurons and expressed neuronal cell markers and neuronal factors (e.g. glial cell line-derived neurotrophic factor, brain-derived neurotrophic factor). Furthermore, in-vivo implantation of the hUC-MSCs into the damaged hemisphere of immunosuppressed ischemic stroke rats improved neurobehavioral function and reduced infarct volume relative to control rats. Three weeks after implantation, hUC-MSCs were present in the damaged hemisphere and expressed neuron-specific markers, yet these cells did not become functionally active neuronal cells.

Orthopedic Applications

Various conditions and pathologies require connective tissue (e.g., bone, tendon and ligament) regeneration and/or repair. These include, for example, bone fractures, burns, burn wound, deep wound, degenerated bone, various cancers associated with connective tissue loss (e.g., bone cancer, osteosarcoma, bone metastases), and articular cartilage defect.

The use of autologous BM-MSCs to enhance bone healing has been described for veterinary and human orthopedic applications and include percutaneous injection of bone marrow for ligament healing (Carstanjen et al., 2006), treatment of bone defects by autografts or allografts of bone marrow in orthopedic clinic (Horwitz et al., 1999, Horwitz et al., 2002), regeneration of critical-sized bone defect in dogs using allogeneic [Arinzeh T L, et ah, J Bone Joint Surg Am. 2003, 85-A(10): 1927-35] or autologous [Bruder S P, et al., J Bone Joint Surg Am. 1998 July; 80(7):985-96] bone marrow-MSCs loaded onto ceramic cylinder consisting of hydroxyapatite-tricalcium phosphate, or in rabbit using allogeneic peripheral blood derived MSCs (Chao et al., 2006.), and extensive bone formation using MSCs implantation in baboon (Livingston et al., 2003).

Within the equine orthopedic field, mesenchymal stem cells of BM and adipose sources have been used experimentally for surgical treatment of subchondral-bone cysts, bone fracture repair [Kraus and Kirker-Head, Vet Surg (2006) 35(3): 232-42] and cartilage repair [Brehm et al., Osteoarthritis Cartilage (2006) 14(12): 1214-26; Wilke et al., J Orthop Res (2007) 25(7): 913-25] and clinically in the treatment of overstrain induced injuries of tendons in horses. Furthermore, different therapeutic approaches have been used to promote suspensory ligament healing in horses (Herthel, 2001). Herthel (2001) have demonstrated a novel biological approach to facilitate suspensory ligament healing that involves the intra lesional injection of autologous stem cells and associated bone marrow components to stimulate natural ligament regeneration.

Rabbit models for injured tendons showed that MSC-treated tissues were stronger and stiffer than natural repaired tissues (Gordon et al., 2005). In addition, seeding of cultured MSCs into a tendon gap resulted in significantly improved repair biomechanics (Young et al., 1998, Osiris Therapeutics, www.osiris.com).

Osiris Chondrogen (adult Mesenchymal Stem Cells) is being tested in patients in order to evaluate safety and efficacy. In MSC treated animals, surgically removed meniscal tissue was regenerated, the cartilage surface was protected, and lessened joint damage was observed in comparison to control animals. These benefits persisted in animal models at least through one year (Osiris Therapeutics, www.osiris.com).

SUMMARY OF THE INVENTION

According to an aspect of some embodiments of the present invention there is provided a method of treating ischemia in a subject in need thereof, the method comprising administering to the subject a therapeutically effective amount of adherent cells of a tissue selected from the group consisting of a placenta and an adipose tissue, thereby treating the ischemia in the subject.

According to an aspect of some embodiments of the present invention there is provided a method of treating a medical condition requiring connective tissue regeneration and/or repair in a subject in need thereof, the method comprising administering to the subject a therapeutically effective amount of adherent cells of a tissue selected from the group consisting of a placenta and an adipose tissue, thereby treating the medical condition requiring connective tissue regeneration and/or repair in the subject.

According to an aspect of some embodiments of the present invention there is provided a use of adherent cells from a tissue selected from the group consisting of a placenta and an adipose tissue for the manufacture of a medicament identified for treating ischemia.

According to an aspect of some embodiments of the present invention there is provided a use of adherent cells from a tissue selected from the group consisting of a placenta and an adipose tissue for the manufacture of a medicament identified for treating a medical condition requiring connective tissue regeneration and/or repair.

According to an aspect of some embodiments of the present invention there is provided an article of manufacture comprising a packaging material which comprises a label for use in treating ischemia, the packaging material packaging a pharmaceutically effective amount of adherent cells of a tissue selected from the group consisting of a placenta and an adipose tissue.

According to an aspect of some embodiments of the present invention there is provided an article of manufacture comprising a packaging material which comprises a label for use in treating a medical condition requiring connective tissue regeneration and/or repair, the packaging material packaging a pharmaceutically effective amount of adherent cells of a tissue selected from the group consisting of a placenta and an adipose tissue.

According to some embodiments of the invention, the adherent cells are capable of suppressing immune reaction in the subject.

According to some embodiments of the invention, at least 10% of the adherent cells are at a proliferative phase.

According to some embodiments of the invention, the ischemia is peripheral arterial disease (PAD).

According to some embodiments of the invention, the peripheral arterial disease (PAD) is critical limb ischemia (CLI).

According to some embodiments of the invention, the ischemia comprises ischemia of the central nervous system (CNS).

According to some embodiments of the invention, the ischemia is selected from the group consisting of peripheral arterial disease, ischemic vascular disease, ischemic heart disease, ischemic brain disease, ischemic renal disease and ischemic placenta.

According to some embodiments of the invention, the adherent cells are obtained from a three-dimensional (3D) culture.

According to some embodiments of the invention, the three-dimensional (3D) culture comprises a 3D bioreactor.

According to some embodiments of the invention, the culturing of the cells in the 3D culture is effected under perfusion.

According to some embodiments of the invention, the culturing conditions of the three-dimensional culture comprise an adherent material selected from the group consisting of a polyester and a polypropylene.

According to some embodiments of the invention, the culturing of the cells is effected for at least 3 days.

According to some embodiments of the invention, the culturing of the cells is effected until at least 10% of the cells are proliferating.

According to some embodiments of the invention, the adherent cells comprise a positive marker expression selected from the group consisting of CD73, CD90. CD29 and CD105.

According to some embodiments of the invention, the adherent cells comprise a negative marker expression selected from the group consisting of CD3, CD4, CD45, CD80, HLA-DR, CD11b, CD14, CD19, CD34 and CD79.

According to some embodiments of the invention, the adherent cells comprise an expression profile essentially as described herein.

According to some embodiments of the invention, the adherent cells comprise cells comprising a stromal stem cell phenotype.

According to some embodiments of the invention, the stromal stem cell phenotype comprises T cell suppression activity.

According to some embodiments of the invention, the connective tissue comprises tendon, bone and/or ligament.

According to some embodiments of the invention, the medical condition requiring connective tissue regeneration and/or repair is selected from the group consisting of bone fracture, bone cancer, burn wound, articular cartilage defect and deep wound.

According to some embodiments of the invention, the medical condition is selected from the group consisting of a subchondral-bone cyst, a bone fracture, an osteoporosis, an osteoarthritis, a degenerated bone, a bone cancer, a cartilage damage, an articular cartilage defect, a degenerative disc disease, an osteogenesis imperfecta (OI), a burn, a burn wound, a deep wound, a delayed wound-healing, an injured tendon and an injured ligament.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the embodiments of the invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-B are electron micrographs depicting the comparison of natural bone (FIG. 1A) and the structure of the PluriX™ 3D carrier 7 days after seeding adherent cells, imitating the bone micro-environment (FIG. 1B). FIGS. 1C-F are electron micrographs depicting the PluriX™ 3D matrix seeded with adherent cell, produced from bone marrow, 20 days (FIGS. 1C-D, magnified ×150 and 250 respectively) and 40 days (FIGS. 1E-F, magnified ×350 and 500 respectively) after seeding. FIG. 1G is a diagram of the Plurix 3D plug flow bioreactor with separate parts defined by numbers: Culture medium reservoir (1), gas mixture supply (2), filter (3), injection point (4), column in which the 3D carriers are placed (5) flow monitor (6), flow valve (6a), separating container (7), cell growth analyzers (8); peristaltic pump (9), sampling point (10), dissolved $O_2$ measurement electrode (11), pH measurement electrode (12), control system (13), fresh growth media (14), used growth media (15).

FIGS. 4A-D are bar graphs depicting a comparison of protein levels in adherent cells produced from the placenta cultured under 2D and 3D Conditions or conditioned media of same. FIGS. 4A-C depict levels of Flt-3 ligand (FIG. 4A), IL-6 (FIG. 4B) and SCF (FIG. 4C) in pg/ml, normalized for $1 \times 10^6$ cells/ml, as analyzed by ELISA, in the conditioned media of 2D and 3D cultured adherent cells. Results represent one of three independent experiments. FIG. 4D shows the expression levels of different cellular proteins, as analyzed by mass spectrometry with iTRAQ reagents labeled protein samples compared therebetween. Protein samples were taken from adherent cells grown under 2D (white bars) and 3D (grey bars) conditions. The figure represents one of two replica experiments. Note the difference in expression level of some of the proteins in cells and conditioned media of 2D and 3D culture conditions, FIGS. 5A-B show cells expressing calcified matrix, as indicated by Alizzarin Red S staining. FIGS. 5C-D show control cells, which were not treated with osteogenic induction medium and maintained a fibroblast like phenotype and demonstrating no mineralization.

FIG. 8C is a diagram of a Celligen™ bioreactor vessel and ports adapted from The New Brunswick Scientific web site.

FIG. 10A depicts negative expression of the endothelial marker CD31; FIG. 10B depicts negative expression of the endothelial marker KDR; and FIG. 10C depicts positive expression of the human fibroblast marker (D7-FIB). Of note, the red histograms for Isotype IgG1 (FITC) represent the negative control while the blue histograms represents the positively stained cells.

FIG. 11A depicts PLX-C expression of CD80; FIG. 11B depicts PLX-C expression of CD86; FIG. 11C depicts PLX-C expression of CD40; and FIG. 11D depicts PLX-C expression of HLA-A/B/C. Negative controls were prepared with relevant isotype fluorescence molecules. Of note, red histograms indicate PLX-C marker-expressing population of cells, blue histograms indicate bone marrow (BM) marker-expressing population of cells, and green histograms indicate mononuclear cell (MNC) marker expressing population of cells.

FIGS. 12A-B depict inhibition of lymphocyte proliferation by PLX-C. FIG. 12A depicts MLR tests performed with $2 \times 10^5$ peripheral blood (PB) derived MNC (donor A) stimulated with equal amount of irradiated (3000 Rad) PB derived MNCs (donor B) followed by addition of increasing amounts of PLX-C cells to the cultures. Three replicates of each group were seeded in 96-well plates. Proliferation rate was measured by [$^3$H]thymidine incorporation; FIG. 12B depict peripheral blood (PB) derived MNCs stimulated with ConA (1.5 mg/ml). Increasing amounts of PLX-C cells were added to the cultures. Three replicates of each group were seeded in 96-well plates. Proliferation rate was measured by [$^3$H]thymidine incorporation;

FIGS. 13A-C depict PLX-C regulation of pro-inflammatory and anti-inflammatory cytokine secretion following co-culture with peripheral blood cells. FIGS. 13A-B depict secretion of IFNγ (FIG. 13A) and TNFα (FIG. 13B) following co-culture of human derived MNCs (isolated from peripheral blood) stimulated with ConA with PLX-C; FIG. 13C depicts secretion of IFNγ, TNFα and IL-10 following co-culture of human derived MNCs (isolated from peripheral blood) stimulated with LPS with PLX-C. Supernatants were collected and subjected to cytokines analysis using ELISA.

FIGS. 16A-D depict injection of $2 \times 10^6$ luciferase expressing PLX-C cells into SCID/Beige mice. One mouse was injected IM and one IV. The injected mice were monitored using the IVIS system in order to asses the in vivo biodistribution of PLX-C. IVIS results of days 1 (FIG. 16A), day 4 (FIG. 16B), day 6 (FIG. 16C) and day 22 (FIG. 16D) are presented.

FIGS. 19A-C depict increased capillary density after PLX-C treatment. FIG. 19A depicts capillary density in mice treated with PBS; FIG. 19B depicts capillary density in mice treated with PLX-C cells; FIG. 19C is a bar graph depicting the number of capillaries per muscle cells. Of note, increase capillary density was noted in PLX-C treated mice but not in control mice, following induced limb ischemia demonstrated by specific capillary staining.

FIG. 20A is a bar graph depicting oxidative stress (Nitrotyrosin staining); and FIG. 20B is a bar graph depicting endothelial inflammation (VCAM evaluation). Of note, reduced oxidative stress and endothelial inflammation is noted in mice treated with PLX-C.

DESCRIPTION OF THE EMBODIMENTS OF THE INVENTION

The invention is of, in some embodiments, methods of increasing angiogenesis in a tissue and treating ischemia or medical conditions requiring connective tissue regeneration and/or repair using adherent cells of placenta or adipose tissues.

The principles and operation of the invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

While reducing the invention to practice, the present inventors have uncovered that adherent cells from a placenta or an adipose tissue are highly efficient in increasing angiogenesis in a tissue and in treating ischemia and medical conditions requiring connective tissue regeneration and/or repair.

Figures 20A, 20B:
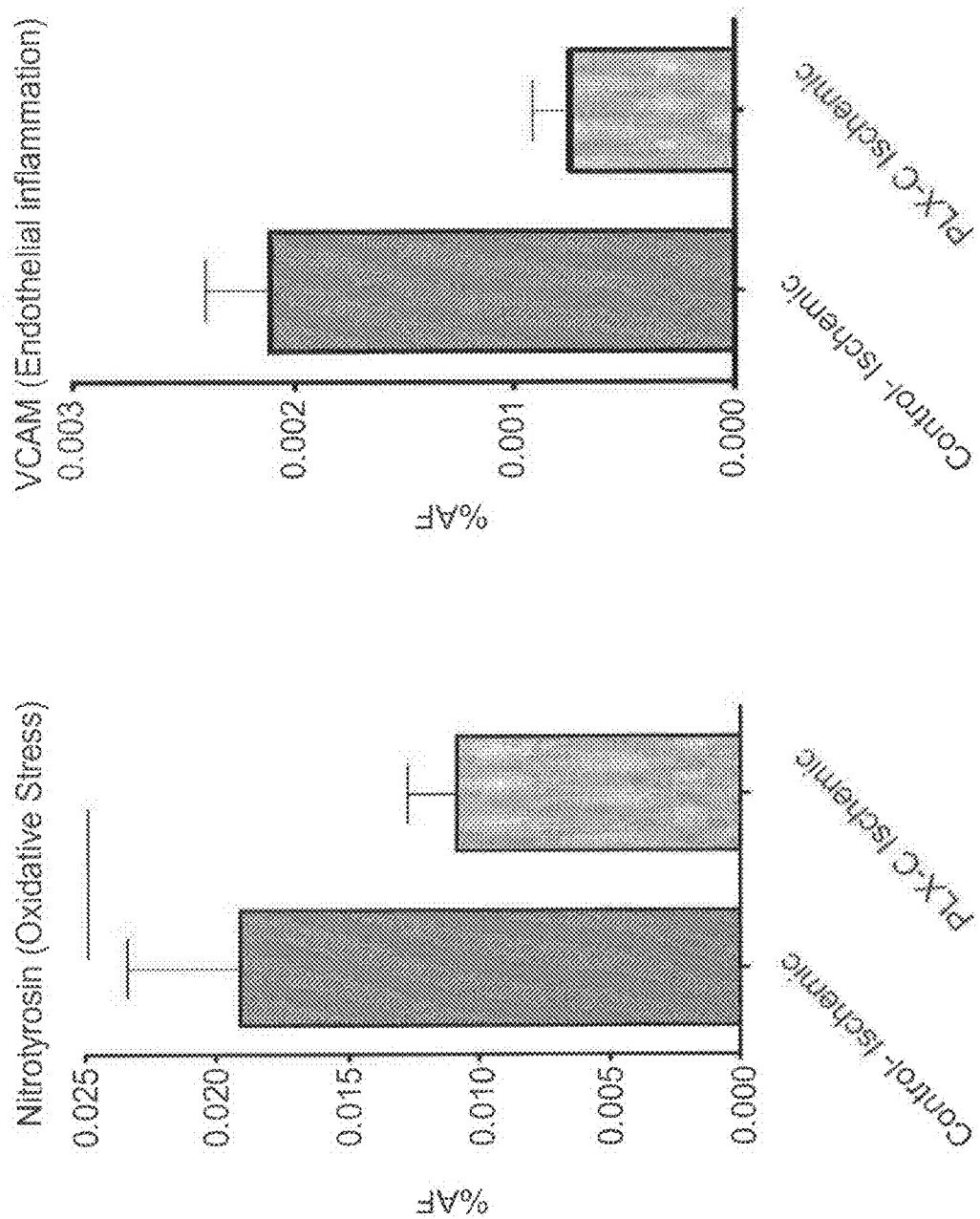
FIGS. 20A-B depict reduced oxidative stress and endothelial inflammation following PLX-C administration.

As is illustrated herein below and in Example 1-8 of the Examples section which follows, the present inventors were able to expand adipose and placenta-derived adherent cells which comprise stromal stem cells properties. Cells expanded accordingly were found viable, following cryopreservation, as evidenced by adherence and re-population assays (see Example 1). Flow cytometry analysis of placenta-derived adherent cells uncovered a distinct marker expression pattern (see FIGS. 3A-B). As is further shown in Example 6 of the Examples section which follows, implantation of placental derived adherent cells significantly induced blood flow in the hip and foot (FIG. 17) of mice subjected to artery ligation (the ischemic hind limb model), significantly improved limb function (FIG. 18), increased capillary density (FIGS. 19A-C) and reduced oxidative stress and endothelial inflammation (FIGS. 20A-B).

Thus, according to one aspect of the invention, there is provided a method of increasing angiogenesis in a tissue. The method is effected by contacting the tissue with adherent cells of a tissue selected from the group consisting of a placenta and an adipose tissue, thereby increasing the angiogenesis in the tissue.

As used herein the phrase "increasing angiogenesis in a tissue" refers to increasing (inducing, upregulating) the process of generating new capillary blood vessels in a tissue.

As used herein the phrase "adherent cells" refers to a homogeneous or heterogeneous population of cells which are anchorage dependent, i.e., require attachment to a surface in order to grow in vitro.

As used herein the phrase "adipose tissue" refers to a connective tissue which comprises fat cells (adipocytes).

As used herein the term "placenta tissue" refers to any portion of the mammalian female organ which lines the uterine wall and during pregnancy envelopes the fetus, to which it is attached by the umbilical cord. Following birth, the placenta is expelled (and is referred to as a post partum placenta). In an exemplary embodiment, placenta refers to whole placenta.

Placenta or adipose tissue derived adherent cells can be propagated using two dimensional or three dimensional culturing conditions.

Conditions for propagating adherent cells in 2D culture are further described hereinbelow and in the examples section which follows.

As used herein the phrase "three dimensional culture" refers to a culture in which the cells are disposed to conditions which are compatible with cell growth while allowing the cells to grow in more than one layer. It is well appreciated that the in situ environment of a cell in a living organism (or a tissue) is in a three dimensional architecture. Cells are surrounded by other cells. They are held in a complex network of extra cellular matrix nanoscale fibers that allows the establishment of various local microenvironments. Their extra cellular ligands mediate not only the attachment to the basal membrane but also access to a variety of vascular and lymphatic vessels. Oxygen, hormones and nutrients are ferried to cells and waste products are carried away. The conditions in the three dimensional culture of the invention are designed to mimic such an environment as is further exemplified below.

It will be appreciated that the conditions of the three-dimensional culture are such that enable expansion of the adherent cells.

As used herein the terms "expanding" and "expansion" refer to substantially differentiation-less maintenance of the cells and ultimately cell growth, i.e., increase of a cell population (e.g., at least 2 fold) without differentiation accompanying such increase.

As used herein the terms "maintaining" and "maintenance" refer to substantially differentiation-less cell renewal, i.e., substantially stationary cell population without differentiation accompanying such stationarity.

As mentioned, the adherent cells of this aspect of the invention are retrieved from an adipose or placental tissue.

Placental cells may be obtained from a full-term or pre-term placenta. Placenta is preferably collected once it has been ex blooded. The placenta is preferably perfused for a period of time sufficient to remove residual cells. The term "perfuse" or "perfusion" used herein refers to the act of pouring or passaging a fluid over or through an organ or tissue. The placental tissue may be from any mammal; for example, the placental tissue is human. A convenient source of placental tissue is from a post partum placenta (e.g., 1-6 hours), however, the source of placental tissue or cells or the method of isolation of placental tissue is not critical to the invention.

Placenta derived adherent cells may be obtained from both fetal (i.e., amnion or inner parts of the placenta, see Example 1) and maternal (i.e., decidua basalis, and decidua parietalis) parts of the placenta. Tissue specimens are washed in a physiological buffer [e.g., phosphate-buffered saline (PBS) or Hank's buffer]. Single-cell suspensions are made by treating the tissue with a digestive enzyme (see below) or/and mincing and flushing the tissue parts through a nylon filter or by gentle pipetting (Falcon, Becton, Dickinson, San Jose, Calif.) with washing medium.

Adipose tissue derived adherent cells may be isolated by a variety of methods known to those skilled in the art. For example, such methods are described in U.S. Pat. No. 6,153,432. The adipose tissue may be derived from omental/visceral, mammary, gonadal, or other adipose tissue sites. One source of adipose tissue is omental adipose. In humans, the adipose is typically isolated by liposuction.

Isolated adherent cells from adipose tissue may be derived by treating the tissue with a digestive enzyme such as collagenase, trypsin and/or dispase; and/or effective concentrations of hyaluonidase or DNAse; and ethylenediaminetetra-acetic acid (EDTA); at temperatures between 25-50° C., for periods of between 10 minutes to 3 hours. The cells may then be passed through a nylon or cheesecloth mesh filter of between 20 microns to 1 mm. The cells are then subjected to differential centrifugation directly in media or over a Ficoll or Percoll or other particulate gradient. Cells are centrifuged at speeds of between 100 to 3000×g for periods of between 1 minutes to 1 hour at temperatures of between 4-50° C. (see U.S. Pat. No. 7,078,230).

In addition to placenta or adipose tissue derived adherent cells, the invention also envisages the use of adherent cells from other cell sources which are characterized by stromal stem cell phenotype (as will be further described herein below). Tissue sources from which adherent cells can be retrieved include, but are not limited to, cord blood, scalp, hair follicles [e.g. as described in Us Pat. App. 20060172304], testicles [e.g., as described in Guan K., et al., Nature. 2006 Apr. 27; 440(7088): 1199-203], human olfactory mucosa [e.g., as described in Marshall, C T., et al., Histol Histopathol. 2006 Jun.; 21(6):633-43], embryonic yolk sac [e.g., as described in Geijsen N, Nature. 2004 Jan. 8; 427(6970):148-54] and amniotic fluid [Pietemella et al. (2004) Stein Cells 22:1338-1345], all of which are known to include mesenchymal stem cells. Adherent cells from these tissue sources can be isolated by culturing the cells on an adherent surface, thus isolating adherent cells from other cells in the initial population.

Regardless of the origin (e.g., placenta or adipose tissue), cell retrieval is preferably effected under sterile conditions. Once isolated cells are obtained, they are allowed to adhere to an adherent material (e.g., configured as a surface) to thereby isolate adherent cells. Culturing may proceed under 2D conditions as described in Example 4 of the Examples section and cells may be further transferred to 3D conditions As used herein "an adherent material" refers to a synthetic, naturally occurring or a combination of same of a non-cytotoxic (i.e., biologically compatible) material having a chemical structure (e.g., charged surface exposed groups) which may retain the cells on a surface.

Examples of adherent materials which may be used in accordance with this aspect of the invention include, but are not limited to, a polyester, a polypropylene, a polyalkylene, a polyfluorochloroethylene, a polyvinyl chloride, a polystyrene, a polysulfone, a cellulose acetate, a glass fiber, a ceramic particle, a matrigel, an extra cellular matrix component (e.g., fibronectin, chondronectin, laminin), a collagen, a poly L lactic acid and an inert metal fiber.

Further steps of purification or enrichment for stromal stem cells may be effected using methods which are well known in the art (such as by FACS using stromal stem cell marker expression, as further described herein below).

Non-limiting examples of base media useful in culturing according to the invention include Minimum Essential Medium Eagle, ADC-1, LPM (Bovine Serum Albumin-free), F10(HAM), F12 (HAM), DCCM1, DCCM2, RPMI 1640, BGJ Medium (with and without Fitton-Jackson Modification), Basal Medium Eagle (BME—with the addition of Earle's salt base), Dulbecco's Modified Eagle Medium (DMEM-without serum), Yamane, IMEM-20, Glasgow Modification Eagle Medium (GMEM), Leibovitz L-15 Medium, McCoy's 5A Medium, Medium M199 (M199E—with Earle's sale base), Medium M199 (M199H—with Hank's salt base), Minimum Essential Medium Eagle (MEM-E—with Earle's salt base), Minimum Essential Medium Eagle (MEM-H—with Hank's salt base) and Minimum Essential Medium Eagle (MEM-NAA with non essential amino acids), among numerous others, including medium 199, CMRL 1415, CMRL 1969, CMRL 1066, NCTC 135, MB 75261, MAB 8713, DM 145, Williams' G, Neuman & Tytell, Higuchi, MCDB 301, MCDB 202, MCDB 501, MCDB 401, MCDB 411, MDBC 153. A preferred medium for use in the invention is DMEM. These and other useful media are available from GIBCO, Grand Island, N.Y., USA and Biological Industries, Bet HaEmek, Israel, among others. A number of these media are summarized in Methods in Enzymology, Volume LVIII, "Cell Culture", pp. 62 72, edited by William B. Jakoby and Ira H. Pastan, published by Academic Press, Inc.

The medium may be supplemented such as with serum such as fetal serum of bovine or other species, and optionally or alternatively, growth factors, vitamins (e.g. ascorbic acid), cytokines, salts (e.g. B-glycerophosphate), steroids (e.g. dexamethasone) and hormones e.g., growth hormone, erythropoeitin, thrombopoietin, interleukin 3, interleukin 6, interleukin 7, macrophage colony stimulating factor, c-kit ligand/stem cell factor, osteoprotegerin ligand, insulin, insulin like growth factors, epidermal growth factor, fibroblast growth factor, nerve growth factor, cilary neurotrophic factor, platelet derived growth factor, and bone morphogenetic protein at concentrations of between picogram/ml to milligram/ml levels.

It is further recognized that additional components may be added to the culture medium. Such components may be antibiotics, antimycotics, albumin, amino acids, and other components known to the art for the culture of cells. Additionally, components may be added to enhance the differentiation process when needed (see further below).

It will be appreciated that in case the adherent cells of the invention are administered to a human subject, the cells and the culture medium (e.g., with the above described medium additives) should be substantially xeno-free, i.e., devoid of any animal contaminants e.g., *mycoplasma*. For example, the culture medium can be supplemented with a serum-replacement, human serum and/or synthetic or recombinantly produced factors.

As mentioned, once adherent cells are at hand they may be passaged to two dimensional or three dimensional settings (see Examples 1 and 4 of the Examples section which follows). It will be appreciated though, that the cells may be transferred to a 3D-configured matrix immediately after isolation or alternatively, may be passaged to three dimensional settings following two dimensional conditions (as mentioned hereinabove).

Thus, the adherent material of this aspect of the invention is configured for 3D culturing thereby providing a growth matrix that substantially increases the available attachment surface for the adherence of the cells so as to mimic the infrastructure of the tissue (e.g., placenta).

For high scale production, culturing can be effected in a 3D bioreactor.

Examples of such bioreactors include, but are not limited to, a plug flow bioreactor, a continuous stirred tank bioreactor, a stationary-bed bioreactor, a CelliGen Plus® bioreactor system (New Brunswick Scientific (NBS) or a BIO-FLO 310 bioreactor system (New Brunswick Scientific (NBS).

As shown Example 4 of the Examples section, the Celligen bioreactor is capable of 3D expansion of adherent cells under controlled conditions (e.g. pH, temperature and oxygen levels) and with constant cell growth medium perfusion. Furthermore, the cell cultures can be directly monitored for concentration levels of glucose, lactate, glutamine, glutamate and ammonium. The glucose consumption rate and the lactate formation rate of the adherent cells enable to measure cell growth rate and to determine the harvest time.

Other 3D bioreactors that can be used with the invention include, but are not limited to, a continuous stirred tank bioreactor, where a culture medium is continuously fed into the bioreactor and a product is continuously drawn out, to maintain a time-constant steady state within the reactor. A stirred tank bioreactor with a fibrous bed basket is available for example at New Brunswick Scientific Co., Edison, N.J.), A stationary-bed bioreactor, an air-lift bioreactor, where air is typically fed into the bottom of a central draught tube flowing up while forming bubbles, and disengaging exhaust gas at the top of the colunm], a cell seeding perfusion bioreactor with Polyactive foams [as described in Wendt, D. et al., Biotechnol Bioeng 84: 205-214, (2003)] tubular poly-L-lactic acid (PLLA) porous scaffolds in a Radial-flow perfusion bioreactor [as described in Kitagawa et al., Biotechnology and Bioengineering 93(5): 947-954 (2006). Other bioreactors which can be used in accordance with the invention are described in U.S. Pat. Nos. 6,277,151, 6,197,575, 6,139,578, 6,132,463, 5,902,741 and 5,629,186.

Cell seeding is preferably effected 100,000-1,500,000 cells/mm at seeding. In an exemplary embodiment a total of $150\pm30\times10^6$ cells are seeded, $3$-$5\times10^6$ cell/gr carrier are seeded, or $0.015$-$0.1\times10^6$ cell/ml are seeded.

Cells can be harvested when at least about 10% of cells are proliferating while avoiding uncontrolled differentiation and senescence.

Culturing is effected for at least about 2 days, 3 days, 4 days, 5 days, 10 days, days, a month or even more. It will be appreciated that culturing in a bioreactor may prolong this period. Culturing of the adherent cells in the 3D culture can be effected under a continuous flow of a culture medium.

Passaging may also be effected to increase cell number. It will be appreciated that culture medium may be changed in order to prolong and improve culturing conditions.

Adherent cells of some embodiments of the present invention comprise at least about 10%, 28%, 30%, 50%, 80% or more proliferative cells (as can be assayed by FACS monitoring S and G2/M phases).

Adherent cells of some embodiments of the invention may comprise at least one "stromal stem cell phenotype".

As used herein "a stromal stem cell phenotype" refers to a structural or functional phenotype typical of a bone-marrow derived stromal (i.e., mesenchymal) stem cell As used herein the phrase "stem cell" refers to a cell which is not terminally differentiated.

Thus for example, the cells may have a spindle shape. Alternatively or additionally the cells may express a marker or a collection of markers (e.g. surface marker) typical to stromal stem cells. Examples of stromal stem cell surface markers (positive and negative) include but are not limited to CD105+, CD29+, CD44+, CD73+, CD90+, CD3−, CD4−, CD34−, CD45−, CD80−, CD19−, CD5−, CD20−, CD11B−, CD14−, CD19−, CD79−, H-LA-DR−, and FMC7−. Other stromal stem cell markers include but are not limited to tyrosine hydroxylase, nestin and H—NF.

Adherent cells of placenta tissue generated according to the present teachings have a gene expression profile essentially as described in Example 4 of the Examples section which follows.

Examples of functional phenotypes typical of stromal stem cells include, but are not limited to, T cell suppression activity (don't stimulate T cells and conversely suppress same), hematopoietic stem cell support activity, as well as any of adipogenic, hepatogenic, osteogenic and neurogenic differentiation.

Any of these structural or functional features can be used to qualify the cells of the invention (see Examples 4 of the Examples section which follows).

Populations of cells generated according to the present teachings are characterized by a unique protein expression profile as is shown in Example 1 of the Examples section. Thus for example, adherent cells of placenta or adipose tissue generated according to the present teachings are capable of expressing and/or secreting high levels of selected factors. For example, such cells express or secrete SCF, Flt-3, H2A histone family (H2AF) or Aldehyde dehydrogenase X (ALDH X) at least 2, 3, 4, 5, 6, 7, 8, 9, 10, 11 or even 12 fold higher than that expressed or secreted by adherent cells of placenta or adipose tissue grown in a 2D culture. Additionally or alternatively, population of cells of the invention secrete or express IL-6, eukaryotic translation elongation factor 2 (EEEF2), reticulocalbin 3, EF-hand calcium binding domain (RCN2) or calponin 1 basic smooth muscle (CNN1) at a level least 2, 3 or 5 fold higher than that expressed or secreted by adherent cells of placenta or adipose tissue grown in a 2D culture. Additionally or alternatively, population of cells of the invention are characterized by lower level of expression of various other proteins as compared to 2D cultured cells. Thus for example, secrete or express less than 0.6, 0.5, 0.25 or 0.125 of the expression level of heterogeneous nuclear ribonucleoprotein H1 (Hnrph1), CD44 antigen isoform 2 precursor, 3 phosphoadenosine 5 phosphosulfate synthase 2 isoform a (Papss2) or ribosomal protein L7a (rpL7a) expressed or secreted by adherent cells of placenta or adipose tissue grown in a 2D culture.

As is shown in Examples 3-4 of the Examples section which follows, the adherent cells, and particularly 3D-adherent cells, were found to suppress the immune reaction of human cord blood mononuclear cells in a mixed lymphocyte reaction (MLR) assay, thus exhibit biological activities which may be preferentially used in the clinic (e.g., T cell suppression activity, hematopoietic stem cell support activity).

According to one embodiment of the invention, the adherent cells of the invention are capable of suppressing immune reaction in a subject.

As used herein the phrase "suppressing immune reaction in a subject" refers to decreasing or inhibiting the immune reaction occurring in a subject in response to an antigen (e.g., a foreign cell or a portion thereof). The immune response which can be suppressed by the adherent cells include the humoral immune responses, and cellular immune responses, which involve specific recognition of pathogen antigens via antibodies and T-lymphocytes (proliferation of T cells), respectively.

According to one embodiment of the invention, the adherent cells of the invention are characterized by a higher immunosuppressive activity than that of adherent cells of the placenta or the adipose tissue grown in a two-dimensional (2D) culture.

According to one embodiment of the invention, the immunosuppressive activity comprises reduction in T cell proliferation.

As mentioned hereinabove and described in Example 6 of the Examples section which follows, the adherent cells of the invention induced angiogenesis in vivo (e.g., blood flow in the hip and leg), significantly improved limb function of animals subjected to arterial ligation, increased capillary density and reduced oxidative stress and endothelial inflammation. Furthermore, as described in detail in Example 7 of the Examples section which follows, the adherent cells of the invention significantly improved recovery from stroke in a rat model.

Thus, according to another aspect of the invention, there is provided a method of treating ischemia in a subject in need thereof. The method is effected by administering to the subject a therapeutically effective amount of the adherent cells of the invention, thereby treating the ischemia in the subject.

The term "ischemia" as used herein refers to any pathology (disease, condition, syndrome or disorder) characterized by or associated with insufficient angiogenesis. Examples include, but are not limited to, a peripheral arterial disease (PAD) such as limb ischemia and critical limb ischemia (CLI), ischemic heart disease, ischemic brain disease (e.g. stroke), delayed wound-healing, delayed ulcer healing, reproduction associated disorders, arteriosclerosis, ischemic vascular disease, ischemic heart disease, myocardial ischemia, coronary artery disease (CAD), atherosclerotic cardiovascular disease, left main coronary artery disease, arterial occlusive disease, peripheral ischemia, peripheral vascular disease, vascular disease of the kidney, peripheral arterial disease, limb ischemia, lower extremity ischemia, cerebral ischemia, cerebro vascular disease, retinopathy, retinal repair, remodeling disorder, von Hippel-Lindau syndrome, hereditary hemorrhagic telengiectasiaischemic vascular disease, Buerger's disease, ischemic renal disease and ischemic placenta.

As used herein the term "treating" refers to inhibiting or arresting the development of a pathology (e.g., ischemia) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. The term "treating" may also refer to alleviating or diminishing a symptom associated with the pathology.

As used herein the phrase "subject in need thereof" refers to any subject (e.g., mammal), such as a human subject who is diagnosed with or suffers from the pathology.

As mentioned hereinabove and described in Example 8 of the Examples section which follows, the present inventors have found that the adherent cells of the invention are capable of connective tissue regeneration and/or repair.

Thus, according to yet an additional aspect of the invention, there is provided a method of treating a medical condition requiring connective tissue regeneration and/or repair in a subject in need thereof. The method is effected by administering to the subject a therapeutically effective amount of the adherent cells of the invention.

The phrase "connective tissue" refers to a supporting framework tissue comprising strands of collagen, elastic fibers (e.g., between and around muscle and blood vessels) and simple cells. Examples of connective tissues include, but are not limited to dense connective tissue (e.g., ligament, tendon, periodontal ligament), areolar connective tissue (e.g., with proteinaceous fibers such as collagen and elastin), reticular connective tissue, adipose tissue, blood, bone, cartilage, skin, intervertebral disc, dental pulp, dentin, gingival, extracellular matrix (ECM)-forming cells, loose connective tissue and smooth muscle cells.

As used herein the phrase "medical condition requiring connective tissue regeneration and/or repair" refers to any pathology characterized by connective tissue damage (i.e., non-functioning tissue, cancerous or pre-cancerous tissue, broken tissue, fractured tissue, fibrotic tissue, or ischemic tissue) or loss (e.g., following a trauma, an infectious disease, a genetic disease, and the like). Non-limiting examples of such pathologies include, bone fracture, bone cancer (e.g., osteosarcoma, bone cancer metastasis), burn wound, articular cartilage defect and deep wound.

The phrase "administering to the subject" refers to the introduction of the cells of the invention to target tissue. The cells can be derived from the recipient or from an allogeneic or xenogeneic donor. This phrase also encompasses "transplantation", "cell replacement" or "grafting" of the cells of the invention into the subject.

The subject may be any mammal in need of connective tissue regeneration and/or repair including e.g. human or domesticated animals including, but not limited to, horses (i.e. equine), cattle, goat, sheep, pig, dog, cat, camel, alpaca, llama and yak.

According to an embodiment of the present teachings, the adherent cells of the present invention may be used to treat conditions including subchondral-bone cysts, bone fractures, osteoporosis, osteoarthritis, degenerated bone, various cancers associated with connective tissue loss (e.g., bone cancer, osteosarcoma, bone metastases), cartilage damage, articular cartilage defect, degenerative disc disease, osteogenesis imperfecta (OI), burns, burn wounds, deep wounds, delayed wound-healing, injured ligaments and injured tendons e.g. overstrain-induced injuries of tendons in horses and other subjects in need thereof (as stated above).

Cells which may be administered in accordance with this aspect of the invention include the above-described adherent cells which may be cultured in three-dimensional or two dimensional settings as well as mesenchymal and-non mesenchymal partially or terminally differentiated derivatives of same.

Methods of deriving lineage specific cells from the stromal stem cells of the invention are well known in the art. See for example, U.S. Pat. Nos. 5,486,359, 5,942,225, 5,736,396, 5,908,784 and 5,902,741.

The cells may be naïve or genetically modified such as to derive a lineage of interest (see U.S. Pat. Appl. No. 20030219423).

The cells may be of autologous or non-autologous source (i.e., allogeneic or xenogeneic) of fresh or frozen (e.g., cryo-preserved) preparations.

Depending on the medical condition, the subject may be administered with additional chemical drugs (e.g., immunomodulatory, chemotherapy etc.) or cells.

Since non-autologous cells may induce an immune reaction when administered to the body several approaches have been developed to reduce the likelihood of rejection of non-autologous cells. These include either suppressing the recipient immune system or encapsulating the non-autologous cells in immunoisolating, semipermeable membranes before transplantation.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol Biotechnol. 2001, 17: 249-60, and Lu M Z, et al., A novel cell encapsulation method using photosensitive poly(allylamine alpha-cyanocinnamylideneacetate). J Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 µm. Such microcapsules can be further encapsulated with additional 2-5 µm ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 µm (Canaple L. et al., Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE), etanercept, TNF.alpha. blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a "pharmaceutical composition" refers to a preparation of the adherent cells of the invention (i.e., adherent cells of a tissue selected from the group consisting of placenta and adipose tissue, which are obtained from a three-dimensional culture), with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

According to a preferred embodiment of the invention, the pharmaceutical carrier is an aqueous solution of saline.

Techniques for formulation and administration of drugs may be found in "Remington's Pharmaceutical Sciences," Mack Publishing Co., Easton, Pa., latest edition, which is incorporated herein by reference.

One may administer the pharmaceutical composition in a systemic manner (as detailed hereinabove). Alternatively, one may administer the pharmaceutical composition locally, for example, via injection of the pharmaceutical composition directly into a tissue region of a patient.

Pharmaceutical compositions of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, physiological salt buffer, or freezing medium containing cryopreservents. For transmucosal administration, penetrants appropriate to the barrier to be permeated are used in the formulation. Such penetrants are generally known in the art.

For any preparation used in the methods of the invention, the therapeutically effective amount or dose can be estimated initially from in vitro and cell culture assays. Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, Parkinson's patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively regulate the neurotransmitter synthesis by the implanted cells. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated Parkinson's patient will be administered with an amount of cells which is sufficient to alleviate the symptoms of the disease, based on the monitoring indications.

Models for ligament injury include, but are not limited to, rabbit model of anterior cruciate ligament reconstruction using mesenchymal stem cells [Jit-Kheng et al., Arthroscopy (2004) 20(9): 899-910], goat model for use of long-term bioresorbable scaffolds for anterior cruciate ligament repair [Altman et al., J Am Acad Orthop Surg. (2008) 16(4):177-187]. Models for tendon repair include, but are not limited to, adult New Zealand White rabbit model for autologous mesenchymal stem cell-mediated repair of tendon [Awad et al., Tissue Eng. (1999) 5(3):267-77]. Models for bone repair were described in e.g. Stem Cells in Endocrinology, Humana Press (2005) 183-206, describing the manipulation of mesenchymal stem cells for bone repair.

Following transplantation, the cells of the invention preferably survive in the diseased area for a period of time (e.g. about 1 month), such that a therapeutic effect is observed.

Compositions including the preparation of the invention formulated in a compatible pharmaceutical carrier may also be prepared, placed in an appropriate container, and labeled for treatment of an indicated condition.

Compositions of the invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

The adherent cells of the invention can be suitably formulated as pharmaceutical compositions which can be suitably packaged as an article of manufacture. Such an article of manufacture comprises a packaging material which comprises a label for use in increasing angiogenesis in a tissue, treating ischemia and/or treating a pathology requiring connective tissue regeneration and/or repair, wherein the packaging material packaging the adherent cells of the invention.

It will be appreciated that the adherent cells of the present invention are capable of inducing immunosuppression and/or tolerance in a subject. Thus, the adherent cells may be used to treat any condition in need of immunosuppression and/or tolerance. Such conditions included, but are not limited to, autoimmune diseases and inflammatory diseases (including acute and chronic inflammatory diseases) including, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2: S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2): 157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98

(8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome, diseases include, but are not limited to autoimmune diseases of the pancreas, Type 1 diabetes (Castano L. and Eisenbatth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March, 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2): 122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March, 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Furthermore, the adherent cells may be used to treat diseases associated with transplantation of a graft including, but are not limited to, graft rejection, chronic graft rejection, subacute graft rejection, hyperacute graft rejection, acute graft rejection and graft versus host disease.

As used herein the term "about" refers to ±10%.

Additional objects, advantages, and novel features of the invention will become apparent to one ordinarily skilled in the art upon examination of the following examples, which are not intended to be limiting. Additionally, each of the various embodiments and aspects of the invention as delineated hereinabove and as claimed in the claims section below finds experimental support in the following examples.

EXAMPLES

Reference is now made to the following examples, which together with the above descriptions illustrate the invention in a non-limiting fashion.

Generally, the nomenclature used herein and the laboratory procedures utilized in the invention include molecular, biochemical, microbiological andrecombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook". Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Production and Culturing of Adherent Cells from Bone Marrow, Placenta and Adipose Tissues Adherent cells were cultured in a bioreactor system containing 3D carriers to produce 3D-adherent cells, characterized by a specific cell marker expression profile. Growth efficiency was tested through cell count. The differentiation capacity of these cells was tested by culturing in a differentiation medium.

Materials and Experimental Procedures

Bone marrow adherent cells—Bone marrow (BM) adherent cells were obtained from aspirated sterna marrow of hematologically healthy donors undergoing open-heart surgery or BM biopsy. Marrow aspirates were diluted 3-fold in Hank's Balanced Salts Solution (HBSS; GIBCO BRL/Invitrogen, Gaithersburg Md.) and subjected to Ficoll-Hypaque (Robbins Scientific Corp. Sunnyvale, Calif.) density gradient centrifugation. Thereafter, marrow mononuclear cells (<1.077 gm/cm$^3$) were collected, washed 3 times in HBSS and resuspended in growth media [DMEM (Biological Industries, Beit Ha'emek, Israel) supplemented with 10% FCS (GIBCO BRL), 10$^{-4}$ M mercaptoethanol (Merck, White House Station, N.J.), Pen-Strep-Nystatin mixture (100 U/ml:100 µg/ml:1.25 un/ml; Beit Ha'Emek), 2 mM L-glutamine (Beit Ha'Emek)]. Cells from individual donors were incubated separately in tissue culture flasks (Corning, Acton, Mass.) at 37° C. (5% $CO_2$) with weekly change of culture media. Cells were split every 3-4 days using 0.25% trypsin-EDTA (Beit Ha'Emek). Following 2-40 passages, when reaching 60-80% confluence, cells were collected for analysis or for culturing in bioreactors.

Placenta derived adherent cells—Inner parts of a full-term delivery placenta (Bnei Zion medical center, Haifa, Israel) were cut under sterile conditions, washed 3 times with Hank's Buffer and incubated for 3 hours at 37° C. with 0.1% Collagenase (1 mg/ml tissue; Sigma-Aldrich, St. Lewis, Mo.). Using gentle pipetting, suspended cells were then washed with DMEM supplemented with 10% FCS, Pen-Strep-Nystatin mixture (100 U/ml:100 µg/ml:1.25 un/ml) and 2 mM L-glutamine, seeded in 75 cm$^2$ flasks and incubated at 37° C. in a tissue culture incubator under humidified condition with 5% $CO_2$. Thereafter, cells were allowed to adhere to a plastic surface for 72 hours after which the media was changed every 3-4 days. When reaching 60-80% confluence (usually 10-12 days), cells were detached from the growth flask using 0.25% trypsin-EDTA and seeded into new flasks. Cultured cells were thereafter collected for analysis or for culturing in bioreactors.

Adipose derived adherent cells—Adherent cells were obtained from human adipose tissue of liposuction procedures (Rambam Haifa, Israel). Adipose tissue was washed extensively with equal volumes of PBS and digested at 37° C. for 30 minutes with collagenase (20 mg/ml). Cells were then washed with DMEM containing 10% FCS, Pen-Strep-Nystatin mixture (100 U/ml:100 µg/ml:1.25 un/ml) and L-Glutamin and centrifuged at 1200 rpm for 10 minutes at room temperature (RT), resuspended with lysing solution (1:10; Biological Industries, Beit Ha'emek, Israel, in order to discard red-blood cells) centrifuged and resuspended with DMEM containing 10% FCS, Pen-Strep-Nystatin mixture (100 U/ml:100 µg/ml:1.25 un/ml) and L-Glutamin. Washed cells were then seeded in a sterile tissue culture medium flask at 3-10×10$^7$ cells/flask. At the next day cells were washed with PBS to remove residual RBC and dead cells. The cells were kept at 37° C. in a tissue culture incubator under humidified condition with 5% $CO_2$. The medium was changed every 3 to 4 days. At 60-80% confluence, the cells were detached from the growth flask using 0.25% trypsin-EDTA and seeded into new flasks. Following 2-40 passages, when cells reached 60-80% confluence, cells were collected for analysis or for culturing in bioreactors.

Figures 1A, 1B, 1C, 1D, 1E, 1F:
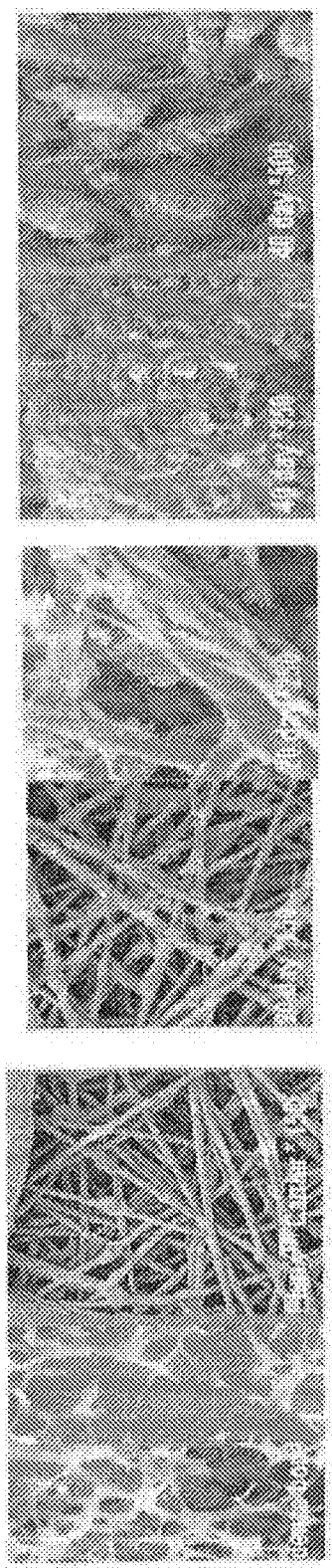
FIGS. 1A-G depict the bone-like microenvironment created in the bioreactor system containing 3-D carriers.
Figure 1G:
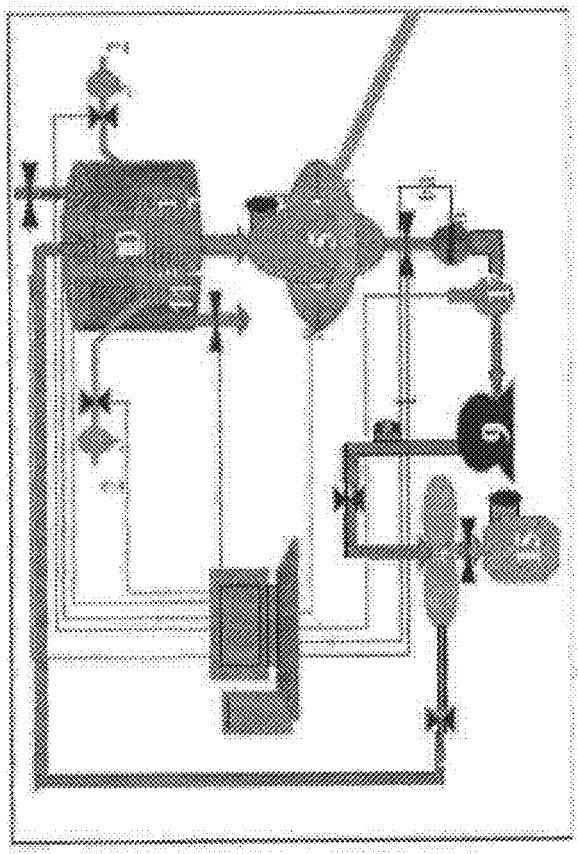

PluriX™ Plug Flow bioreactor—The PluriX™ Plug Flow bioreactor (Pluristem, Haifa, Israel; as illustrated in FIG. 1G, see also U.S. Pat. No. 6,911,201), was loaded with 1-100 ml packed 3D porrosive carriers (4 mm in diameter) made of a non woven fabric matrix of polyester. These carriers enable the propagation of large cell numbers in a relatively small volume. Glassware was designed and manufactured by Pluristem (Pluristem, Haifa, Israel). The bioreactor was maintained in an incubator of 37° C., with flow rate regulated and monitored by a valve (6a in FIG. 1G), and peristaltic pump (9 in FIG. 1G). The bioreactor contains a sampling and injection point (4 in FIG. 1G), allowing the sequential seeding of cells. Culture medium was supplied at pH 6.7-7.4 from a reservoir (1 in FIG. 1G). The reservoir was supplied by a filtered gas mixture (2, 3 in FIG. 10), containing air/$CO_2$/$O_2$ at differing proportions, depending on cell density in the bioreactor. The $O_2$ proportion was suited to the level of dissolved Oz at the bioreactor exit, determined by a monitor (6 in FIG. 1G). The gas mixture was supplied to the reservoir via silicone tubes or diffuser (Degania Bet, Emek Hayarden, Israel). The culture medium was passed through a separating container (7 in FIG. 1G) which enables collection of circulating, nonadherent cells. Circulation of the medium was obtained by a peristaltic pump (9 in FIG. 1G). The bioreactor was further equipped with an additional sampling point (10 in FIG. 1G) and containers for continuous medium exchange.

Production of 3D-adherent cells—Non-confluent primary human adherent 2D cell cultures, grown as described above, were trypsinized, washed, resuspended in DMEM supplemented with 10% FBS, Pen-Strep-Nystatin mixture (100 U/ml:100 ug/ml:1.25 un/ml) and 2 mM L-glutamine, and seeded ($10^3$-$10^5$ cells/ml) via an injection point onto the 3D carriers in a sterile Plug Flow bioreactor (see FIG. 1G). Prior to inoculation, bioreactor was filled with PBS—Ca—Mg (Biological Industries, Beit Ha'emek, Israel), autoclaved (120° C., 30 min) and washed with Dulbecco's growth medium containing 10% heat-inactivated fetal calf serum and a Pen-Strep-Nystatin mixture (100 U/ml:100 ug/ml:1.25 un/ml). Flow was kept at a rate of 0.1-5 mL/min. Seeding process involved cease of circulation for 2-48 hrs, thereby allowing the cells to settle on the carriers. Bioreactor was kept under controlled temperature (37° C.) and pH conditions (pH=6.7-7.4); using an incubator supplied with sterile air and $CO_2$ as needed. Growth medium was replaced 2-3 times a week. Circulation medium was replaced with fresh DMEM media, every 4 hr to 7 days. At a density of $1\times10^6$-$1\times10^7$ cells/ml (following 12-40 days of growth), total medium volume was removed from the bioreactor and bioreactor and carriers were washed 3-5 times with PBS. 3D-adherent cells were then detached from the carriers with Trypsin-EDTA; (Biological Industries, Beit Ha'emek, Israel; 3-15 minutes with gentle agitation, 1-5 times), and were thereafter resuspended in DMEM and cryopreserved.

3D-adherent cell quality biological assays—Cryopreserved 3D-adherent cells were thawed and counted. For cell viability evaluation, $2\times10^5$ cells were seeded in a 150 $cm^2$ tissue culture flask and their adherence capability and repopulation was evaluated within 7 days following seeding. Thereafter, the 3D-adherent cell membrane marker phenotype was analyzed using fluorescence monoclonal antibodies flow-cytometer (Beckman Coulter, Fullerton, Calif.).

Comparison between the cell membrane marker profile of 3D and 2D cultured adherent cells using flow cytometry assays 100,000-200,000 adherent cells from 2D cultures and 3D flow system cultures were suspended in 0.1 ml of culture medium in a 5 ml tube and incubated (4° C., 30 minutes, dark conditions) with saturating concentrations of each of the following MAbs: FITC-conjugated anti-human CD90 (Chemicon International Inc. Temecula, Calif.), PE conjugated anti human CD73 (Bactlab Diagnostic, Ceasarea, Israel), PE conjugated anti human CD105 (eBioscience, San Diego, Calif.), FITC conjugated anti human CD29 (eBioscience, San Diego, Calif.), Cy7-PE conjugated anti-human CD45 (eBiosience), PE-conjugated anti-human CD19 (IQProducts, Groningen, The Netherlands), PE conjugated anti human CD14 MAb (IQProducts), FITC conjugated anti human CD11b (IQProducts) and PE conjugated anti human CD34 (IQProducts) or with FITC conjugated anti human HLA-DR MAb (IQProducts). Following incubation the cells were washed twice in ice-cold PBS containing 1% heat-inactivated FCS, resuspended in 500 µl formaldehyde 0.5% and analyzed using the FC-500 flow-cytometer (Beckman Coulter, Fullerton, Calif.).

Comparison between the protein profile of 3D and 2D cultured adherent cells using mass spectrometry analysis—2D and 3D derived culturing procedures adherent cells were produced from the placenta as described above. Briefly, the 2D cultures were produced by culturing 0.3-0.75$\times10^6$ cells in 175 $cm^2$ flasks for 4 days under humidified 5% $CO_2$ atmosphere at 37° C., until reaching 60-80% confluence. The 3D cultures were produced by seeding 2-10$\times10^6$ cells/ gram in a bioreactor containing 2000 carriers, and culturing for 18 days. Following harvesting, cells were washed ($\times3$) to remove all the serum, pelleted and frozen. Proteins were isolated from pellets [using Tri Reagent kit (Sigma, Saint Louis, USA) and digested with trypsin and labeled with iTRAQ reagent (Applied Biosciences, Foster City, Calif.)], according to the manufacturers protocol. Briefly, iTRAQ reagents are non-polymeric, isobaric tagging reagents. Peptides within each sample are labeled with one of four isobaric, isotope-coded tags via their N-terminal and/or lysine side chains. The four labeled samples are mixed and peptides are analyzed with mass spectrometry. Upon peptide fragmentation, each tag releases a distinct mass reporter ion; the ratio of the four reporters therefore gives relative abundances of the given peptide in a sample. (information at: www.docs.appliedbiosystens.com/pebiodocs/00113379.pdf).

Proteomics analysis of 2D culture versus 3D culture of placenta derived adherent cells was performed in the Smoler proteomic center (department of Biology, Technion, Haifa, Israel) using LC-MS/MS on QTOF-Premier (Waters, San Francisco, Calif.), with identification and analysis done by Pep-Miner software [Beer, I., et al., Proteomics, 4, 950-60 (2004)] against the human part of the nr database. The proteins analyzed were: heterogeneous nuclear ribonucleoprotein H (Hnrph1 GenBank Accession No. NP_005511), H2A histone family (H2AF, GenBank Accession No. NP_034566.1), eukaryotic translation elongation factor 2 (EEEF2, GenBank Accession No. NP_031933.1), reticulocalbin 3, EF-hand calcium binding domain (RCN2. GenBank Accession No. NP_065701), CD44 antigen isoform 2 precursor (GenBank Accession No. NP 001001389, calponin 1 basic smooth muscle (CNN1, GenBank Accession No. NP 001290), 3 phosphoadenosine 5 phosphosulfate synthase 2 isoform a (Papss2, GenBank Accession No. NP_004661), ribosomal protein L7a (rpL7a, GenBank Accession No. NP_000963) and Aldehyde dehydrogenase X (ALDH X, GenBank Accession No. P47738). Every experiment was done twice. Because of the nature of the analysis, every protein was analyzed according to the number of peptides of which appeared in a sample (2-20 appearances of a protein in each analysis)

Comparison between secreted proteins in 3D and 2D cultured adherent cells using ELISA—2D and 3D derived culturing procedures adherent cells produced from the placenta, were produced as described above, with 3D cultures for the duration of 24 days. Conditioned media were thereafter collected and analyzed for Flt-3 ligand, IL-6, Thrombopoietin (TPO) and stem cell factor (SCF), using ELISA (R&D Systems, Minneapolis, Minn.), in three independent experiments. Results were normalized for $1\times10^6$ cells/ml.

Osteoblast differentiating medium—Osteogenic differentiation was assessed by culturing of cells in an osteoblast differentiating medium consisting DMEM supplemented with 10% FCS, 100 nM dexamethasone, 0.05 mM ascorbic acid 2-phosphate, 10 mM B-glycerophosphate, for a period of 3 weeks. Calcified matrix was indicated by Alizzarin Red S staining and Alkaline phosphatase was detected by Alkaline phosphatase assay kit (all reagents from Sigma-Aldrich, St. Lewis, Mo.).

Experimental Results

The PluriX™ Bioreactor System creates a physiological-like microenvironment.

In order to render efficient culture conditions for adherent cells, a physiological-like environment (depicted in FIG. 1A) was created artificially, using the PluriX Bioreactor (Pluristem, Haifa, Israel; carrier is illustrated in FIG. 1G and shown before seeding in FIG. 1B). As is shown in FIGS. 1C-F, bone marrow produced 3D-adherent cells were cultured successfully and expanded on the 3D matrix, 20 days (FIGS. 1B-C, magnified ×150 and 250 respectively) and 40 days (FIGS. 1C-D, magnified ×350 and 500 respectively) following seeding.

Figure 2:
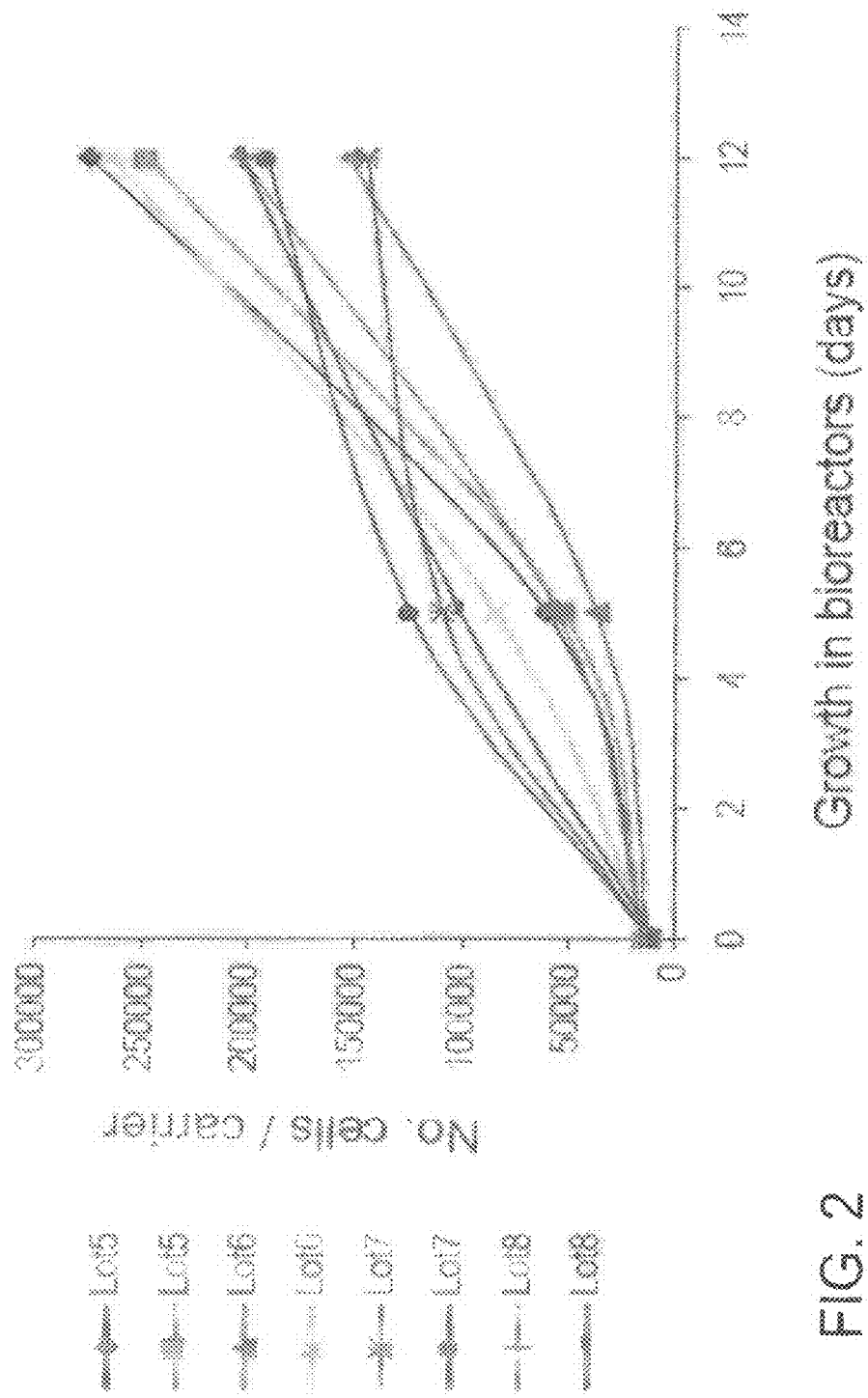
FIG. 2 is a graph depicting different production lots of adherent cells (Lots 5-8) originating from placenta, grown in 3D growth conditions within the bioreactor systems. Adherent cells ($2 \times 10^6$) were seeded in the bioreactor at a density of 10000-15000 cells/a carrier. Following a 12 day culture 3D-adherent cells reached a density of between 150,000-250,000 cells/carrier or $22.5$-$37.5 \times 10^6$ in a bioreactor containing 150 carriers.

Cells grown in the PluriX Bioreactor system were significantly expanded—Different production lots of placenta derived 3D-adherent cells were grown in the PluriX bioreactor systems. The seeding density was 13,300 cells/carrier (to a total of 2×10$^6$ cells). Fourteen days following seeding, cell density multiplied by 15 fold, reaching approximately 200,000 cells/carrier (FIG. 2), or 30×10$^6$ in a bioreactor of 150 carriers. In a different experiment, cells were seeded into the bioreactor at density of 1.5×10$^4$ cells/ml and 30 days following seeding the carriers contained an over 50-fold higher cell number, i.e. approx. 0.5×10$^6$ cells/carrier, or 0.5×10$^7$ cells/ml. The cellular density on the carriers at various levels of the growth column was consistent, indicating a homogenous transfer of oxygen and nutrients to the cells. The 3D culture system was thus proven to provide supporting conditions for the growth and prolonged maintenance of high-density mesenchymal cells cultures, which can be grown efficiently to an amount sufficient for the purpose of supporting engraftment and successful transplantation.

Figure 3A:
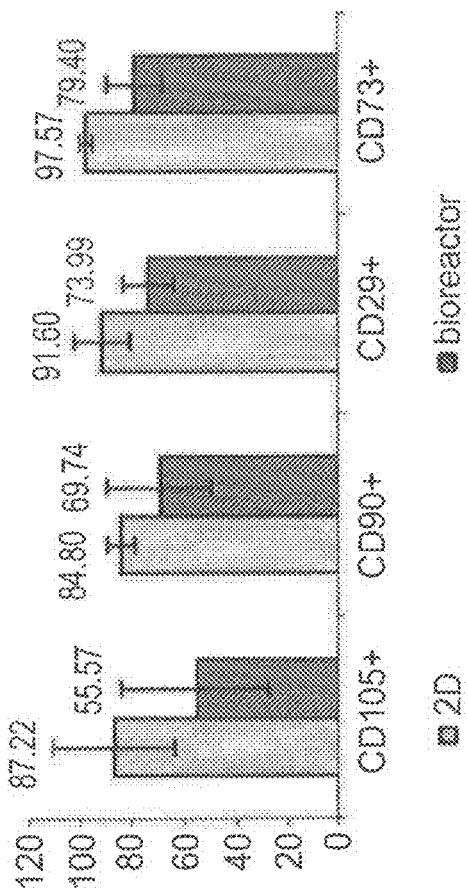
FIGS. 3A-B are bar graphs depicting difference in expression levels of expressed membrane markers in placenta derived 3D-adherent cell (dark purple) as compared to membrane markers in placenta cells cultured in conventional 2D culture conditions (light purple). Adherent cells were grown for 4-6 weeks in flasks (2D) or for 2-3 weeks in the bioreactor system, on polystyrene carriers (3D). Following harvesting from either flasks or carriers, cells were incubated and bound to a panel of monoclonal antibodies (MAb), which recognize membrane markers characteristic of adherent cells (FIG. 3A), or hematopoietic cells (FIG. 3B). Note the significantly higher expression of MSC membrane markers in 2D cultured cells as shown for CD90, CD105, CD73 and CD29 membrane markers, compared to MSC membrane markers expressed in 3D-cultured adherent cells, especially CD 105 which showed 56% expression in 3D cultured cells vs. 87% in the 2D cultured cells (FIG. 3A). Adherent cells of both 2D and 3D cultures, did not express any hematopoietic membrane markers (FIG. 3B).
Figure 3B:

3D-adherent cells show unique membrane marker characteristics—In order to define the difference in the secretion profile of soluble molecules and protein production, effected by the bone environment mimicking 3D culturing procedure, FACs analysis was effected. As is shown in FIG. 3A, FACS analysis of cell markers depict that 3D-adherent cells display a different marker expression pattern than adherent cells grown in 2D conditions. 2D cultured cells expressed significantly higher levels of positive membrane markers CD90, CD105, CD73 and CD29 membrane markers as compared to 3D cultured cells. For example, CD105 showed a 56% expression in 3D cultured cells vs. 87% in 2D cultured cells. Adherent cells of both 2D and 3D placenta cultures, did not express any hematopoietic membrane markers (FIG. 3B).

Figure 4A:
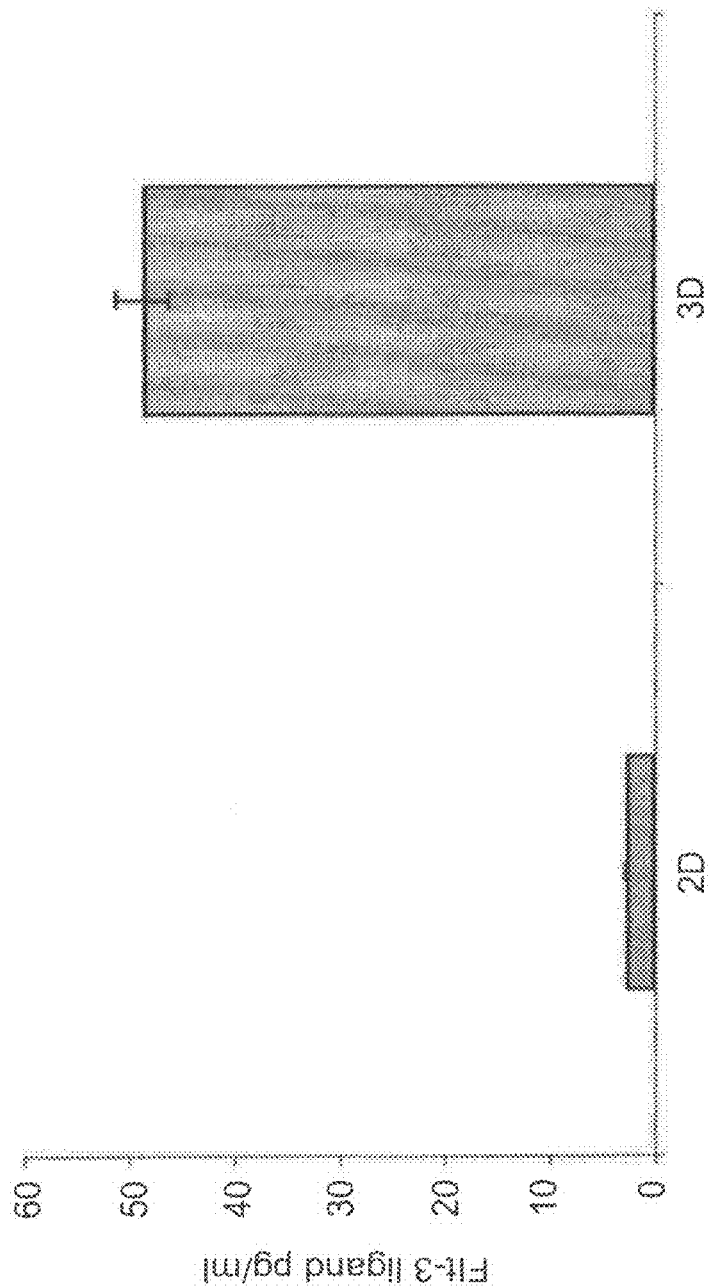

3D-adherent cells show a unique profile of soluble factors—The hematopoietic niche includes supporter cells that produce an abundance of cytokines, chemokines and growth factors. In order to further define the difference between 2D and 3D cultured adherent cells, the profile of the four main hematopoietic secreted proteins in the conditioned media of 2D and 3D adherent cell cultures was effected by ELISA. FIGS. 4A-C show that cells grown in 3D conditions produced condition media with higher levels of Flt-3 ligand (FIG. 4A), IL-60 (FIG. 4B), and SCF (FIG. 4C), while low levels of IL-6, and close to zero level of Flt-3 ligand and SCF, were detected in the condition media of 2D cultures. Production of Trombopoietin (TPO) was very low and equal in both cultures.

Figure 4D:
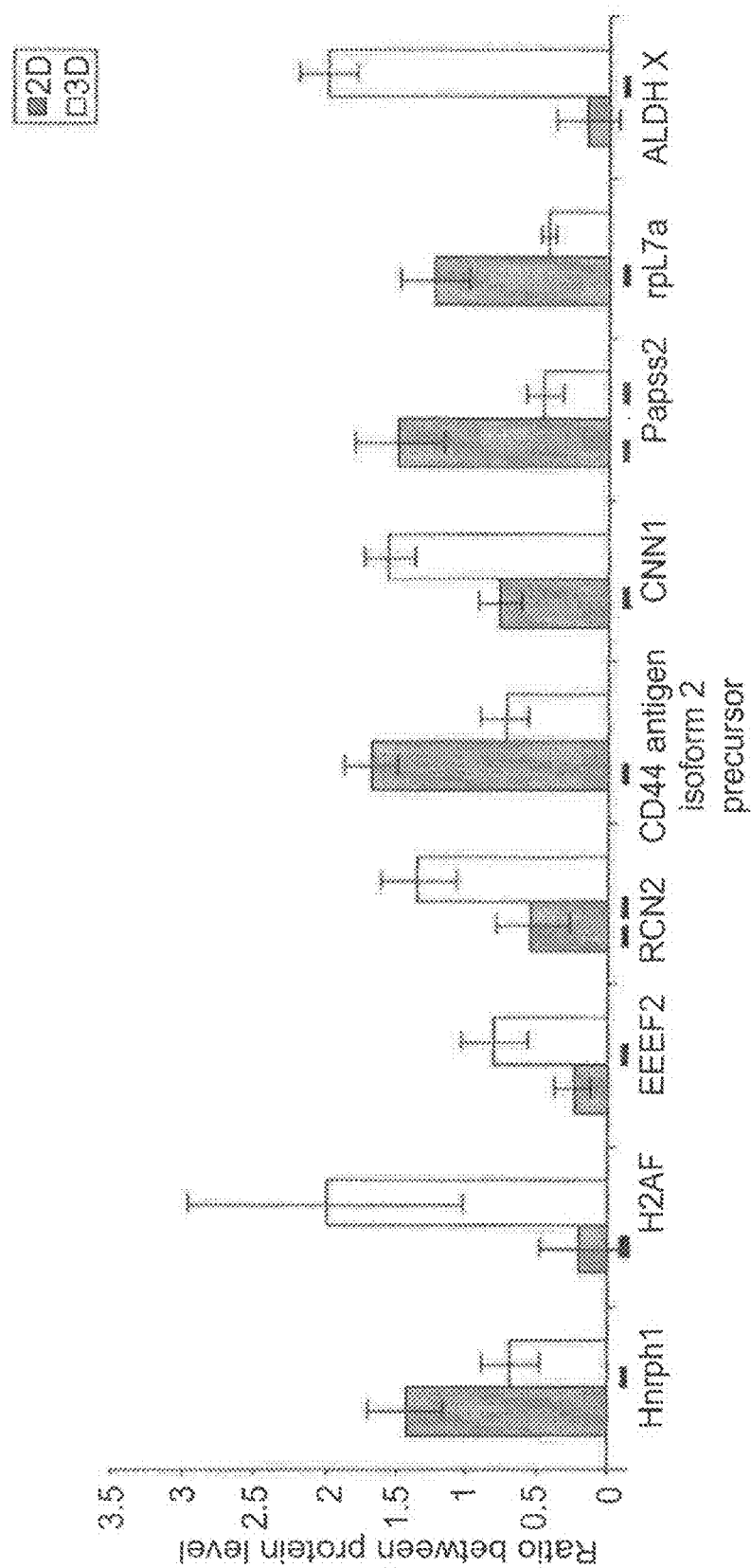

3D-adherent cells show a unique protein profile in mass spectrometry analysis—In order to further define the difference between 2D and 3D cultured adherent cells, the protein profile of these cells was analyzed by mass spectrometry. FIG. 4D shows that 2D and 3D cultured adherent cells show a remarkably different protein expression profile. As is shown in Table 1 below, 3D cultured cells show a much higher expression level of H2AF and ALDH X (more than 9 and 12 fold higher, respectively) and a higher level of the proteins EEEF2, RCN2 and CNN1 (ca. 3, 2.5 and 2 fold, respectively). In addition, 3D cultured cells show ca. half the expression levels of the proteins Hnrph1 and CD44 antigen isoform 2 precursor and ca. a third of the expression levels of Papss2 and rpL7a.

TABLE 1

| | Protein level (relative to iTRAQ reporter group) | | | |
| | 2D cultured adherent cells | | 3D cultured adherent cells | |
| protein | Av | SD | Av | SD |
| --- | --- | --- | --- | --- |
| Hnrph1 | 1.434493 | 0.260914 | 0.684687 | 0.197928 |
| H2AF | 0.203687 | 0.288058 | 1.999877 | 0.965915 |
| EEEF2 | 0.253409 | 0.130064 | 0.799276 | 0.243066 |
| RCN2 | 0.54 | 0.25 | 1.34 | 0.26 |
| CD44 antigen isoform 2 precursor | 1.68 | 0.19 | 0.73 | 0.17 |
| CNN1 | 0.77 | 0.15 | 1.55 | 0.17 |
| Papss | 1.48352 | 0.314467 | 0.45627 | 0.137353 |
| rpL7a | 1.22 | 0.24 | 0.43 | 0.05 |
| ALDH X | 0.15847 | 0.22411 | 1.986711 | 0.212851 |

Figure 5C:
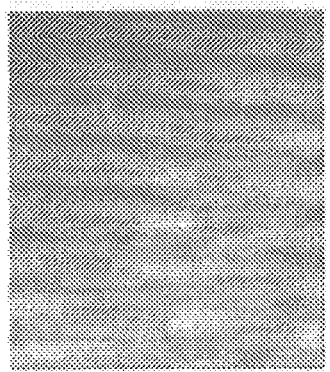
FIGS. 5A-D are micrographs depicting in vitro differentiation capability of placenta derived 3D-adherent cell to osteoblasts. Human placenta derived adherent cell were cultured in an osteogenic induction medium (DMEM containing 10% FCS, 100 nM dexamethasone, 0.05 mM ascorbic acid 2-phosphate, 10 mM B-glycerophosphate) for a period of 3 weeks.
Figure 5D:
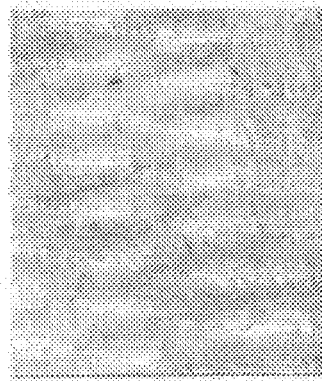
Figure 5A:
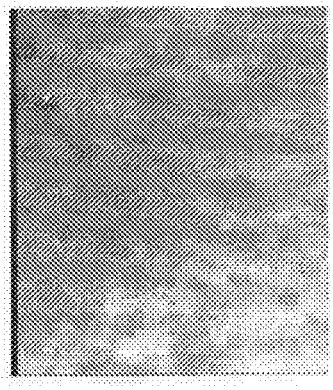
Figure 5B:
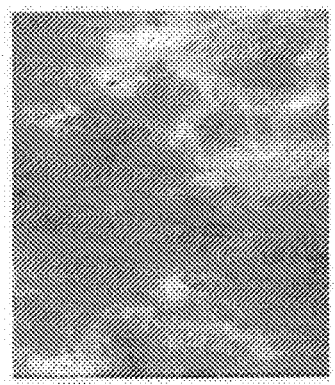

3D-adherent cells have the capacity to differentiate into osteoblasts—In order to further characterize 3D-adherent cells, cells were cultured in an osteoblast differentiating medium for a period of 3 weeks. Thereafter, calcium precipitation was effected. Differentiated cells were shown to produce calcium (depicted in red in FIGS. 5A-B) whereas control cells maintained a fibroblast like phenotype and demonstrated no mineralization (FIGS. 5C-D). These results show that placenta derived 3D-adherent cells have the capacity to differentiate in vitro to osteoblasts cells. 15

Example 2

Assessment of the Ability of Placenta Derived 3D-Adherent Cells to Improve HSC Engraftment 3D-adherent cell's support of HSC engraftment was evaluated by the level of human hematopoietic cells (hCD45+) detected in sub lethally irradiated or chemotherapy pretreated immune deficient NOD-SCID mice.

Materials and Experimental Procedures

Isolation of CD34+Cells—Umbilical cord blood samples were taken under sterile conditions during delivery (Bnei Zion Medical Center, Haifa, Israel) and mononuclear cells were fractionated using Lymphoprep (Axis-Shield PoC As, Oslo, Norway) density gradient centrifugation and were cryopreserved. Thawed mononuclear cells were washed and incubated with anti-CD34 antibodies and isolated using midi MACS (Miltenyi Biotech, Bergish Gladbach, Germany). Cells from more than one sample were pooled for achieving the desired amount (50,000-100,000 cells).

Detection of transplanted cells in irradiated mice—Seven week old male and female NOD-SCID mice (NOD-CB17-Prkdcscid/J; Harlan/Weizmann Inst., Rehovot Israel) were maintained in sterile open system cages, given sterile diets and autoclaved acidic water. The mice were sub lethally irradiated (350 cGy), and thereafter (48 hr post irradiation) transplanted with 50,000-100,000 hCD34$^+$ cells, with or without additional adherent cells ($0.5 \times 10^6$-$1 \times 10^6$) derived from placenta or adipose tissue (3-7 mice in each group), by intravenous injection to a lateral tail vein. Four to six weeks following transplantation the mice were sacrificed by dislocation and BM was collected by flushing both femurs and tibias with FACS buffer (50 ml PBS, 5 ml FBS, 0.5 ml sodium azid 5%). Human cells in the mice BM were detected by flow cytometry, and the percentage of the human and murine CD45 hematopoictic cell marker expressing cells in the treated NOD-SCID mice was effected by incubating cells with anti-human CD45-FITC (IQ Products, Groningen, The Netherlands). The lowest threshold for unequivocal human engraftment was designated at 0.5%.

Detection of transplanted cells in mice treated with chemotherapy—6.5 week old male NOD-SCID mice (NOD.CB17/JhkiHsd-scid; Harlan, Rehovot Israel), maintained as described hereinabove for irradiated mice, were injected intraperitoneally with Busulfan (25 mg/kg—for 2 consecutive days). Two days following the second Busulfan injection, mice were injected with CD34+ cells alone, or together with $0.5 \times 10^6$ adherent cells, produced from the placenta. 3.5 weeks following transplantation, mice were sacrificed, and the presence of human hematopoietic cells was determined as described hereinabove for irradiated mice.

Experimental Results 3D-adherent cells improved engraftment of HSC in irradiated mice—Human CD34+ hematopoietic cells and 3D-adherent cells derived from placenta or adipose tissues were co-transplanted in irradiated NOD-SCID mice. Engraftment efficiency was evaluated 4 weeks following co-transplantation, and compared to mice transplanted with HSC alone. As is shown in Table 2, co-transplantation of 3D-adherent cells and UCB CD34+ cells resulted in considerably higher engraftment rates and higher levels of human cells in the BM of recipient mice compared to mice treated with UCB CD34+ cells alone.

TABLE 2

| Transplanted cells | Average h-CD45 | STDEV |
| --- | --- | --- |
| CD34 | 3.8 | 7.9 |
| CD34 + 3D-adherent cells from placenta | 5.1 | 12.2 |
| CD34 + 3D-adherent cells from adipose | 8.7 | 9.6 |

Figure 6:
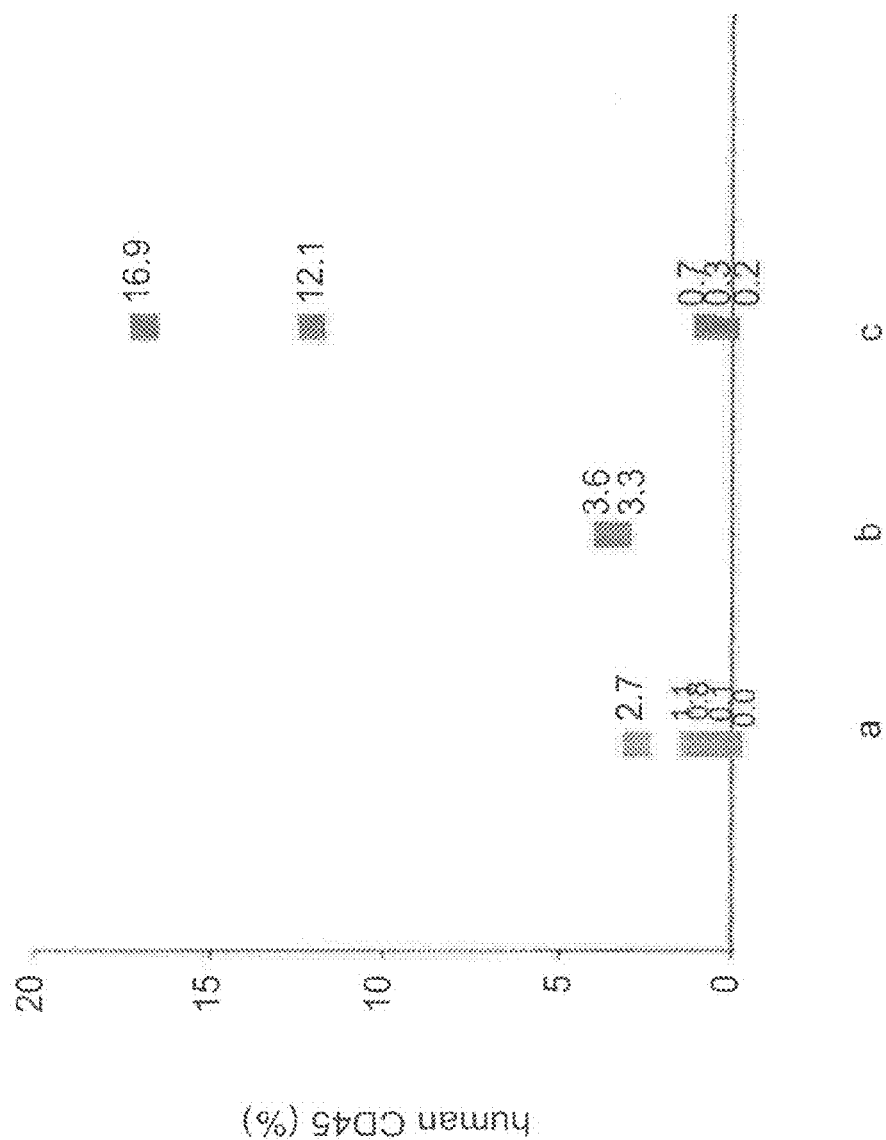
FIG. 6 is a graph depicting percentage of human CD45+ cells detected in bone marrow (BM) of NOD-SCID mice, treated with chemotherapy (25 mg/kg busulfan intraperitoneal injections for two consecutive weeks) 3.5 weeks following transplantation. CD34+ cells (100,000) purified from mononuclear cord blood derived cells, were transplanted alone (5 mice, a) or co-transplanted with $0.5 \times 10^6$ placenta derived adherent cells cultured in 2D conditions (2D-adherent cell; 2 mice, b), or placenta derived adherent cells cultured in 3D conditions (3D-adherent cell), in the pluriX™ bioreactor (5 mice, c). BM was then collected from mice femurs and tibias. Human cells in the BM were detected by flow cytometry. The percentage of CD45 expressing human cells was determined by incubating cells with anti-human CD45-FITC. Note the higher percentage of human cells (hCD45+) in the bone marrow of mice co-transplanted with 2D-adherent cell (b) as well as with 3D-adherent cell (c) in comparison to the percentage of human cells in the mice treated with HSCs alone (a). The higher engraftment seen in mice treated with 3D-adherent cell cultured cells in comparison to mice treated with 2D-adherent cell cultured cells indicates a higher therapeutic advantage unique to 3D cultured adherent cells.

3D-adherent cells improved engraftment of HSC in mice treated with chemotherapy—Human CD34+ hematopoietic cells were co-transplanted with 500,000-2D-adherent cells or 3D-adherent cells derived from placenta, into NOD-SCID mice pretreated with chemotherapy. Engraftment efficiency was evaluated 3.5 weeks following co-transplantation, and compared to mice transplanted with HSC alone. As is shown in Table 3 and FIG. 6, co-transplantation of adherent cells and UCB CD34+ cells resulted in higher engraftment levels in the BM of the recipient mice compared to UCB CD34-+ cells alone. Moreover, as is shown in Table 3, the average level of engraftment was higher in mice co-transplanted with placenta derived adherent cells grown in the PluriX bioreactor system (3D-adherent cells) than in the mice co-transplanted with cells from the same donor, grown in the conventional static 2D culture conditions (flask).

TABLE 3

| Transplanted cells | Average h-CD45 | STDEV |
| --- | --- | --- |
| CD34 | 0.9 | 1.1 |
| CD34 + conventional 2D cultures from placenta | 3.5 | 0.7 |
| CD34 + 3D-adherent cell from placenta | 6.0 | 7.9 |

Figures 7A, 7B:
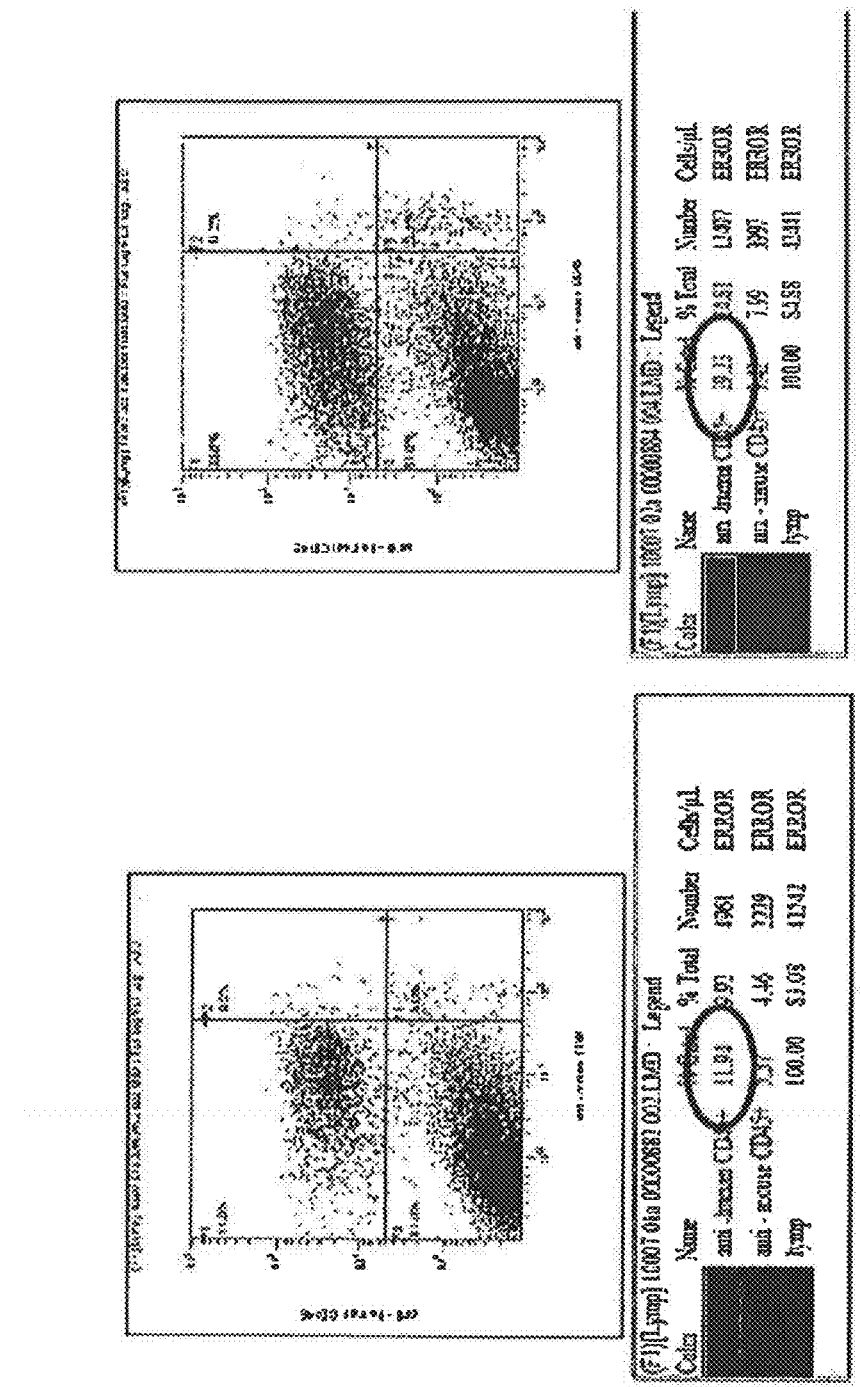
FIGS. 7A-B are FACS analyses of human graft CD45+ cells in mice transplanted with CD34+ cells only (FIG. 7A) in comparison to CD34+ cells together with adipose tissue derived adherent cells (FIG. 7B). Note the significantly higher percentage of human hematopoietic population (hCD45+) (7A-29%) in a mouse co-transplanted with adipose tissue derived adherent cell in comparison to a mouse treated with human CD34+ alone (7B-12%).

FACS analysis results shown in FIGS. 7A-B demonstrate the advantage of co-transplanting adherent cells with hHSCs (FIG. 7B), and the ability of adherent cells to improve the recovery of the hematopoietic system following HSC transplantation.

Taken together, these results show that adherent cells may serve as supportive cells to improve hematopoietic recovery following HSCs transplantation (autologous or allogenic). The ability of the 3D-adherent cells to enhance hematopoietic stem and/or progenitor cell engraftment following HSCs transplantation may result from the 3D-adherent cell ability to secrete HSC supporting cytokines that may improve the homing, self-renewal and proliferation ability of the transplanted cells, or from the ability of those cells to rebuild the damaged hematopoietic microenvironment needed for the homing and proliferation of the transplantable HSCs Example 3

The Suppression of Lymphocyte Response by 2D and 3D Cultured Adherent Cells

Adherent cells, and particularly 3D-adherent cells, were found to suppress the immune reaction of human cord blood mononuclear cells in an MLR assay Materials and Experimental Procedures Mixed lymphocyte reaction (MLR) assay—The immunosuppressive and immunoprivilaged properties of 2D and 3D derived culturing procedures adherent cells produced from the placenta, were effected by the MLR assay, which measures histocompatibility at the HLA locus, as effected by the proliferation rate of incompatible lymphocytes in mixed culturing of responsive (proliferating) and stimulating (unproliferative) cells. Human cord blood (CB) mononuclear cells ($2 \times 10^5$) were used as responsive cells and were stimulated by being co-cultured with equal amounts ($10^5$) of irradiated (3000 Rad) human peripheral blood derived Monocytes (PBMC), or with 2D or 3D cultured adherent cells, produced from the placenta, or a combination of adherent cells and PBMCs. Each assay was replicated three times. Cells were co-cultured for 4 days in RPMI 1640 medium (containing 20% FBS under humidified 5% $CO_2$ atmosphere at 37° C.), in a 96-well plate. Plates were pulsed with 1 μC $^3$H-thymidine during the last 18 hours of culturing. Cells were then harvested over fiberglass filter and thymidine uptake was quantified with a scintillation counter.

Experimental Results

Figure 8A:
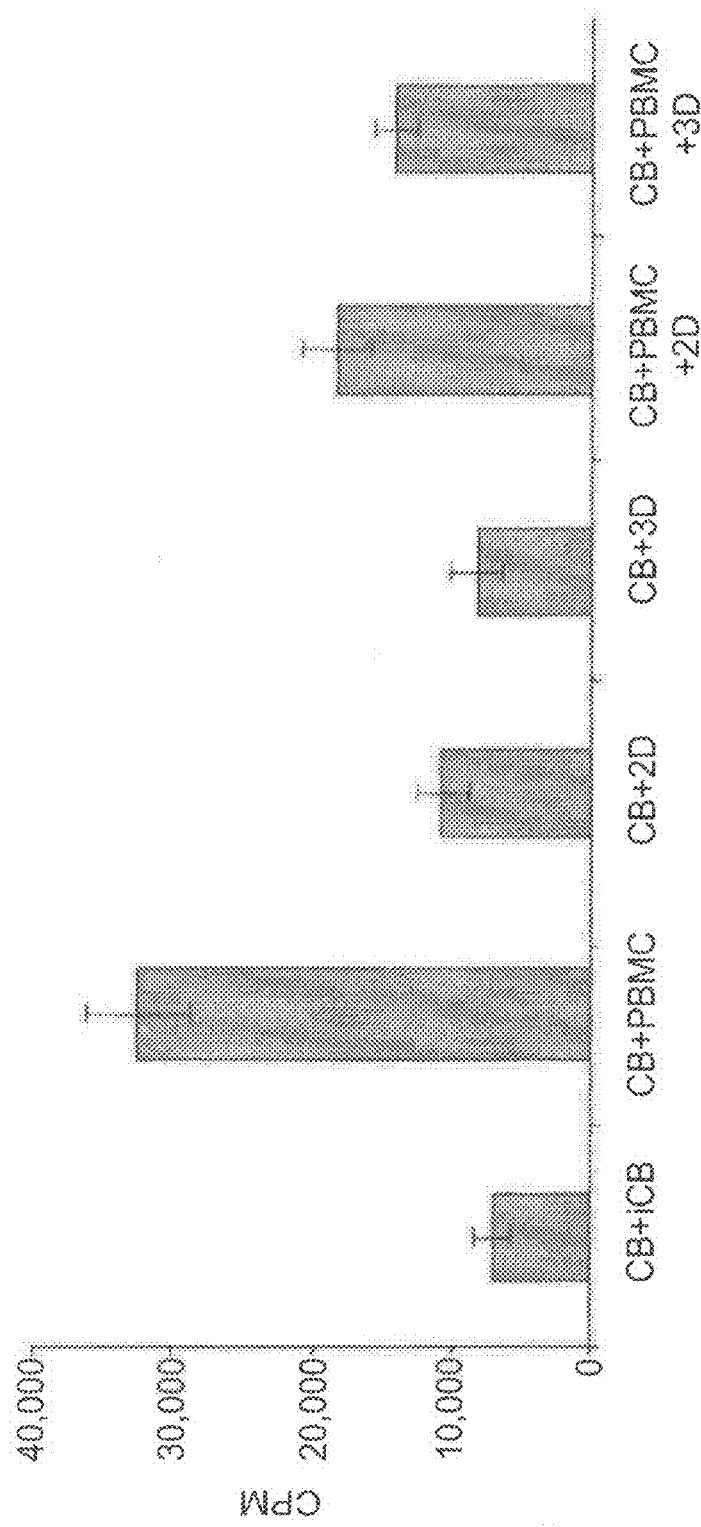
FIG. 8A is a bar graph depicting a mixed lymphocyte reaction conducted between human cord blood mononuclear cells (CB), and equal amounts of irradiated (3000 Rad) cord blood cells (iCB), human peripheral blood derived monocytes (PBMC), 2D cultured (2D) or 3D cultured (3D) placental derived adherent cells, or a combination of PBMC and 2D and 3D cultured placental derived adherent cells (PBMC+2D and PBMC+3D). Size of CB cell population is represented by the $^3$H-thymidine uptake (measured in CPM) which was measured during the last 18 hours of culturing. Elevation in stimulated CB cell proliferation indicates an immune response of a higher level. Note the lower level of immune response exhibited by cells incubated with adherent cells, and, in particular, the reduction of CB immune response to PBMCs when co-incubated with adherent cells. Three replicates were made of each reaction.

FIG. 8A shows the immune response of CB cells as represented by the elevated proliferation of these cells when stimulated with PBMCs, which, without being bound by theory, is probably associated with T cell proliferation in response to HLA incompatibility. However, a considerably lower level of immune response was exhibited by these cells when incubated with the adherent cells of the invention.

Moreover, the CB immune response to PBMCs was substantially reduced when co-incubated with these adherent cells. Thus, in a similar manner to MSCs, adherent cells were found to have the potential ability to reduce T cell proliferation of donor cells, typical of GvHD. Although both cultures, 2D and 3D, reduced the immune response of the lymphocytes, and in line with the other advantages of 3D-adherent cells described hereinabove, the 3D adherent cells were more immunosuppressive.

Example 4

3D Adherent Cells Manufactured by PluriX Compared to 3D Adherent Cells Manufactured by Celligen In order to provide large scale 3D adherent cells, a new manufacturing system was utilized referred to herein as Celligen.

Materials and Experimental Methods

PluriX™ Plug Flow bioreactor—As described in Example 1, hereinabove.

Production of 3D-adherent cells by Plurix (PLX cells)—As described in Example 1, hereinabove.

Figure 8B:
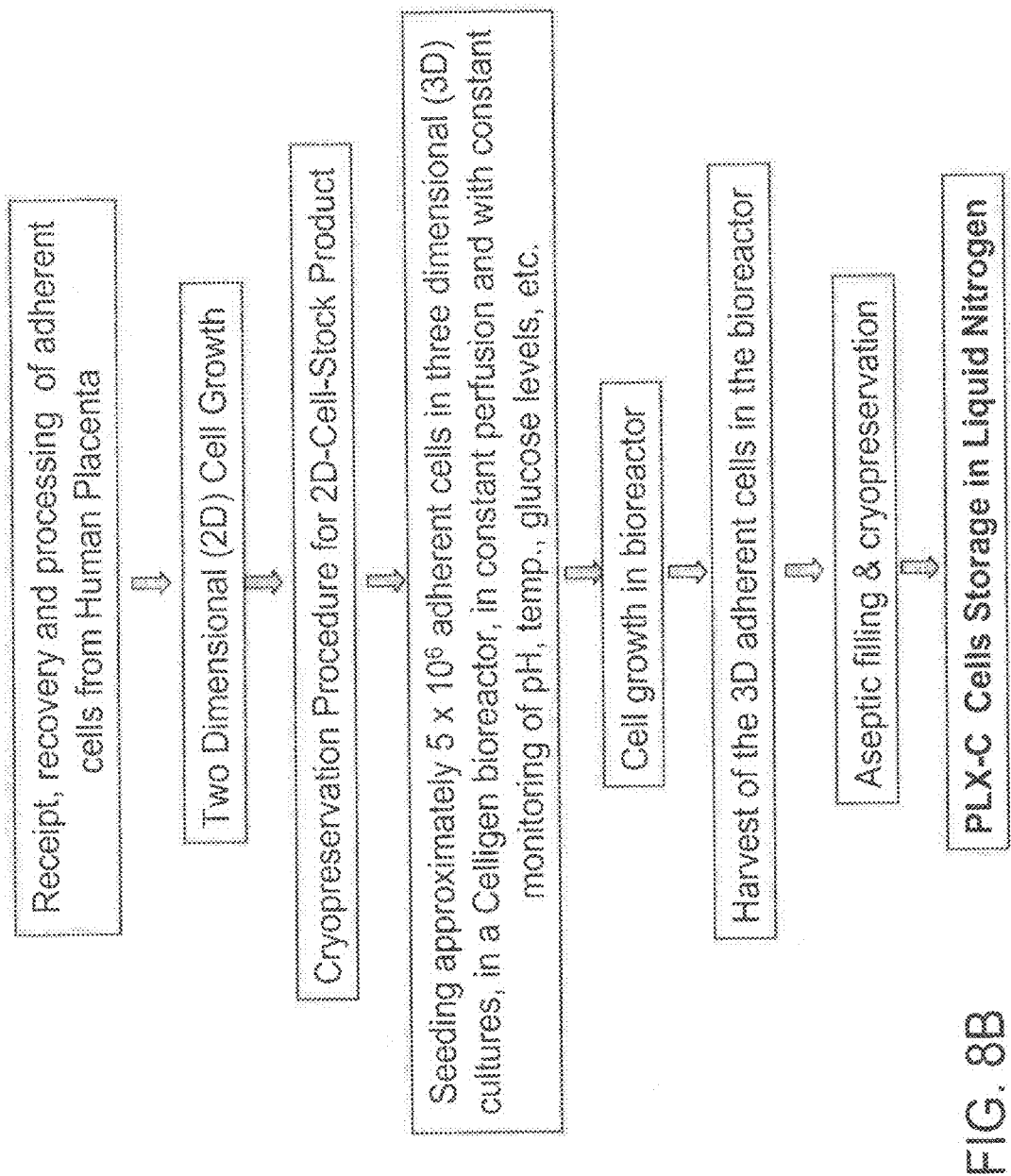
FIG. 8B is a flow chart depicting production of 3D adherent cell from placentas by Celligen™ (designated PLX-C cells).

Celligen™ Plug Flow bioreactor—The production of adherent cells by Celligen™ (PLX-C cells) is composed of several major steps as illustrated in FIG. 8B. The process starts by collection of a placenta from a planned cesarean delivery at term.

Adherent cells are then isolated from whole placentas, grown in tissue culture flasks (2D cultures), harvested and stored in liquid nitrogen as 2D-Cell Stock (2DCS), the appropriate amount of 2DCS are thawed, washed and seeded onto carriers in bioreactors for further expansion as 3D-culture. After 1-3 weeks of growth in the bioreactors, cells are harvested and cryopreserved in gas phase of liquid nitrogen as PLX-C.

Receipt of Human Tissue

All placentas obtained were received from the maternity ward under approval of the Helsinki Committee of the medical facility. Accordingly, all placenta donors signed an informed consent and Donor Screening and Donor Testing was performed (IPC1). Immediately after taking the placenta from the donor (during the caesarean procedure), it was placed in a sterile plastic bag and then in a Styrofoam box with ice packs. The placenta was delivered and immediately placed in a quarantine area until released to use by Quality Control (QC) and Quality Assurance (QA). All the following production steps were performed in a quarantine, clean room facility until QC approval of *mycoplasma* test results arrived and the cells were release for 2D cell growth.

Recovery and Processing of Adherent Cells

To initiate the process, the whole placenta was cut into pieces under aseptic conditions under laminar flow hood, washed with Hank's buffer solution and incubated for 3 hours at 37° C. with 0.1% Collagenase (1 mg Collagenase/ml tissue). 2D cell medium (2D-Medium comprising DMEM supplemented with 10% FBS, fungizone 0.25 µg/ml and gentamycine 50 µg/ml) was added and the digested tissue was roughly filtered through a sterile metal strainer, collected in a sterile beaker and centrifuged (10 minutes, 1200 RPM, 4° C.). Using gentle pipetting, suspended cells were then washed with 2D-Medium supplemented with antibiotics, seeded in 80 cm$^2$ flasks and incubated at 37° C. in a tissue culture incubator under humidified condition supplemented with 5% $CO_2$. Following 2-3 days, in which the cells were allowed to adhere to the flask surface, they were washed with PBS and 2D-Medium was added.

Two Dimensional (2D) Cell Growth

Prior to the first passage, growth medium samples of 10% of the total flask number in quarantine was pooled and taken for *mycoplasma* testing (IPC2). If cells were found to be negative for *Mycoplasma* (FZ-PCR *Mycoplasma* kit, Biological Industries, Israel), cells were released from quarantine. After 1-2 additional passages, cells were transferred to the 2D production clean room (2DP). Once in Room 2DP, culture was continued for another 3-5 passages. IPC-3 sample was taken for immune phenotype after passage 4. Throughout the process, cultures were grown in 2D-Medium without antibiotics in a tissue culture incubator under humidified conditions with 5% CO2 at 37° C. After a total of 6-8 passages (9-16 cell doublings), cells were collected and cryopreserved as the 2D-Cell Stock (2DCS).

The first passage was usually carried out after 10-15 days. Beginning at passage 2 and continuing until passage 6-8, cells were passaged when the culture reached 70-80% confluence, usually after 3-5 days (1.5-2 doublings). The cells were detached from the flasks using 0.25% trypsin-EDTA (4 minutes at 37° C.) and seeded in a culture density of $3\pm0.2\times10^3$ cells/cm$^2$. The size of the tissue culture flasks raised as the passages proceed. The culturing process started in 80 cm$^2$ tissue culture flask, continued in 175 cm$^2$, then in 500 cm$^2$ (Triple flask) and finally the cells were seeded into Cell Factory 10 tray (6320 cm$^2$).

Prior to cryopreservation, at the end of 2DCS growth period, the growth medium was collected and the sample was prepared to be sent to an approved GLP laboratory for *Mycoplasma* test (IPC 4).

Cryopreservation Procedure for 2D-Cell-Stock Product

For 2DCS cryopreservation, 2D-cultured cells were collected under aseptic conditions using 0.25% trypsin-EDTA. The cells were centrifuged (1200 RPM, 10', 4° C.), counted and re-suspended in 2D-Medium.

For freezing, cell suspensions were diluted 1:1 with 2D-Freezing Mixture (final concentrations was 10% DMSO, 40% FBS and 50% 2D-Medium). Approximately $1.5$-$2.5\times10^9$ cells were manufactured from one placenta. 4 ml of the cells were stored at a final concentration of $10\times10^6$, ml in 5 ml cryopreservation polypropylene vials. The vials were labeled and transferred to a controlled rate freezer for a graduated temperature reducing process (1° C./min), after which they were transferred to storage in gas-phase of a liquid nitrogen freezer located in the Cold Storage Room. This material was referred to as the 2D-Cell Stock (2DCS) batch.

Initiation of the Three Dimensional (3D) Culture Procedures

To begin 3D culture, an appropriate amount ($150\pm30\times10^6$) of cells from 2DCS were thawed in the 2DP room and washed with 3D-Medium (DMEM with 10% FBS and 20 Mm Hepes) to remove DMSO prior to seeding in the prepared-in-advanced bioreactor systems. The content of each 2DCS vial was pipetted and diluted 1:9 with pre-warmed (37° C.) 3D-Medium. The cells were centrifuged (1200 RPM, 10', 4° C.) and re-suspended again in 50-100 ml pre-warmed (37° C.) 3D-Medium in a 250 ml sterile bottle. A sample was taken and cells were counted using a Trypan Blue stain in order to determine cell number and viability. The cell suspension was transferred under a laminar flow hood into a 0.5 L seeding bottle. From the seeding bottle the cell suspension was transferred via sterile tubing to the bioreactor by gravitation.

Production of 3D-adherent Cells in the Celligen Bioreactor (PLX-C)

Bioreactor Description 3D growth phase was performed using an automatic CelliGen Plus® or BIOFLO 310 bioreactor system [(New Brunswick Scientific (NBS)] depicted in FIG. 8C. The bioreactor system was used for cultivation of cell culture, in which conditions were suitable for high cell concentrations. The cultivation process was carried out using a bioreactor in a perfusion mode. The lab scale bioreactor was constructed of two main systems—the control system and the bioreactor itself (vessel and accessories). The parameters of the process were monitored and controlled by a control console which included connectors for probes, motor and pumps, control loops for Dissolved Oxygen (DO), pH, perfusion and agitation (with a motor), a gases control system, water circulation and heating system for temperature control and an operator interface. The controlled process parameters (such as temperature, pH, DO etc.) could be displayed on the operator interface and monitored by a designated controller.

Cell Culture Growth Procedure in the Bioreactors

As noted in the section hereinabove, $150\pm30\times10^6$ cells from the cryopreserved 2DCS were thawed, washed and seeded in a sterile bioreactor. The bioreactor contained 30-50 gr carriers (FibraCel® disks, NBS), made of Polyester and Polypropylene and $1.5\pm0.1$ L 3D-Medium. The growth medium in the bioreactor was kept at the following conditions: 37° C., 70% Dissolved Oxygen (DO) and pH 7.3. Filtered gases (Air, $CO_2$, $N_2$ and $O_2$) were supplied as determined by the control system in order to keep the DO value at 70% and the pH value at 7.3. For the first 24 hours, the medium was agitated at 50 Rounds Per Minutes (RPM) and increased up to 200 RPM by day 2. For the first 2-3 days, the cells were grown in a batch mode. Perfusion was initiated when the medium glucose concentration decreased below 550 mg/liter. The medium was pumped from the feeding container to the bioreactor using sterile silicone tubing. All tubing connections were performed under laminar flow using sterile connectors. The perfusion was adjusted on a daily basis in order to keep the glucose concentration constant at approximately $550\pm50$ mg\liter. A sample of the growth medium was taken every 1-2 days for glucose, lactate, glutamine, glutamate and ammonium concentration determination (BioProfile 400 analyzer, Nova Biomedical). The glucose consumption rate and the lactate formation rate of the cell culture enabled to measure cell growth rate. These parameters were used to determine the harvest time based on accumulated experimental data.

Harvest of the 3D Grown PLX-X Cells from the Bioreactor

The cell harvest process started at the end of the growth phase (4-10 days). Two samples of the growth medium were collected. One sample was prepared to be sent to an approved GLP laboratory for *Mycoplasma* testing according to USP and Eu standards, and the other one was transferred to a controlled rate freezer for a graduated temperature reducing process (1° C./imin), after which they were transferred to storage in gas-phase of a liquid nitrogen freezer located in the Cold Storage Room, in case a repeat *Mycoplasma* testing was needed. These medium samples were considered as part of the *Mycoplasma* testing of the final product and the results were considered as part of the criteria for product release.

The 3D-grown culture was harvested in the Class-100 laminar area in room 3DP as follows:

The bioreactor vessel was emptied using gravitation via tubing to a waste container. The vessel was opened, by removing the head plate, and the carriers were aseptically transferred, using sterile forceps, from the basket to the upper basket net (see FIG. 8C). The bioreactor vessel was then closed and refilled with 1.5 L pre-warmed PBS (37° C.). The agitation speed was increased to 150 RPM for 2 minutes. The PBS was drained via tubing by pressure or gravity to the waste bottle. The washing procedure was repeated twice.

In order to release the cells from the carriers, 1.5 L pre-warmed to 37° C. Trypsin-EDTA (Trypsin 0.25%, EDTA 1 mM) was added to the bioreactor vessel and carriers were agitated for 5 minutes in 150 RPM, 37° C. Cell suspension was collected to a 5 L sterile container containing 250 ml FBS. Cell suspension was divided to 4 500 ml sterile centrifuge tubes and a *Mycoplasma* test sample was withdrawn. Closed centrifuge tubes were transferred through the 3DP active pass-through into the class 10,000 filling room (FRI) in which the cells were aseptically filled and cryopreserved as PLX-C.

Cell Cycle analysis—PLX-C cells obtained by Celligen and PLX cells obtained by Plurix were fixed with 70% EtOH O.N, centrifuged and re-suspended in a Propidium Iodide (PI) solution containing 2 μg/ml PI (Sigma), 0.2 mg/ml Rnase A (Sigma) and 0.1% (v/v) Triton (Sigma) for 30 minutes. Cell cycle was analyzed by FACS.

Gene expression array (Microarray)—Adherent cells were obtained from human full term placentas and were expanded Plurix or by Celligen. Three different batches of cells were obtained from each of the expansion methods for further examination.

RNA was extracted from the cells (Qiagen-Rneasy micro kit) and applied to an Affymetrix whole genome expression array. The chip used GeneChip® Human Exon 1.0 ST Array (Affymetrix, Santa Clara, Calif., USA).

FACS analysis of membrane markers—cells were stained with monoclonal antibodies as previously described. In short, 400,000-600,000 cells were suspended in 0.1 ml flow cytometer buffer in a 5 ml test tube and incubated for 15 minutes at room temperature (RT), in the dark, with each of the following monoclonal antibodies (MAbs): FITC-conjugated anti-human CD29 MAb (eBioscience), PE conjugated anti human CD73 MAb (Becton Dickinson), PE conjugated anti human CD105 MAb (eBioscience), PE conjugated anti human CD90 MAb (Becton Dickinson), FITC-conjugated anti-human CD45 MAb (IQProducts), PE-conjugated anti-human CD19 MAb (IQProducts), PE conjugated anti human CD14 MAb (IQProducts), FITC conjugated anti human HLA-DR MAb (IQProduct), PE conjugated anti human CD34 MAb (IQProducts), FITC conjugated anti human CD31 MAb (eBioscience), FITC conjugated anti human KDR MAb (R&D systems), anti human fibroblasts marker (D7-FIB) MAb (ACRIS) , , , FITC-conjugated anti-human CD80 MAb (BD), FITC-conjugated anti-human CD86 MAb (BD), FITC-conjugated anti-human CD40 MAb (BD), FITC-conjugated anti-human HLA-ABC MAb (BD), Isotype IgG1 FITC conjugated (IQ Products), Isotype IgG1 PE conjugated (IQ Products).

Cells were washed twice with flow cytometer buffer, resuspended in 500 μl flow cytometer buffer and analyzed by flow cytometry using FC-500 Flow Cytometer (Beckman Coulter). Negative controls were prepared with relevant isotype fluorescence molecules.

Mixed Lymphocyte Reaction (MLR)

$2\times10^5$ peripheral blood (PB) derived MNC (from donor A) were stimulated with equal amount of irradiated (3000 Rad) PB derived MNCs (from donor B). Increasing amounts of PLX-Cs were added to the cultures. Three replicates of each group were seeded in 96-well plates. Cells were cultured in RPMI 1640 medium containing 20% FBS. Plates were pulsed with 1 μC $^3$H-thymidine during the last 18 hrs of the 5-day culturing. Cells were harvested over a fiberglass filter and thymidine uptake was quantified with scintillation counter.

For CFSE staining, PB-MNC cells were stained for CFSE (Molecular Probes) for proliferation measurement before culturing. Cells were collected after 5 days and the intensity of CFSE staining was detected by Flow Cytometry.

ELISA

ELISA was carried out as was previously described. In short, MNCs (isolated from peripheral blood) were stimulated with 5 μg/ml ConA (Sigma), 0.5 μg/ml LPS (SIGMA), or 10 μg/ml PHA (SIGMA) in the presence of PLX-C under humidified 5% CO2 atmosphere at 37° C. Supernatants were collected and subjected to cytokine analysis using ELISA kits for IFNγ (DIACLONE), TNFα (DIACLONE) and IL-10 (DIACLONE).

Experimental Results

The changes in manufacturing with Celligen as compared to Plurix resulted in

TABLE 4

Comparison between Plurix system and Celligen system

| Parameter | Cell growth according to Example 1 | Teachings of the present invention | Improvement |
|---|---|---|---|
| Working volume (ml) | 280 | 1500 | Scale up of the process. Higher production level in the present teachings (2-8 population doubling) |
| Weight of carrier (gr) | 1.4 | 30 | Scale up of the process |
| Bed configuration | Conic, 50 ml column. | Cylinder Packed bed | Present teachings - Better flow of medium and nutrients. Teachings of Example 1 - Inefficient flow due to narrow outlet form of the conic structure Better homogeneity of medium flow. Channeling in the teachings of Example 1. |
| Cell concentration at seeding (cell/gr carrier) | 3 × 10$^6$ cell/gr carrier | 5 × 10$^6$ cell/gr carrier | Better cell to cell interaction in the present teachings |
| Cell concentration at seeding (cell/ml) | 0.015 × 10$^6$ cell/ml | 0.1 × 10$^6$ cell/ml | Better cell to cell interaction in the present teachings |
| Seeding procedure | Seeding at low medium volume for 24 h followed by addition of medium to final working volume | Seeding at the final working volume while agitating | Teachings of Example 1 - Heterogenic distribution of the cell culture inside the carrier bed. Insufficient medium volume in the first 24 h of the run. Leading to unsuitable working conditions (acidic environment) |

TABLE 4-continued

Comparison between Plurix system and Celligen system

| Parameter | Cell growth according to Example 1 | Teachings of the present invention | Improvement |
|---|---|---|---|
| Production phase duration | 14-21 days | 4-10 days | Better product quality. Efficient harvest process, Better yield. Lower cost process in the present teachings |
| Mode of operation | Repeated batch - medium change twice a week | Perfusion mode - rate was adjusted according to the glucose concentration (the medium was changed at glucose concentration of 550 ± 50 mg/L) | Present teachings - Moderate changes of the conditions regarding medium composition throughout the run Continuous removal of toxic agents produced by the cells. In batch mode - lower concentration of essential nutrients (limiting factors) Less cell debris |
| Harvest procedure | Harvesting in 50 ml tubes Trypsinization 3 cycles | Harvesting inside the bioreactor Trypsinization 1 cycle | Present teachings - More efficient process Harvest is carried out in a close system. 1 trypsinization cycle-better quality of the cells. |
| Agitation | medium Circulation between reservoir container to the column using peristaltic pump | Cell lift impeller | Present teachings - Medium is flowing through the packed bed-Better supply of nutrients and oxygen to the culture. Homogeneity of the medium Improves other control loops (temp., DO, pH) |
| Temperature control | The production was carried out inside an incubator. Indirect temperature control (of the incubator chamber). Heat transfer via air interface | On-line direct control. Heat transfer via water jacket. | Present teachings - More accurate measurement of the culture temperature. Quick response. Short time to reach set point. |
| Temperature monitoring | Manually. Indirect water temperature monitoring. | On-line direct monitoring | Present teachings - Better monitoring and control of the process. Quick response to malfunctions. |
| DO monitoring | None | On-line monitoring | Present teachings - Better monitoring and control of the process. Quick response to malfunctions |
| DO control | None. Introduction of air only | On-line direct control of a specific set point using Air, O$_2$ and N$_2$. | Present teachings - Better control of DO level. Better maintenance of a specified working conditions |

TABLE 4-continued

Comparison between Plurix system and Celligen system

| Parameter | Cell growth according to Example 1 | Teachings of the present invention | Improvement |
|---|---|---|---|
| pH monitoring and control | Only visual monitoring (Phenol red as part of the medium) | On-line Control and monitoring | Present teachings - Better control of pH level. Better maintenance of a specified working conditions |
| Aeration | Sparge only | Overlay (sparge as an option) | Teachings of Example 1 - Aeration by sparge creates foam that might damage the cells. |

The changes in the manufacturing process resulted in changes in characteristics of the obtained 3D adherent cells. These differences are summarized below.

Figure 9A:
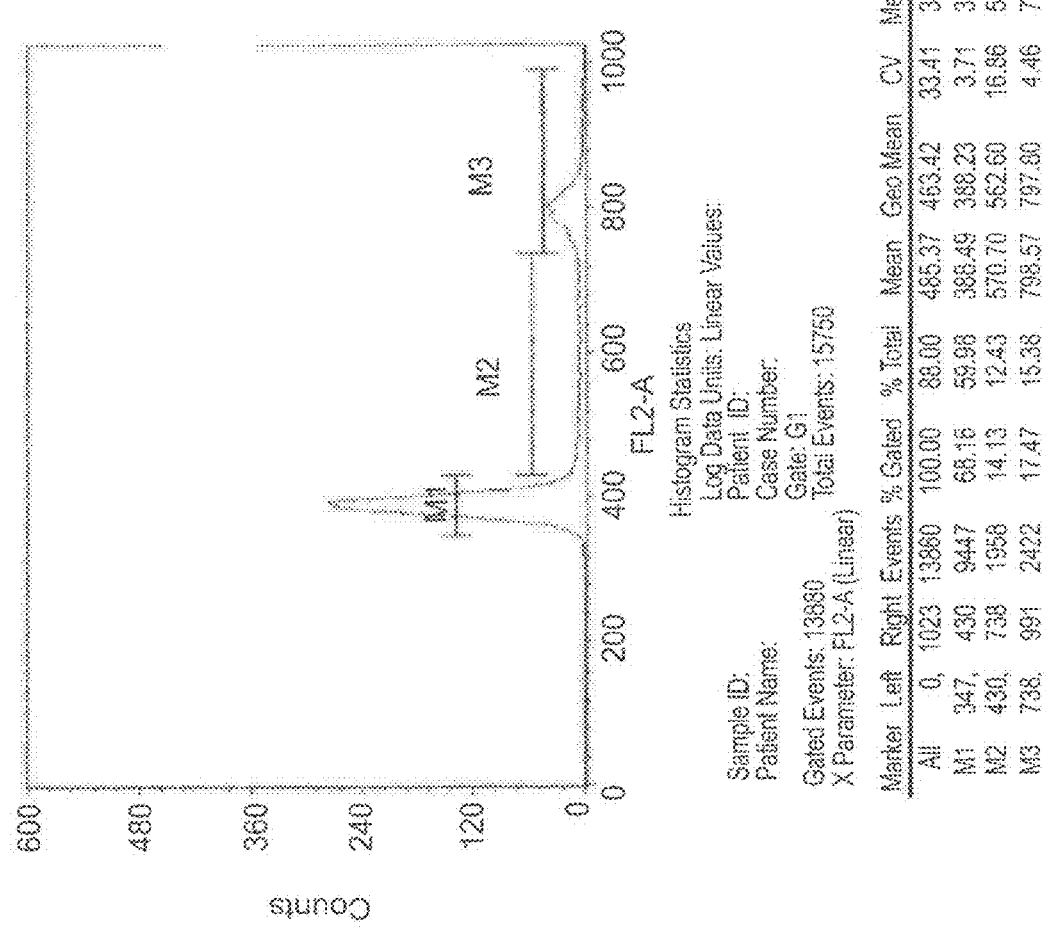
FIGS. 9A-B depict cell cycle analysis of 3D adherent cells manufacture by Plurix (designated PLX, FIG. 9B) and by Celligen (designated PLX-C, FIG. 9A). Cells were fixed in 70% EtOH O.N, centrifuged and re-suspended in a Propidium Iodide (PI) solution and then analyzed by FACS.
Figure 9B:
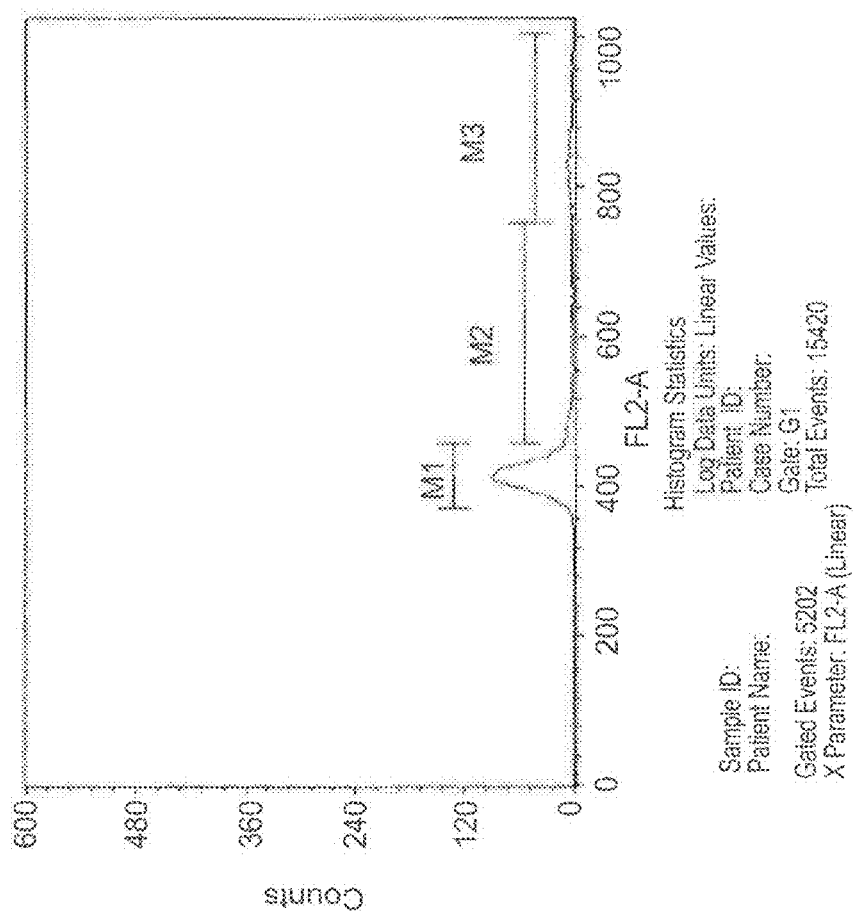

Cell cycle analysis of PLX manufactured by Plurix compared to PLX-C manufactured by Celligen—PLX-C cells obtained by Celligen were compared to PLX cells obtained by Plurix in order to examine the distribution of the cells between the different phases of the cell cycle. As is clear from FIGS. 9A-B, PLX-C cells expanded by Celligen exhibited typical proliferating profile (distribution of cells between the different phases of cell cycle). Specifically, 28% of cells were in S and G2/M phases (FIG. 9A). These results indicated that cells were harvested during proliferation and that the Celligen bioreactor conditions supported cell growth.

Microarray comparison between Plurix and Celligen obtained cells—gene expression arrays enabled to simultaneously monitor genome-wide expression profiles of adherent cells derived from human full term placentas expanded by Plurix (PLX) or by Celligen (PLX-C). These results enabled to asses the molecular mechanism underlying phenotypic variation between cells obtained by these different growth methods (see Table 5, below).

TABLE 5

Gene expression in Celligen compared to Plurix cells

| Gene | Celligen vs. Plurix (fold change) | p-value (treat) |
|---|---|---|
| interferon-induced protein with tetratricopeptide repeats | 17.52 | 0.0401812 |
| aldehyde dehydrogenase 1 family, member A1 | 16.76 | 0.00145807 |
| leukocyte-derived arginine aminopeptidase | 13.99 | 3.88E-06 |
| keratin 27 pseudogene 27 | 12.25 | 0.000224998 |
| similar to Keratin, type I cytoskeletal 18 | 11.83 | 0.000304949 |
| G protein-coupled receptor, family C, group 5, member A | 10.35 | 3.39E-05 |
| integrin, alpha 6 | 9.84 | 0.0411667 |
| G protein-coupled receptor 126 | 8.73 | 0.00197635 |
| coagulation factor III (thromboplastin, tissue factor) | 7.36 | 0.012192 |
| Rho GDP dissociation inhibitor (GDI) beta | 7.36 | 0.00200066 |
| signal peptide, CUB domain, EGF-like 3 | 7.20 | 0.0255115 |
| interferon-induced protein with tetratricopeptide repeats | 7.09 | 0.0139777 |
| dickkopf homolog 1 (*Xenopus laevis*) | 7.06 | 3.06E-07 |
| NAD(P)H dehydrogenase, quinone 1 | 6.63 | 0.000282423 |
| keratin 18 | 6.46 | 1.000514523 |
| opioid growth factor receptor-like 1 | 5.96 | 0.00114551 |
| mal, T-cell differentiation protein-like | 5.95 | 0.00664216 |
| neurofilament, medium polypeptide 150 kDa | 5.86 | 0.0190611 |
| DEP domain containing 1 | 5.82 | 0.000370513 |
| cathepsin C | 5.72 | 0.00512262 |
| WAS | 5.47 | 0.00178153 |
| serpin peptidase inhibitor, clade B (ovalbumin), member | 5.44 | 0.0190218 |
| solute carrier family 7, (cationic amino acid) | 5.33 | 0.00688017 |
| interferon-induced protein with tetratricopeptide | 5.18 | 0.00357376 |
| NUF2, NDC80 kinetochore complex component, homolog | 5.05 | 0.00276524 |
| SHC SH2-domain binding protein 1 | 4.95 | 0.00430878 |
| thioredoxin reductase 1 | 4.86 | 0.000197486 |
| lung cancer metastasis-associated protein | 4.85 | 0.00148024 |
| Rho GTPase activating protein 29 | 4.85 | 0.0466211 |
| cell division cycle 20 homolog (*S. cerevisiae*) | 4.80 | 0.00514206 |
| family with sequence similarity 111, member B | 4.63 | 0.000125819 |
| PDZ binding kinase | 4.54 | 0.00784983 |
| establishment of cohesion 1 homolog 2 (*S. cerevisiae*) | 4.53 | 0.000773033 |
| guanylate binding protein 4 | 4.47 | 0.000215944 |
| lipase A, lysosomal acid, cholesterol esterase (Wolman) | 4.42 | 0.0167385 |
| kinesin family member 20A | 4.39 | 0.00582352 |
| KIAA0101 | 4.28 | 0.0105909 |
| cyclin-dependent kinase inhibitor 3 (CDK2-associated dual | 4.25 | 0.000732492 |
| thymidylate synthetase | 4.23 | 0.00685584 |
| chromosome 13 open reading frame 3 | 4.18 | 0.000548296 |
| aurora kinase A | 4.16 | 0.00632571 |
| nei endonuclease VIII-like 3 (*E. coli*) | 4.14 | 0.00115606 |
| centrosomal protein 55 kDa | 4.13 | 0.0021952 |
| oxidized low density lipoprotein (lectin-like) receptor 1 | 4.11 | 0.0205198 |
| denticleless homolog (*Drosophila*) | 4.05 | 0.00141153 |

TABLE 5-continued

Gene expression in Celligen compared to Plurix cells

| Gene | Celligen vs. Plurix (fold change) | p-value (treat) |
|---|---|---|
| anillin, actin binding protein | 4.01 | 0.010923 |
| ribonucleotide reductase M2 polypeptide | 3.98 | 0.00834059 |
| ankyrin repeat domain 1 (cardiac muscle) | 3.93 | 0.00911953 |
| transcription factor 19 (SC1) | 3.89 | 0.00109627 |
| keratin 18 | 3.89 | 0.000112551 |
| non-SMC condensin I complex, subunit G | 3.88 | 0.00537097 |
| cyclin E2 | 3.87 | 0.00020189 |
| trypsinogen C | 3.86 | 0.00416276 |
| small nucleolar RNA, C | 3.81 | 0.0334484 |
| tight junction protein 2 (zona occludens 2) | 3.81 | 0.00012562 |
| kinesin family member 18A | 3.78 | 0.00134108 |
| kinesin family member 2C | 3.77 | 0.0059888 |
| shugoshin-like 1 (S. pombe) | 3.76 | 0.00101318 |
| polo-like kinase 1 (Drosophila) | 3.75 | 0.0140309 |
| thymidine kinase 1, soluble | 3.73 | 0.00124134 |
| transcription factor 19 (SC1) | 3.73 | 0.00124377 |
| transcription factor 19 (SC1) | 3.73 | 0.00124327 |
| claspin homolog (Xenopus laevis) | 3.71 | 0.00683624 |
| GINS complex subunit 1 (Psf1 homolog) | 3.69 | 0.00104515 |
| microsomal glutathione S-transferase 1 | 3.67 | 0.041701 |
| arylacetamide deacetylase-like 1 | 3.67 | 0.000902645 |
| SPC25, NDC80 kinetochore complex component, homolog | 3.65 | 0.00568662 |
| integrin, alpha 4 (antigen CD49D, alpha 4 subunit of VLA-4 | 3.62 | 0.0158411 |
| catenin (cadherin-associated protein), alpha-like 1 | 3.57 | 7.46E−05 |
| discs, large homolog 7 (Drosophila) | 3.56 | 0.0317074 |
| v-myb myeloblastosis viral oncogene homolog (avian) | 3.55 | 0.0043878 |
| serglycin | 3.54 | 0.0443487 |
| centromere protein N | 3.53 | 0.000540143 |
| cyclin A2 | 3.53 | 0.00965934 |
| heat shock 22 kDa protein 8 | 3.52 | 0.0219583 |
| senna domain, immunoglobulin domain (Ig), short basic doma | 3.49 | 0.008548 |
| Rho GTPase activating protein 11A | 3.49 | 0.00834174 |
| Fanconi anemia, complementation group I | 3.43 | 0.00464532 |
| BUB1 budding, uninhibited by benzimidazoles 1 homolog | 3.42 | 0.0108258 |
| ovary-specific acidic protein | 3.42 | 0.00334641 |
| cholinergic receptor, muscarinic 2 | 3.41 | 0.0320078 |
| cell division cycle 2, G1 to S and G2 to M | 3.41 | 0.0017111 |
| protein regulator of cytokinesis 1 | 3.39 | 0.0325664 |
| minichromosome maintenance complex component 5 | 3.38 | 0.00475504 |
| sperm associated antigen 5 | 3.37 | 0.00906321 |
| maternal embryonic leucine zipper kinase | 3.34 | 0.00908391 |
| small nucleolar RNA, C | 3.33 | 0.0298703 |
| carnitine palmitoyltransferase 1A (liver) | 3.33 | 0.00170894 |
| similar to Ubiquitin-conjugating enzyme E2S | 3.33 | 0.000415822 |
| kinesin family member 11 | 3.33 | 0.00915145 |
| NIMA (never in mitosis gene a)-related kinase 7 | 3.33 | 0.00159114 |
| ADAM metallopeptidase with thrombospondin type 1 motif, | 3.32 | 0.0102751 |
| transforming, acidic coiled-coil containing protein 3 | 3.31 | 0.0014577 |
| cyclin B1 | 3.29 | 0.0103092 |
| MAD2 mitotic arrest deficient-like 1 (yeast) | 3.28 | 0.00488102 |
| dihydrofolate reductase | 3.28 | 0.00178879 |
| NIPA-like domain containing 3 | 3.27 | 0.00164708 |
| cell division cycle associated 2 | 3.26 | 0.0122226 |
| apolipoprotein B mRNA editing enzyme, catalytic | 3.26 | 0.00308692 |
| cyclin B2 | 3.25 | 0.016544 |
| endonuclease domain containing 1 | 3.24 | 0.000429245 |
| dihydrofolate reductase pseudogene | 3.13 | 0.00141306 |
| ATPase, Na+ | 3.23 | 0.000381464 |
| replication factor C (activator 1) 3, 38 kDa | 3.23 | 0.00109668 |
| WD repeat domain 76 | 3.22 | 0.0023531 |
| pleckstrin 2 | 3.17 | 0.0304429 |
| Rac GTPase activating protein 1 | 3.17 | 0.00381613 |
| PHD finger protein 19 | 3.17 | 0.000177604 |
| deleted in lymphocytic leukemia, 2 | 3.15 | 0.0109528 |
| centromere protein I | 3.15 | 0.0106816 |
| BRCA1 associated RING domain 1 | 3.14 | 0.000540414 |
| regulator of 6-protein signalling 4 | 3.13 | 0.00781061 |
| STAM binding protein-like 1 | 3.11 | 0.0181743 |
| sulfiredoxin 1 homolog (S. cerevisiae) | 3.10 | 5.14E−05 |
| chromosome 15 open reading frame 23 | 3.08 | 0.000147331 |

TABLE 5-continued

Gene expression in Celligen compared to Plurix cells

| Gene | Celligen vs. Plurix (fold change) | p-value (treat) |
|---|---|---|
| TTK protein kinase | 3.08 | 0.0112171 |
| non-SMC condensin II complex, subunit G2 | 3.08 | 0.0130322 |
| villin 2 (ezrin) | 3.07 | 0.0131934 |
| stomatin | 3.06 | 0.00387095 |
| protein tyrosine phosphatase-like A domain containing | 3.06 | 0.0419644 |
| serpin peptidase inhibitor, clade B (ovalbumin), member | 3.05 | 0.0030439 |
| kinesin family member 4A | 3.05 | 0.0114203 |
| hypothetical protein DKFZp762E1312 | 3.05 | 0.00726778 |
| ubiquitin-conjugating enzyme E2S | 3.04 | 0.00118203 |
| hydroxysteroid dehydrogenase like 2 | 3.03 | 3.71E−05 |
| ATPase family, AAA domain containing 2 | 3.01 | 0.00415258 |
| TPX2, inierombule-associated, homolog (*Xenopus laevis*) | 3.00 | 0.0253137 |
| histone cluster 1, H4d | 3.00 | 0.030183 |
| kinesin family member 23 | 2.99 | 0.00790585 |
| heat shock 70 kDa protein 2 | 2.99 | 0.0215102 |
| origin recognition complex, subunit 1-like (yeast) | 2.99 | 0.00707751 |
| dihydrofolate reductase | 2.98 | 0.00307793 |
| hyaluronan-mediated motility receptor (RHAMM) | 2.97 | 0.00467816 |
| 3'-phosphoadenosine 5'-phosphosulfate synthase 2 | 2.97 | 1.43E−05 |
| glycerol-3-phosphate dehydrogenase 2 (mitochondrial) | 2.95 | 0.00211969 |
| nucleolar and spindle associated protein 1 | 2.95 | 0.00520875 |
| diaphanous homolog 3 (*Drosophila*) | 2.95 | 0.00107709 |
| kinesin family member 14 | 2.94 | 0.00947901 |
| histone cluster 1, H1b | 2.93 | 0.0470898 |
| guanine nucleotide binding protein (G protein), alpha inhi | 2.92 | 0.00184597 |
| minichromosome maintenance complex component 8 | 2.92 | 0.000841489 |
| cancer susceptibility candidate 5 | 2.92 | 0.0330594 |
| leukotriene B4 12-hydroxydehydrogenase | 2.92 | 0.000685452 |
| glutamate-cysteine ligase, modifier subunit | 2.91 | 0.00378868 |
| forkhead box M1 | 2.91 | 0.0203154 |
| adipose differentiation-related protein | 2.90 | 0.000331751 |
| membrane bound O-acyltransferase domain containing 1 | 2.90 | 0.01185 |
| ubiquitin-conjugating enzyme E2T (putative) | 2.90 | 0.00741886 |
| cell division cycle associated 3 | 2.89 | 0.006289 |
| integrin, alpha 3 (antigen CD49C, alpha 3 subunit of VLA-3 | 2.88 | 0.00574148 |
| coagulation factor XIII, B polypeptide | 2.88 | 0.0294465 |
| RAD51 homolog (RecA homolog, *E. coli*) (*S. cerevisiae*) | 2.87 | 0.000854719 |
| ATP-binding cassette, sub-family C (CFTR | 2.87 | 0.00382491 |
| family with sequence similarity 29, member A | 2.85 | 0.00111165 |
| SH2 domain containing 4A | 2.84 | 0.0323646 |
| membrane protein, palmitoylated 1, 55 kDa | 2.84 | 0.000396285 |
| CDC28 protein kinase regulatory subunit 1B | 2.84 | 0.0107391 |
| PSMC3 interacting protein | 2.84 | 0.00766442 |
| elastin microfibril interfacer 2 | 2.84 | 0.0192072 |
| topoisomerase (DNA) II alpha 170 kDa | 2.83 | 0.0321109 |
| transmembrane protein 106C | 2.82 | 0.000214223 |
| histone cluster 1, H3b | 2.80 | 0.0304598 |
| chromosome 18 open reading frame 24 | 2.80 | 0.00347442 |
| epidermal growth factor receptor pathway substrate 8 | 2.79 | 0.0194949 |
| high-mobility group nucleosomal binding domain 2 | 2.78 | 0.0030536 |
| SCL | 2.78 | 0.00390288 |
| hect domain and RLD 4 | 2.78 | 0.00679184 |
| AST1 anti-silencing function 1 homolog B (*S. cerevisiae*) | 2.77 | 0.00543408 |
| thyroid hormone receptor interactor 13 | 2.76 | 0.118319 |
| cell division cycle associated 8 | 2.75 | 0.00619878 |
| kinesin family member C1 | 2.74 | 0.00821937 |
| high-mobility grow nucleosomal binding domain 2 | 2.73 | 0.00384071 |
| ornithine decarboxylase 1 | 2.73 | 0.00144868 |
| v-myb myeloblastosis viral oncogene homolog (avian)-like 2 | 2.71 | 0.00989416 |
| KIT ligand | 2.70 | 0.00641955 |
| dual-specificity tyrosine-(Y)-phosphorylation regulated | 2.70 | 0.0234606 |
| intraflagellar transport 80 homolog (*Chlamydomonas*) | 2.70 | 0.0247286 |
| transmembrane protein 48 | 2.69 | 0.00458248 |
| EBNA1 binding protein 2 | 2.69 | 0.00296292 |
| ZW10 interactor | 2.69 | 1.88E−05 |
| exonuclease 1 | 2.68 | 0.00739393 |
| transketolase (Wernicke-Korsakoff syndrome) | 2.68 | 1.92E−05 |
| somatostatin receptor 1 | 2.68 | 0.0144901 |
| isocitrate dehydrogenase 3 (NAD+) alpha | 2.67 | 0.00297129 |
| cytoskeleton associated protein 2 | 2.67 | 0.0030499 |
| minichromosome maintenance complex component 4 | 2.67 | 0.00342054 |

TABLE 5-continued

Gene expression in Celligen compared to Plurix cells

| Gene | Celligen vs. Plurix (fold change) | p-value (treat) |
|---|---|---|
| inhibitor of DNA binding 1, dominant negative helix-loop-hel | 2.66 | 0.036485 |
| CDC28 protein kinase regulatory subunit 1B | 2.66 | 0.0145263 |
| keratin 18 | 2.66 | 8.40E−05 |
| CD97 molecule | 2.66 | 0.00994045 |
| chromosome 6 open reading frame 173 | 2.64 | 0.00222408 |
| BTB (POZ) domain containing 3 | 2.62 | 0.0166824 |
| deafness, autosomal dominant 5 | 2.62 | 0.00235481 |
| KIAA0286 protein | 2.62 | 0.00130563 |
| Fanconi anemia, complementation group D2 | 2.61 | 0.0281405 |
| polo-like kinase 4 (Drosophila) | 2.60 | 0.00209633 |
| ribonucleotide reductase M1 polypeptide | 2.60 | 0.000170076 |
| malic enzyme 1, NADP(+)-dependent, cytosolic | 2.59 | 0.0435444 |
| non-SMC condensin I complex, subunit H | 2.59 | 0.0216752 |
| S100 calcium binding protein A3 | 2.58 | 0.0324073 |
| ubiquitin-conjugating enzyme E2L 3 | 2.57 | 0.00343347 |
| BUB1 budding uninhibited by benzimidazoles 1 homolog beta | 2.56 | 0.0166047 |
| glycerol kinase | 2.55 | 2.66E−05 |
| TAF9B RNA polymerase II, TATA box binding protein (TBP)-as | 2.54 | 0.0170365 |
| TAF9B RNA polymerase II, TATA box binding protein (TBP)-as | 2.54 | 0.0170365 |
| historic cluster 1, H2bg | 2.52 | 0.000180822 |
| high-mobility group box 2 | 2.52 | 0.0196872 |
| NIMA (never in mitosis gene a)-related kinase 2 | 2.50 | 0.00289469 |
| proline rich 11 | 2.50 | 0.0357125 |
| myopalladin | 2.49 | 0.0255088 |
| brix domain containing 1 | 2.49 | 0.00471977 |
| cell division cycle associated 5 | 2.49 | 0.01021 |
| fucosidase, alpha-L-2, plasma | 2.49 | 0.00540929 |
| cyclin-dependent kinase 2 | 2.49 | 0.00250724 |
| lamin B receptor | 2.49 | 0.000151784 |
| hypoxanthine phosphoribosyltransferase, 1 (Lesch-Nyhan | 2.49 | 0.000634057 |
| tripartite motif-containing 25 | 2.47 | 0.0456344 |
| proteasome (prosome, macropain) subunit, beta type, 9 | 2.46 | 0.0202595 |
| proteasome (prosome, macropain) subunit, beta type, 9 | 2.46 | 0.0202595 |
| proteasome (prosome, macropain) subunit, beta type, 9 | 2.46 | 0.0202595 |
| sphingomyelin synthase 2 | 2.46 | 0.0020701 |
| transmembrane protein 62 | 2.45 | 0.00761064 |
| glucose-6-phosphate dehydrogenase | 2.44 | 0.00278311 |
| PHD finger protein 1 | 2.44 | 0.010191 |
| retinoblastoma-like 1 (p107) | 2.44 | 0.00319946 |
| KIAA1524 | 2.43 | 0.0380688 |
| ST6 (alpha-N-acetyl-neuraminyl-2,3-beta-galactosyl-1, | 2.43 | 0.00830766 |
| cofilin 2 (muscle) | 2.43 | 0.0459235 |
| hypothetical protein LOC201725 | 2.42 | 0.000313319 |
| cell division cycle 25 homolog A (S. pombe) | 2.42 | 0.000341692 |
| breast cancer 1, early onset | 2.41 | 0.0180553 |
| transaldolase 1 | 2.41 | 0.00199537 |
| mRNA turnover 4 homolog (S. cerevisiae) | 2.41 | 0.00373104 |
| glucosaminyl (N-acetyl) transferase 1, core 2 (beta-1,6-N- | 2.41 | 0.0197148 |
| cysteine rich transmembrane BMP regulator 1 (chordin-like) | 2.41 | 0.0267286 |
| tissue factor pathway inhibitor (lipoprotein-associated | 2.40 | 0.0356227 |
| chromosome 16 open reading frame 59 | 2.40 | 0.00185191 |
| glycogenin 1 | 2.39 | 0.0224317 |
| transmembrane protein 154 | 2.39 | 0.0045589 |
| tubulointerstitial nephritis antigen-like 1 | 2.39 | 0.00510812 |
| CTP synthase | 2.38 | 8.80E−05 |
| phenylalanyl-tRNA synthetase, beta subunit | 2.38 | 0.000243973 |
| geminin, DNA replication inhibitor | 2.38 | 0.00167629 |
| lamin B1 | 2.37 | 0.0477748 |
| SPC24, NDC80 kinetochore complex component, homolog | 2.36 | 0.00287227 |
| glutathione reductase | 2.36 | 0.00353875 |
| ribosomal protein L22-like 1 | 2.36 | 0.00335381 |
| fumarylacetoacetate hydrolase (fumarylacetoacetase) | 2.36 | 3.88E−05 |
| small nucleolar RNA, C | 2.35 | 0.0188991 |
| family with sequence similarity 64, member A | 2.35 | 0.0019785 |
| epithelial cell transforming sequence 2 oncogene | 2.35 | 0.000571152 |
| polymerase (DNA directed), epsilon 2 (p59 subunit) | 2.34 | 0.00479612 |
| glycerol kinase | 2.34 | 3.37E−06 |

TABLE 5-continued

Gene expression in Celligen compared to Plurix cells

| Gene | Celligen vs. Plurix (fold change) | p-value (treat) |
|---|---|---|
| glutathione S-transferase M2 (muscle) | 2.33 | 0.0402076 |
| elongation factor, RNA polymerase II, 2 | 2.33 | 0.0130017 |
| thioredoxin | 2.33 | 0.009636 |
| polymerase (DNA directed), alpha 2 (70 kD subunit) | 2.32 | 0.0033903 |
| breast cancer 2, early onset | 2.32 | 0.00586847 |
| CDC45 cell division cycle 45-like (S. cerevisiae) | 2.32 | 0.00735977 |
| H2A histone family member Z | 2.32 | 0.0129697 |
| transporter 1, ATP-binding cassette, sub-family B (MDR | 2.31 | 0.0164234 |
| transporter 1, ATP-binding cassette, sub-family B (MDR | 2.31 | 0.0164234 |
| transporter 1, ATP-binding cassette, sub-family B (MDR | 2.31 | 0.0164234 |
| nucleolar complex associated 3 homolog (S. cerevisiae) | 2.30 | 0.000371346 |
| ATPase, Ca++ transporting, plasma membrane 4 | 2.30 | 0.023011 |
| minichromosome maintenance complex component 7 | 2.30 | 0.0457691 |
| TIMELESS interacting protein | 2.29 | 0.00771062 |
| von Hippel-Lindau binding protein 1 | 2.28 | 0.00329061 |
| ras-related C3 botulinum toxin substrate 2 (rho family, sma | 2.28 | 0.0292466 |
| thymopoietin | 2.28 | 0.0223176 |
| peptidylprolyl isomerase F (cyclophilin F) | 2.28 | 0.00093846 |
| activated leukocyte cell adhesion molecule | 2.27 | 0.00242163 |
| polycomb group ring finger 5 | 2.27 | 0.000294142 |
| Ran GTPase activating protein 1 | 2.27 | 9.68E−05 |
| replication factor C (activator 1) 4, 37 kDa | 2.26 | 0.00164152 |
| tubulin, beta 2C | 2.26 | 0.000346744 |
| minichromosome maintenance complex component 10 | 2.26 | 0.0037925 |
| H2B histone family, member S | 2.25 | 0.000885505 |
| gamma-glutamyl hydrolase (conjugase, folylpolygammaglutamyl | 2.25 | 0.0195219 |
| transcription termination factor, RNA polymerase II | 2.25 | 0.000393489 |
| polymerase (DNA directed), delta 2, regulatory subunit 50 k | 2.25 | 0.0173873 |
| transporter 1, ATP-binding cassette, sub-family B (MDR | 2.25 | 0.00859077 |
| transporter 1, ATP-binding cassette, sub-family B (MDR | 2.25 | 0.00859077 |
| transporter 1, ATP-binding cassette, sub-family B (MDR | 2.25 | 0.00859077 |
| histone cluster 1, H2bf | 2.25 | 0.0124279 |
| eukaryotic translation initiation factor 1A, X-linked | 2.24 | 0.00330183 |
| phosphoglucomutase 2 | 2.24 | 0.00818204 |
| peroxisomal D3,D2-enoyl-CoA isomerase | 2.24 | 0.00148722 |
| interferon-induced protein with tetratricopeptide repeats | 2.24 | 0.0177928 |
| G-2 and S-phase expressed 1 | 2.23 | 0.0241887 |
| minichromosome maintenance complex component 2 | 2.23 | 0.0021347 |
| family with sequence similarity 72, member A | 2.23 | 0.00143248 |
| RMI1, RecQ mediated genome instability 1, homolog | 2.23 | 0.00294705 |
| FLJ20105 protein | 2.23 | 0.0127979 |
| multiple coagulation factor deficiency 2 | 2.22 | 0.0116892 |
| phytoceramidase, alkaline | 2.22 | 0.0157729 |
| coiled-coil domain containing 68 | 2.22 | 0.00227586 |
| dedicator of cylokinesis 11 | 2.21 | 0.00697577 |
| platelet-derived growth factor alpha polypeptide | 2.21 | 0.00176418 |
| N-acylsphingosine amidohydrolase (non-lysosomal) | 2.20 | 0.00728536 |
| S-phase kinase-associated protein 2 (p45) | 2.20 | 0.00230153 |
| polymerase (RNA) III (DNA directed) polypeptide G (32 kD) | 2.20 | 0.0298794 |
| ADP-ribosylation factor-like 6 interacting protein 1 | 2.20 | 0.00139745 |
| historic cluster 1, H2bh | 2.19 | 0.0377748 |
| origin recognition complex, subunit 5-like (yeast) | 2.19 | 0.049697 |
| CDC28 protein kinase regulatory subunit 2 | 2.19 | 0.0128024 |
| histone cluster 1, H4c | 2.19 | 0.0112695 |
| hypothetical protein LOC729012 | 2.19 | 0.000446087 |
| DEAD (Asp-Gin-Ala-Asp) box polypeptide 39 | 2.19 | 0.000140561 |
| chromatin assembly factor 1, subunit B (p60) | 2.18 | 0.0119687 |
| MLF1 interacting protein | 2.18 | 0.0177203 |
| microtubule associated serine | 2.18 | 0.00536974 |
| MHC class I polypeptide-related sequence B | 2.18 | 0.0165406 |
| shugoshin-like 2 (S. pompe) | 2.18 | 0.000852557 |
| COP9 constitutive photomorphogertic homolog subunit 6 (Arab | 2.18 | 0.000793512 |
| methlyenetetrahydrofolate dehydrogenase (NADP+ dependent) | 2.18 | 0.00119726 |
| chromosome 6 open reading frame 167 | 2.18 | 0.0011095 |
| pituitary tumor-transforming 1 | 2.17 | 0.0485166 |
| ribonuclease H2, subunit A | 2.17 | 0.00669936 |
| X-ray repair complementing defective repair in Chinese ham | 2.16 | 0.0369865 |

TABLE 5-continued

Gene expression in Celligen compared to Plurix cells

| Gene | Celligen vs. Plurix (fold change) | p-value (treat) |
|---|---|---|
| membrane protein, palmitoylated 5 (MAGUK p55 subfamily memb | 2.16 | 0.00211873 |
| karyopherin alpha 2 (RAG cohort 1, importin alpha 1) | 2.16 | 0.000650645 |
| pleckstrin homology domain containing, family A | 2.15 | 0.0256434 |
| ribosomal protein L39-like | 2.15 | 0.00429384 |
| karyopherin alpha 2 (RAG cohort 1, importin alpha 1) | 2.15 | 0.000700649 |
| amyloid beta (A4) precursor protein-binding, family B, | 2.15 | 0.00201004 |
| minichromosome maintenance complex component 3 | 2.14 | 0.0018389 |
| histone cluster 1, H2ai | 2.14 | 0.0129155 |
| chromosome 13 open reading frame 34 | 2.14 | 0.000702936 |
| RA 18 homolog (S. cerevisiae) | 2.14 | 0.0016685 |
| WD repeat and HMG-box DNA binding protein 1 | 2.13 | 0.0034833 |
| sulfide quinone reductase-like (yeast) | 2.13 | 0.0473641 |
| chromosome 16 open reading frame 63 | 2.12 | 0.000804179 |
| M-phase phosphoprotein 1 | 2.12 | 0.0271814 |
| minichromosome maintenance complex component 6 | 2.12 | 0.0161279 |
| homeobox A9 | 2.11 | 0.00520942 |
| fibroblast growth factor 9 (glia-activating factor) | 2.10 | 0.0475844 |
| cell division cycle 25 homolog C (S. pombe) | 2.10 | 0.0169914 |
| chromosome 9 open reading frame 64 | 2.10 | 0.0265979 |
| U2AF homology motif (UHM) kinase 1 | 2.09 | 0.0255167 |
| replication factor C (activator 1) 2, 40 kDa | 2.09 | 0.00768959 |
| hypothetical protein LOC440894 | 2.09 | 0.0103358 |
| small nuclear ribonucleoprotein D1 polypeptide 16 kDa | 2.09 | 0.0334665 |
| CSE1 chromosome segregation 1-like (yeast) | 2.09 | 0.0011662 |
| phosphatidylinositol glycan anchor biosynthesis, class W | 2.09 | 0.0151967 |
| centromere protein O | 2.09 | 0.00397056 |
| family with sequence similarity 20, member B | 2.09 | 0.00460031 |
| hypothetical protein FLJ40869 | 2.09 | 0.00444509 |
| guanine nucleotide binding protein (G protein), gamma 11 | 2.08 | 0.00140559 |
| calcyclin binding protein | 2.08 | 0.00524566 |
| ATP-binding cassette, sub-family E (OABP), member 1 | 2.08 | 0.00454751 |
| CD44 molecule (Indian blood group) | 2.08 | 0.000651436 |
| exosome component 8 | 2.08 | 0.00132017 |
| family with sequence similarity 102, member B | 2.08 | 0.025743 |
| histone cluster 2, H3d | 2.07 | 0.0102932 |
| family with sequence similarity 33, member A | 2.07 | 0.000318673 |
| Fanconi anemia, complementation group B | 2.07 | 0.000255109 |
| kinesin family member 22 | 2.07 | 0.0192406 |
| histone cluster 1, H2ai | 2.07 | 0.0161621 |
| vaccinia related kinase 1 | 2.06 | 0.0233182 |
| integrator complex subunit 7 | 2.06 | 0.000841371 |
| flap structure-specific endonuclease 1 | 2.06 | 0.006882 |
| hypothetical protein FLT25416 | 2.06 | 0.000177531 |
| ecotropic viral integration site 215 | 2.06 | 0.0171408 |
| retinitis pigmentosa 2 (X-linked recessive) | 2.05 | 0.0264185 |
| centromere protein L | 2.05 | 0.000880856 |
| cofactor required for Sp1 transcriptional activation, subu | 2.04 | 0.00141809 |
| chromosome 20 open reading frame 121 | 2.04 | 0.0146323 |
| family with sequence similarity 72, member A | 2.04 | 0.00162905 |
| family with sequence similarity 72, member A | 2.04 | 0.00165234 |
| eukaryotic translation initiation factor 1A, X-linked | 2.04 | 0.00520549 |
| elongation factor, RNA polymerase II, 2 | 2.03 | 0.0458007 |
| ATPase, Na+ | 2.03 | 0.0189108 |
| histone cluster 1, H3a | 2.03 | 0.0244273 |
| brix domain containing 1 | 2.03 | 0.00981178 |
| sushi domain containing 1 | 2.03 | 0.0258164 |
| ectonucleoside triphosphate diphosphohydrolase 6 | 2.03 | 0.00423628 |
| filactosamine 3 kinase | 2.03 | 0.00470972 |
| Bloom syndrome | 2.02 | 0.0209259 |
| tubulin, alpha 1c | 2.01 | 0.00862586 |
| E2F transcription factor 2 | 2.01 | 0.0496479 |
| exosome component 2 | 2.01 | 0.00649147 |
| kinesin family member 22 | 2.01 | 0.0247075 |
| LTV1 homolog (S. cerevisiae) | 2.01 | 0.00812652 |
| dihydrolipoamide S-acetyltransferase (E2 component of pyruv | 2.01 | 0.00179011 |
| viral simian leukemia viral oncogene homolog B (ras related) | 2.01 | 0.017225 |
| ring finger and WD repeat domain 3 | 2.01 | 0.0013797 |
| annexin A1 | 2.01 | 0.0173578 |
| elaC homolog 2 (E. coli) | 2.00 | 0.00266504 |
| aldehyde dehydrogenase 9 family, member A1 | 2.00 | 0.00911609 |

TABLE 5-continued

Gene expression in Celligen compared to Plurix cells

| Gene | Celligen vs. Plurix (fold change) | p-value (treat) |
|---|---|---|
| tubulin, alpha 4a | 2.00 | 0.0435427 |
| nuclear pore complex interacting protein | −2.00 | 0.00111223 |
| oculomedin | −2.01 | 0.00778869 |
| similar to PI-3-kinase-related kinase SMG-1 | −2.01 | 0.0356628 |
| golgi autoantigen, golgin subfamily a-like pseudogene | −2.01 | 0.00770626 |
| spectrin repeat containing, nuclear envelope 1 | −2.01 | 0.00438469 |
| nuclear pore complex interacting protein | −2.01 | 0.00117582 |
| sushi, nidogen and EGF-like domains 1 | −2.01 | 0.00161129 |
| integrin, alpha V (vitronectin receptor, alpha polypeptide | −2.02 | 0.00252702 |
| cyclin-dependent kinase inhibitor 2B (p15, inhibits CDK4) | −2.04 | 0.0150268 |
| lysyl oxidase-like 4 | −2.04 | 0.0120148 |
| nuclear pore complex interacting protein | −2.04 | 0.000213956 |
| calcium | −2.04 | 0.00657494 |
| calsyntenin 3 | −2.04 | 0.00300887 |
| cell adhesion molecule 1 | −2.05 | 0.0261129 |
| solute carrier family 22 (organic cation transporter), | −2.05 | 0.0137275 |
| RUN and FYVE domain containing 3 | −2.05 | 0.00387265 |
| glucosidase, alpha; acid (Pompe disease, glycogen storage) | −2.05 | 0.000418401 |
| nuclear pore complex interacting protein | −2.05 | 0.00988632 |
| proline-rich nuclear receptor coactivator 1 | −2.06 | 0.0039587 |
| membrane metallo-endopeptidase | −2.06 | 0.0152684 |
| PHD finger protein 21A | −2.06 | 0.00980401 |
| Rho GTPase-activating protein | −2.06 | 0.00705186 |
| homeobox B6 | −2.06 | 0.00301714 |
| nuclear pore complex interacting protein | −2.07 | 0.00032839 |
| phospholipase A2 receptor 1, 180 kDa | −2.07 | 0.00069343 |
| nuclear pore complex interacting protein | −2.08 | 0.000352007 |
| slit homolog, 3 (*Drosophila*) | −2.08 | 0.02844 |
| nuclear pore complex interacting protein | −2.09 | 0.000414309 |
| cyclin-dependent kinase 6 | −2.09 | 0.0456892 |
| dynamin 1 | −2.09 | 0.00139674 |
| jumonji, AT rich interactive domain 1B | −2.09 | 0.00861002 |
| calcium binding and coiled-coil domain 1 | −2.09 | 0.00370041 |
| insulin-like growth factor 1 receptor | −2.09 | 0.00114467 |
| nuclear pore complex interacting protein | −2.10 | 0.000177834 |
| CD82 molecule | −2.10 | 0.0175517 |
| bromodomain adjacent to zinc finger domain, 2B | −2.10 | 9.88E−05 |
| — | −2.10 | 0.00666187 |
| synaptotagmin XI | −2.11 | 0.0129428 |
| KIAA1546 | −2.11 | 0.000255634 |
| jun B proto-oncogene | −2.12 | 0.0120169 |
| CXXC finger 6 | −2.12 | 0.0277527 |
| nuclear pore complex interacting protein | −2.14 | 0.00282604 |
| Cdon homolog (mouse) | −2.15 | 0.0350357 |
| B-cell CLL | −2.15 | 0.00343507 |
| nuclear pore complex interacting protein | −2.15 | 0.00263888 |
| v-abl Abelson marine leukemia viral oncogene homolog 1 | −2.16 | 0.0136688 |
| nuclear pore complex interacting protein | −2.16 | 0.00583397 |
| FAT tumor suppressor homolog 1 (*Drosophila*) | −2.18 | 0.0158766 |
| transformer-2 alpha | −2.18 | 0.012256 |
| chimerin (chimaerin) 1 | −2.18 | 0.0287031 |
| milk fat globule-EGF factor 8 protein | −2.18 | 0.000987073 |
| vitamin D (1,25-dihydroxyvitamin D3) receptor | −2.19 | 0.000192208 |
| neuroblastoma, suppression of tumorigenicity 1 | −2.20 | 0.00090639 |
| jumonji domain containing 1A | −2.20 | 0.0188513 |
| WNK lysine deficient protein kinase 1 | −2.21 | 1.57E−05 |
| protocadherin beta 14 | −2.21 | 0.0103892 |
| cortactin binding protein 2 | −2.11 | 2.28E−05 |
| WW domain containing transcription regulator 1 | −2.22 | 0.0379899 |
| cyclin L1 | −2.22 | 0.00831474 |
| nuclear factor of activated T-cells, cytoplasmic, calcine | −2.22 | 0.00786451 |
| pellino homolog 1 (*Drosophila*) | −2.23 | 0.00939357 |
| golgi autoantigen, golgin subfamily a-like pseudogene | −2.24 | 0.00603583 |
| chromosome 7 open reading frame 10 | −2.26 | 0.00738442 |
| golgi autoantigen, golgin subfamily a-like pseudogene | −2.27 | 0.00320764 |
| small Cajal body-specific RNA 17 | −2.27 | 0.0301336 |
| latent transforming growth factor beta binding protein 2 | −2.29 | 4.08E−05 |
| golgi autoantigen, golgin subfamily a, 8A | −2.29 | 0.0111179 |
| inhibin, beta A (activin A, activin AB alpha polypeptide) | −2.29 | 0.00877271 |
| solute carrier family 41, member 2 | −2.30 | 0.00451672 |
| forkhead box P1 | −2.30 | 0.0463138 |

TABLE 5-continued

Gene expression in Celligen compared to Plurix cells

| Gene | Celligen vs. Plurix (fold change) | p-value (treat) |
|---|---|---|
| matrix metallopeptidase 14 (membrane-inserted) | −2.31 | 1.91E−05 |
| transcription factor 4 | −2.31 | 0.0367869 |
| jun oncogene | −2.32 | 7.21E−05 |
| neuroepithelial cell transforming gene 1 | −2.33 | 0.0109689 |
| asporin | −2.33 | 0.000659873 |
| v-fos FBJ murine osteosarcoma viral oncogene homolog | −2.35 | 0.0138624 |
| ephrin-B2 | −2.36 | 0.00611474 |
| WD repeat and SOCS box-containing 1 | −2.36 | 0.0387851 |
| similar to dJ402H5.2 (novel protein | −2.36 | 0.00621503 |
| PX domain containing serine | −2.38 | 0.000927628 |
| collagen, type VII, alpha 1 (epidermolysis bullosa | −2.38 | 0.00109233 |
| AE binding protein 1 | −2.39 | 0.000105628 |
| peroxidasin homolog (Drosophila) | −2.40 | 0.00219049 |
| calcium channel, voltage-dependent, L type, alpha 1C sub | −2.41 | 0.0189661 |
| Prader-Willi syndrome chromosome region 1 | −2.45 | 0.0415526 |
| midline 1 (Opitz | −2.45 | 0.00130803 |
| nuclear pore complex interacting protein | −2.45 | 0.00354416 |
| chromosome 1 open reading frame 54 | −2.47 | 0.0186089 |
| transmembrane protein 16A | −2.48 | 0.0481085 |
| basic helix-loop-helix domain containing, class B, 2 | −2.49 | 0.00270257 |
| nuclear pore complex interacting protein | −2.50 | 0.00316496 |
| runt-related transcription factor 1 | −2.50 | 0.000607387 |
| zinc finger protein 292 | −2.50 | 0.029832 |
| fibronectin leucine rich transmembrane protein 2 | −2.51 | 0.0135122 |
| nuclear pore complex interacting protein | −2.51 | 0.00283418 |
| potassium voltage-gated channel, subfamily G, member 1 | −2.54 | 0.0244306 |
| interleukin 19 | −2.54 | 0.0310328 |
| transforming growth factor, beta 3 | −2.54 | 0.0287865 |
| dihydropyrimidinase-like 3 | −2.55 | 0.0165203 |
| golgi autoantigen, golgin subfamily a, 8B | −2.56 | 0.0121417 |
| hypothetical protein PRO2012 | −2.57 | 0.00756704 |
| SATB homeobox 2 | −2.57 | 0.039781 |
| t-complex 11 (mouse)-like 2 | −2.57 | 0.0324227 |
| ring finger protein 122 | −2.57 | 0.0236621 |
| chromosome 8 open reading frame 57 | −2.59 | 0.00261522 |
| ADAM metallopeptidase with throinbospondin type 1 motif, | −2.60 | 0.0113968 |
| sushi, von Willebrand factor type A, EGF and pentraxin | −2.63 | 2.23E−05 |
| ST6 beta-galactosamide alpha-2,6-sialyltranferase 2 | −2.64 | 0.0216987 |
| sortilin-related VPS10 domain coniaining receptor 2 | −2.65 | 0.00936311 |
| protocadherin beta 9 | −2.66 | 0.0285124 |
| chromosome 5 open reading frame 13 | −2.67 | 0.00410172 |
| Enah | −2.68 | 0.0077547 |
| pyridoxal-dependent decarboxylase domain containing 2 | −2.69 | 0.00683647 |
| similar to nuclear pore complex interacting protein | −2.70 | 0.0187322 |
| nuclear pore complex interacting protein | −2.70 | 0.00368967 |
| transmembrane protein 119 | −2.70 | 0.00501387 |
| chromosome 14 open reading frame 37 | −2.70 | 0.0182453 |
| sushi-repeat-containing protein, X-linked 2 | −2.71 | 0.0253856 |
| PDZ domain containing RING finger 3 | −2.71 | 0.00931014 |
| collagen, type XII, alpha 1 | −2.72 | 0.000204664 |
| matrix-remodelling associated 5 | −2.72 | 0.000317637 |
| collagen, type V, alpha 1 | −2.72 | 0.0166427 |
| dystrophin related protein 2 | −2.72 | 0.0137557 |
| ATP-binding cassette, sub-family A (ABC1), member 1 | −2.73 | 0.00131361 |
| trophinin | −2.77 | 0.00298044 |
| cornichon homolog 3 (Drosophila) | −2.78 | 0.0261738 |
| formin binding protein 1-like | −2.78 | 0.00290401 |
| brain and acute leukemia, cytoplasmic | −2.78 | 0.0476919 |
| protein tyrosine phosphatase, receptor type, U | −2.80 | 0.0270428 |
| hypothetical protein MGC24103 | −2.82 | 0.0346673 |
| interferon induced with helicase C domain 1 | −2.83 | 0.0024839 |
| phospholipid transfer protein | −2.84 | 0.00999206 |
| immediate early response 3 | −2.87 | 0.0152127 |
| immediate early response 3 | −2.87 | 0.0152127 |
| ADAM inetallopeptidase domain 12 (meltrin alpha) | −2.87 | 0.000870288 |
| synaptic vesicle glycoprotein 2A | −2.88 | 0.00704212 |
| chromosome 9 open reading frame 3 | −2.88 | 0.00410177 |
| thioredoxin interacting protein | −2.90 | 0.0135494 |
| early growth response 1 | −2.93 | 0.000425035 |
| small nucleolar RNA, C | −2.94 | 0.00666866 |
| small nucleolar RNA, C | −2.95 | 0.00765575 |
| immediate early response 3 | −2.99 | 0.0167309 |

TABLE 5-continued

Gene expression in Celligen compared to Plurix cells

| Gene | Celligen vs. Plurix (fold change) | p-value (treat) |
|---|---|---|
| low density lipoprotein related protein 1 (alpha-2-macroglo | −2.99 | 4.26E−05 |
| bicaudal C homolog 1 (*Drosophila*) | −2.99 | 0.0347162 |
| homeobox B2 | −3.03 | 0.00665994 |
| small nucleolar RNA, C | −3.10 | 0.0274043 |
| small nucleolar RNA, C | −3.10 | 0.0274043 |
| matrix metallopeptidase 2 (gelatinase A, 72 kDa gelatinase, | −3.13 | 5.59E−05 |
| KIAA1641 | −3.14 | 0.00659194 |
| collagen, type VI, alpha 3 | −3.14 | 2.09E−06 |
| homeobox A2 | −3.15 | 0.0435423 |
| SH3 and PX domains 2B | −3.15 | 0.0244357 |
| collagen, type VI, alpha 2 | −3.16 | 0.0149554 |
| chromosome 9 open reading frame 3 | −3.21 | 0.0233723 |
| small nucleolar RNA, C | −3.24 | 0.0104491 |
| small nucleolar RNA, C | −3.24 | 0.0104491 |
| — | −3.27 | 0.00488845 |
| UDP-N-acetyl-alpha-D-galactosamine: polypeptide N-acetylga | −3.35 | 0.00964109 |
| cholesterol 25-hydroxylase | −3.38 | 0.0445558 |
| KIAA1641 | −3.40 | 0.013175 |
| ring finger protein 144 | −3.40 | 0.0135334 |
| versican | −3.41 | 0.023885 |
| angiopoietin-like 2 | −3.42 | 0.0245161 |
| KIAA1641 | −3.44 | 0.0170531 |
| FBJ murine osteosarcoma viral oncogene homolog B | −3.54 | 0.00025573 |
| similar to RIKEN cDNA 1110018M03 | −3.59 | 0.00516476 |
| early growth response 2 (Krox-20 homolog, *Drosophila*) | −3.62 | 0.00821813 |
| dachsous 1 (*Drosophila*) | −3.63 | 0.00697244 |
| kinesin family member 26B | −3.64 | 0.00363199 |
| distal-less homeobox 5 | −3.66 | 0.000640157 |
| similar to Protein KIAA0220 | −3.69 | 0.0302619 |
| insulin-like growth factor 1 receptor | −3.71 | 3.42E−05 |
| protein tyrosine phosphatase, receptor type, N | −3.77 | 0.0294569 |
| KIAA1641 | −3.85 | 0.0191782 |
| sushi-repeat-containing protein, X-linked | −3.85 | 0.00370941 |
| microfibrillar-associated protein 2 | −3.91 | 0.0152901 |
| complement component 1, s subcomponent | −3.97 | 0.0395863 |
| CD24 molecule | −3.99 | 0.0340122 |
| homeobox B3 | −4.02 | 0.0354368 |
| trichorhinophalangeal syndrome I | −4.02 | 0.00557712 |
| Kallmann syndrome 1 sequence | −4.04 | 0.000548703 |
| leucine rich repeat containing 17 | −4.09 | 0.0263961 |
| plexin domain containing 2 | −4.32 | 0.031799 |
| PTK7 protein tyrosine kinase 7 | −4.42 | 0.000116114 |
| supervillin | −4.43 | 0.0412717 |
| zinc finger protein 521 | −4.58 | 0.00668815 |
| calbindin 2, 29 kDa (calretinin) | −4.77 | 0.0290743 |
| ras homolog gene family, member J | −4.79 | 0.00197982 |
| integrin, alpha 11 | −4.80 | 0.000390317 |
| odz, odd Oz | −5.05 | 0.00172671 |
| F-box protein 32 | −5.52 | 0.0212957 |
| raftlin family member 2 | −5.72 | 0.0260454 |
| clusterin | −5.74 | 0.0303973 |
| neurotrimin | −5.79 | 3.78E−06 |
| WNT1 inducible signaling pathway protein 1 | −5.86 | 0.000672342 |
| insulin-like growth factor binding protein 5 | −6.34 | 0.011614 |
| sulfatase 2 | −6.34 | 5.88E−05 |
| microfibrillar-associated protein 4 | −6.93 | 0.00155578 |
| junctional adhesion molecule 2 | −7.07 | 0.0306758 |
| fibronectin type III domain containing 1 | −7.29 | 0.0334696 |
| sarcoglycan, delta (35 kDa dystrophin-associated) | −7.37 | 0.000881984 |
| hephaestin | −7.53 | 0.0123141 |
| serpin peptidase inhibitor, clade F (alpha-2) | −7.66 | 0.00362941 |
| cystatin SN | −7.96 | 0.0496433 |
| hemicentin 1 | −8.18 | 0.0461603 |
| tenascin C (hexabrachion) | −8.32 | 8.06E−05 |

TABLE 5-continued

Gene expression in Celligen compared to Plurix cells

| Gene | Celligen vs. Plurix (fold change) | p-value (treat) |
|---|---|---|
| biglycan | −8.62 | 0.00161284 |
| transmembrane, prostate androgen induced RNA | −11.20 | 0.000100935 |
| carboxypeptidase E | −11.22 | 0.00738131 |

Expression of cellular markers on PLX-C cells—the surface antigens expressed by PLX-C were examined using monoclonal antibodies. Results indicated that PLX-C cells were characterized by the positive markers: CD73, CD29 and CD105 and the negative markers: CD34, CD45, CD19, CD14 and HLA-DR (data not shown). The immune phenotype test specifications were set as: ≥90% for all positive markers and ≤3% for all negative markers.

Figures 10A, 10B, 10C:
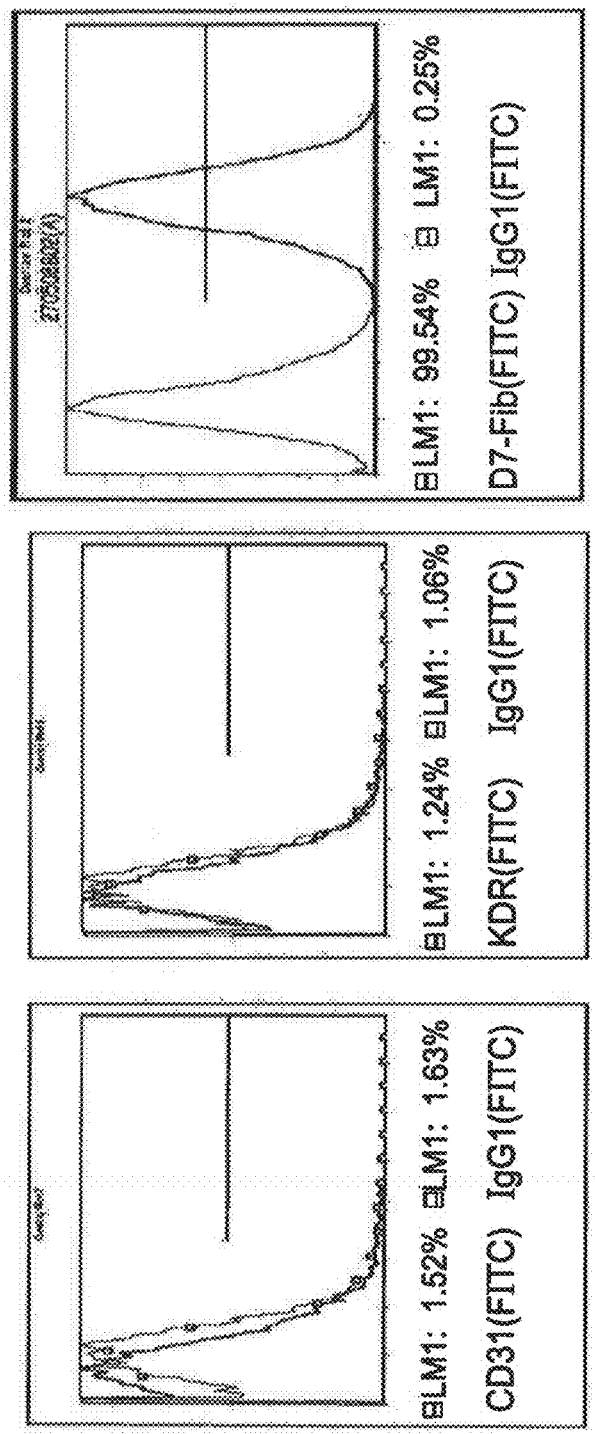
FIGS. 10A-C depict expression of fibroblast-typical markers but not expression of endothelial typical markers on PLX-C.

Furthermore, as shown in FIGS. 10A-B, PLX-C cultures did not express endothelial markers as shown by negative staining for the two endothelial markers CD31 and KDR. However, PLX-C expression of a fibroblast-typical marker was evident (expression of D7-fib, FIG. 10C).

Immunogenecity and immunomodulatory properties of PLX-C cells—as PLX-C is comprised of adherent cells derived from placenta, it is expected to express HLA type I, which is expressed by all cells of the body and is known to induce an alloreactive immune response. HLA type II and other co-stimulatory molecules are typically expressed only on the surface of Antigen Presenting Cells (APCs).

Figure 11A:
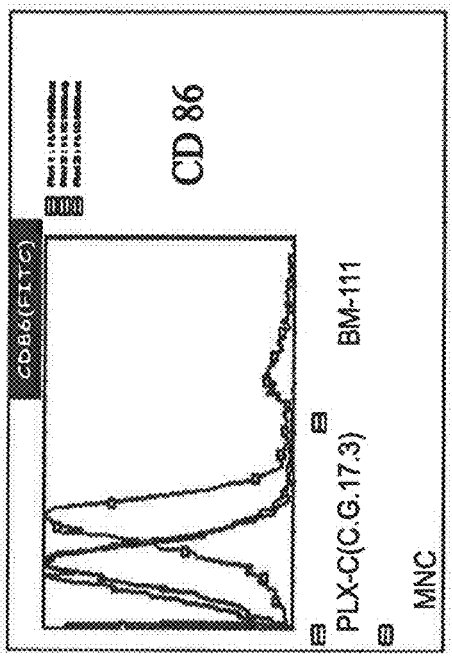
FIGS. 11A-D depict expression of stimulatory and co-stimulatory molecules on PLX-C cells.
Figure 11B:
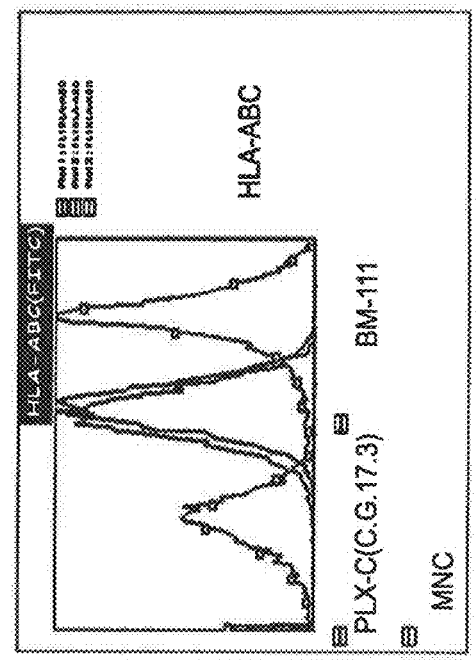
Figure 11C:
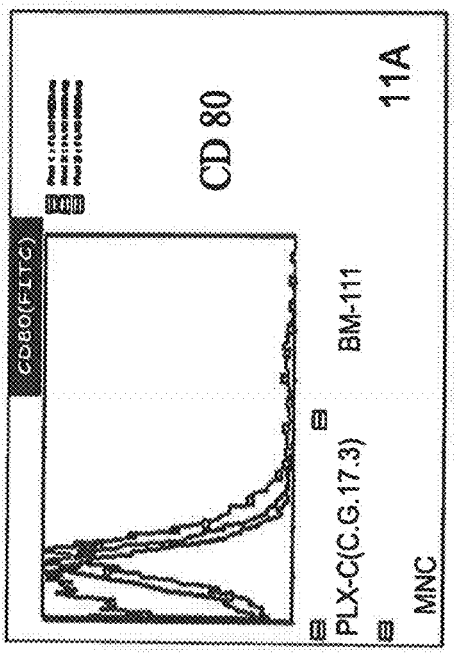
Figure 11D:
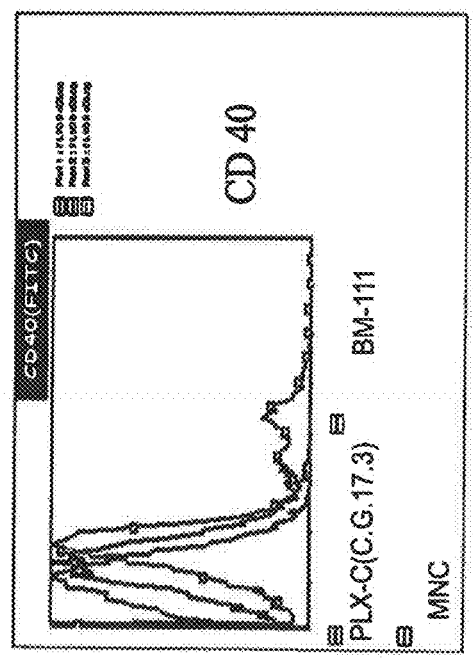

In order to examine the immunogenicity of the obtained PLX-C cells, the expression of co-stimulatory molecules on the surface of these cell membranes were performed. FACS analysis demonstrated the absence of CD80, CD86 and CD40 on the PLX-C cell membranes (FIGS. 11A-C). Moreover, PLX-C expressed low levels HLA class 1 as detected by staining for HLA A/B/C (FIG. 11D). The expression of stimulatory and co-stimulatory molecules was similar to bone marrow (BM) derived MSCs (as shown in FIGS. 11A-D).

To further investigate the immunogenecity as well as the immunomodulation properties of PLX-C cells, Mix Lymphocyte Reaction (MLR) tests were performed. As shown in FIG. 12A-B, PLX-C cells both escape allorecognition, and reduce T cell response, as measured by Thymidine incorporation. Furthermore, the reduction in lymphocytes proliferation (evaluated by CPM measurement) was higher as the number of PLX-C cells increased (in a dose dependent manner). PLX-C also reduced lymphocyte proliferation following mitogenic stimuli, such as Concavalin A (Con A, FIG. 12B) and Phytohemagglutinin (PHA), and non-specific stimulation by anti-CD3, anti-CD28 (data not shown).

In order to investigate the mechanism of action by which PLX-C immunomodulate lymphocyte proliferation, and to see if this action is mediated via cell to cell interaction or cytokines secretion, PB derived Mononuclear cells (MNCs) were stimulated by PHA using the transwell method (which prevents cell to cell contact but enables the diffusion of cytokines between the two compartments). Results showed that the inhibition of proliferation maintained even when cell to cell contact was inhibited (data not shown).

Figure 13C:
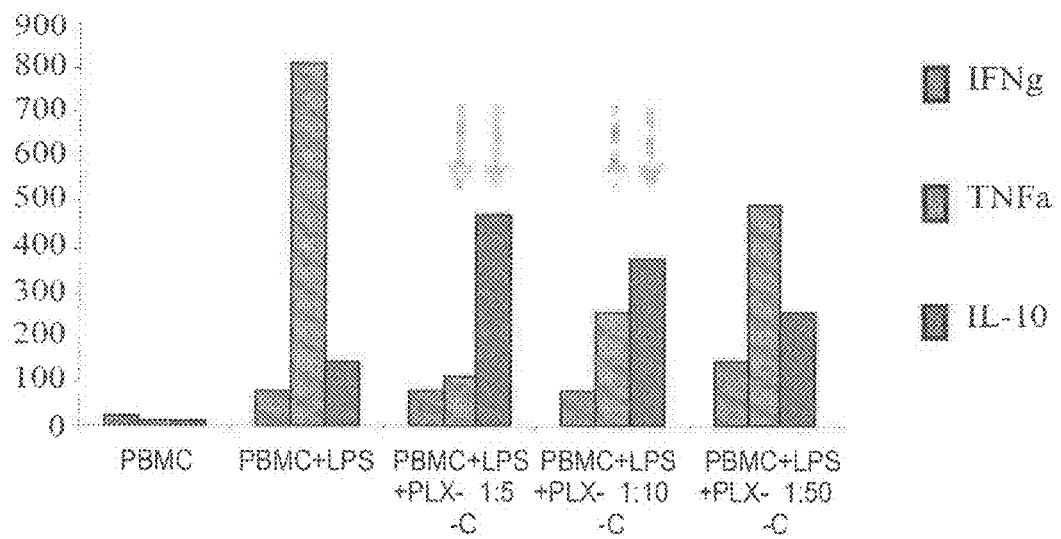

Cytokines secretion—as depicted hereinabove, PLX-C reduce the proliferation rate of lymphocytes, probably through soluble factors. Further investigation of the cytokines secreted by lymphocytes in response to PLX-C was performed to elucidate the mechanism of action of PLX-C. As depicted in FIGS. 13A-B, culturing of mononuclear cells with PLX-C slightly reduces the secretion of the pro-inflammatory cytokine INFγ and dramatically reduces the secretion of TNFα (even in the presence of low amounts of PLX-C). In addition, following lipopolysaccharide (LPS) stimulation, PB derived MNCs secretion of IL-10 increased in the presence of PLX-C, while the secretion level of TNFα decreased, in a dose dependent manner (FIG. 13C).

Example 5

Biodistribution of PLX-C

Figure 14:
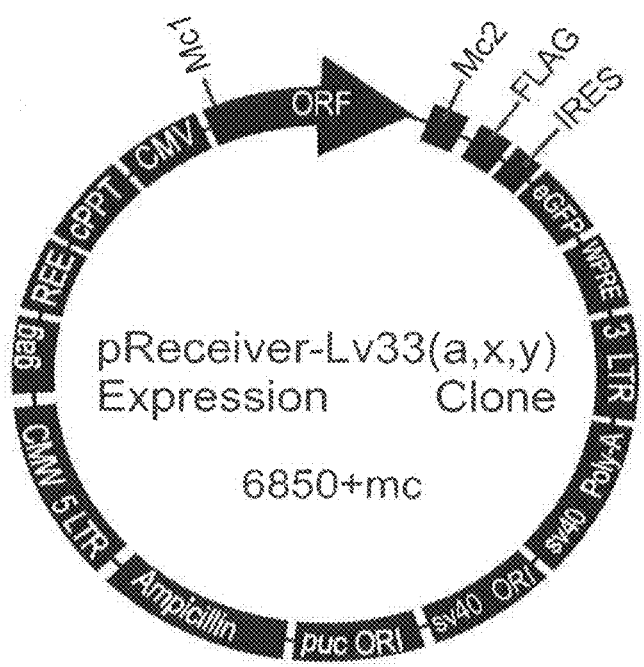
FIG. 14 depicts the luciferase expression vector used to infect PLX-C cells. Expression vector Lv33 from OmicsLink was used herein. The Luciferase gene was cloned into the ORF.

Materials and Experimental Methods
Transfection of PLX-C Cells with Luciferase Expression Vector PLX-C cells were stably infected with a lentiviral construct expressing the luciferase gene under the CMV promoter (FIG. 14).

Production of Infecting Virus

293TN producer cells were grown in DMEM medium (Gibco) supplemented with serum and antibiotics for 2-3 days (50-70% confluency) prior to transfection. A mixture of 10 μg of the packaging plasmid and 2 μg of expression construct and 20 μl of Plus™ Reagent (Invitrogen) were added to 400 μl of DMEM without supplements. The mixture was incubated for 15 min at room temperature (RT) and Lipofectamine™ (30 μl dilutes in 400 μl of DMEM were added). The mixture was incubated at RT for 15 min. 293TN cells were washed and transferred to 2% serum media and transfection mixture was added. Cells were incubated in $CO_2$ incubator at 37° C. over night and medium was collected 24-60 hrs post infection. Peak virus production was achieved after 48 hrs. Medium was collected, and centrifuged at 3000 rpm at room temperature for 5 minutes to pellet cell debris. Following centrifugation, the supernatant was filtered through Millex-HV 0.45 μm PVDF filters (Millipore, Cat. #SLHVR25LS).

Infection of PLX-C

PLX-C cells were seeded in a 24-well plate at a density of $0.6-1 \times 10^5$ cells per well in complete medium 24 hours prior to viral infection. After 24 hrs, 0.5 ml of virus suspension (diluted in complete medium with Polybrene at a final concentration of 5-8 μg/ml) was added. Cells were incubated for 24 hrs, then medium was replaced by complete DMEM medium and cells were incubated at 37° C. with 5% CO2 overnight. At day 4, the culture reached confluency and was split by 1:3 to 1:5, cells were allowed to grow for 48 hours in complete DMEM then cells were analyzed for Luciferase expression.

Efficiency rates of infection were close to 100%. Evaluation of luminescence in living cells and in living mice was performed using the IVIS Lumina Imaging system, which included a highly sensitive CCD camera that captured the luciferase luminescence signal.

Two weeks post infection $2 \times 10^6$ cells were injected IM or IV into SCID/Beige, NOD/SCID, SCID and Balb/C mice. Injected cells were monitored using the described IVIS system.

Experimental Results

Figure 15:
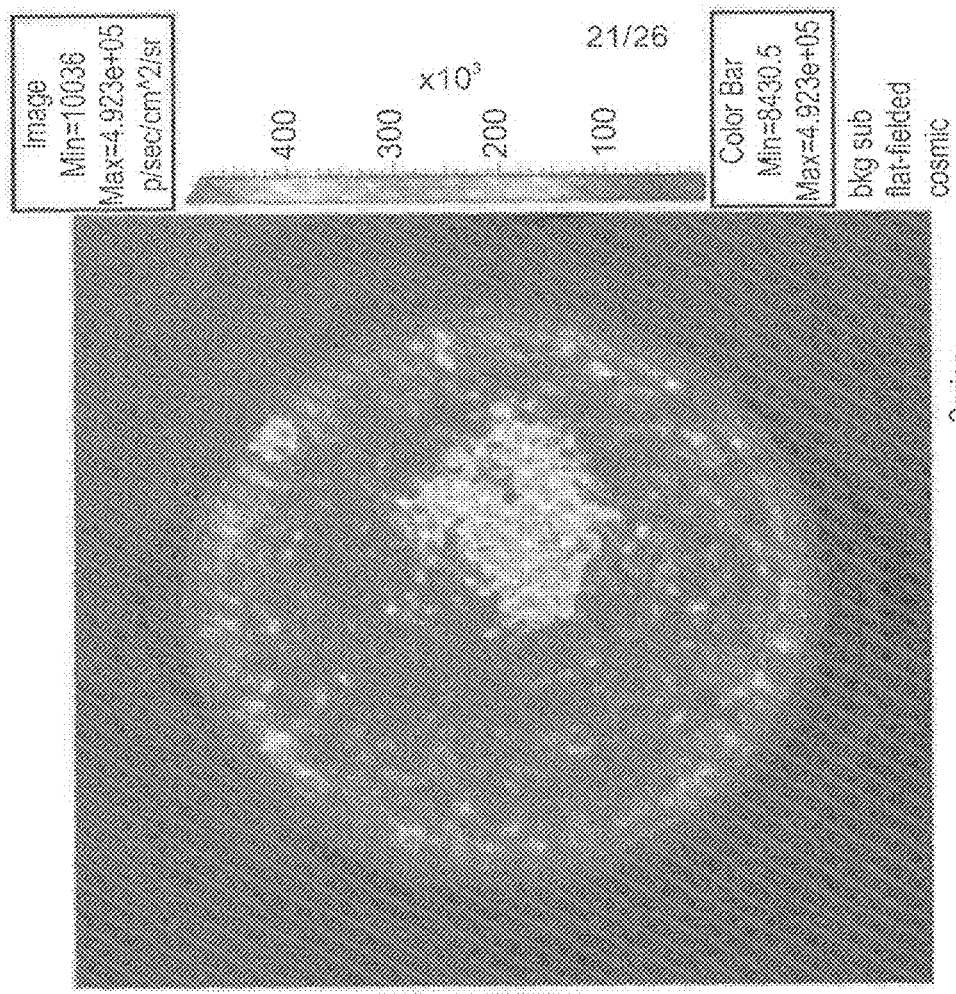
FIG. 15 depicts high luciferase expression by infected PLX-C cells. Cells were infected with the luciferase expression vector and visualized by the IVIS system 48 hours post infection. Of note, cells exhibited high levels of luciferase expression.
Figure 16C:
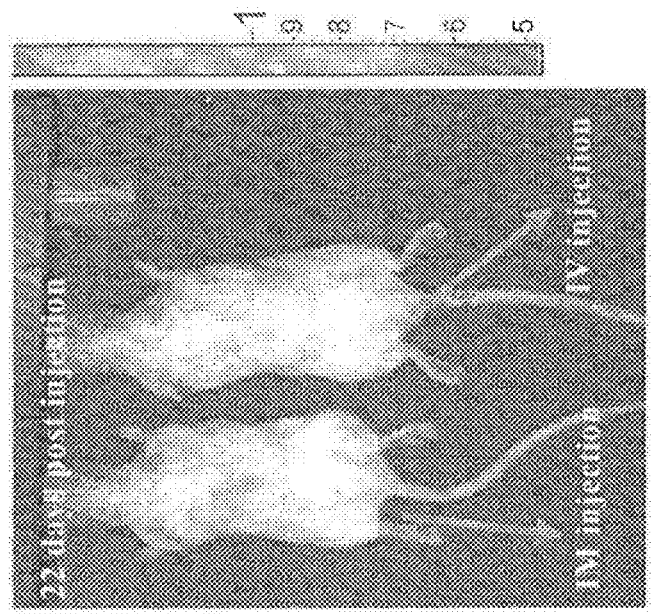
Figure 16D:
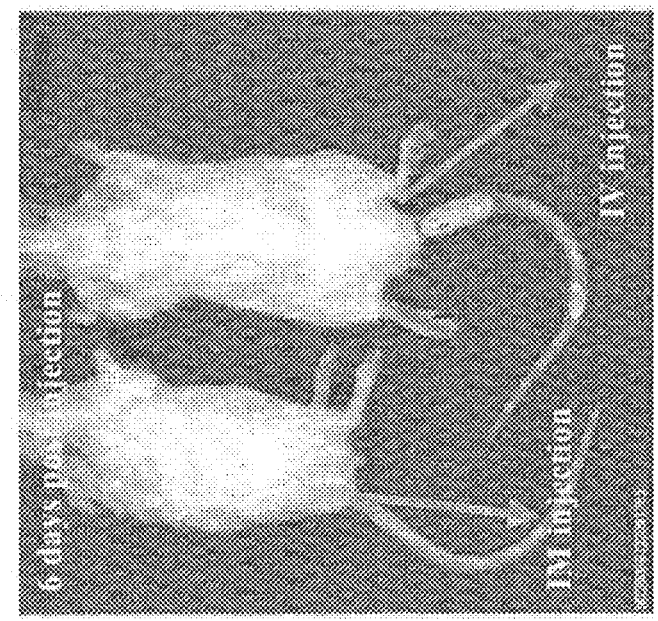

As evident from the results, CXL cells continued to divide following infection, and expression levels of luciferase in the growing cells remained strong and stable (FIG. 15).

Once PLX-C cells were injected into Balb/C mice, the biodistribution pattern was examined. As evident from the results, cells disappeared 72 hrs post IM injection (data not shown). However, PLX-C cells retained constant high levels of luciferase expression, in vitro, for over three weeks (data not shown).

As shown in FIGS. 16A-D, cells injected IM into SCID/Beige mice immunodeficient mice retained up to 5 days at the site of injection and were not observed thereafter. CXL cells injected IV into SCID/Beige mice migrated after 24 hrs to the lungs, then to the site of injection (presumably homing to site of injury). Afterwards cells disappear gradually and were not observed after 3-4 weeks.

Example 6

Adherent Cells are Capable of Treating Limb Ischemia In Vivo

To determine whether implantation of placental derived adherent cells can reduce ischemic damage and improve clinical and motor functions, the hind limb ischemia model was used, as follows.

Materials and Experimental Methods

Hind limb ischemia model—Hind limb ischemia was induced in 20 Male Balb/c mice, which are not immunodeficient, at the age of 8-10 weeks, body weight approximately 25 g±20%. Animals handling was according to the National Institute of Health (NIH) and the Association for Assessment and Accreditation of Laboratory Animal Care (AAALAC). Animals were housed under standard laboratory conditions. Animals were kept in a climate controlled environment. Temperatures range was between 20-24° C. and relative humidity (RH) was between 30-70% with 12 hours light and 12 hours dark cycle.

Animals were randomized using a computer generated randomization program "Research Randomizer" and divided into 2 groups of 10 animals. One group received intramuscular (IM) injection of $1 \times 10^6$ placental derived adherent cells (PLX-C) cells and the other group served as control and was injected with PBS.

Surgical Procedures—1-1.5 cm incision was made in the skin in the inguinal area. The femoral artery was ligated twice with 6-0 silk and trunsected distal to the ligature. The wound was closed with 3-0 silk and the mice were allowed recovering. Five hours post-operative excision of one femoral artery, mice received an IM injection of $1 \times 10^6$ placental derived adherent cells (PLX-C) in a total volume of 50 µl at 2 administration Sites. Control group animals were identically injected with PBS (Gibco), see Table 6 below.

TABLE 6

Pilot study of PLX-C in Mouse Hind limb Ischemia Model

| Test Group | Treatment | No. of Mice per group | Cell Dose | Lot | Time of Sacrifice Post-dosing 21 days |
|---|---|---|---|---|---|
| 1 | PLX-C i.m | n = 10 ♂ | $1 \times 10^6$ | C.G.13.0 | n = 10 ♂ |
| 2 | PBS i.m | n = 10 ♂ | 0 | N/A | n = 10 ♂ |

Follow up—Blood flow on legs from both sides was measured 3 consecutive times with a non contact laser Doppler just after the operation, and on days 6, 9, 14 and 21 post operation, and is expressed as the ratio of the flow in the ischemic limb to that in the normal limb [Tokai. J. et al].

Macroscopic evaluation of ischemic severity—The ischemic limb was macroscopically evaluated at days 1, 6, 9, 14, 21, till study termination by using graded morphological scales for necrotic area; grade 0: absence of necrosis, grade I: necrosis limiting to toes (toes loss), grade II: necrosis extending to a dorsum pedis (foot loss), grade III: necrosis extending to a crus (knee loss), grade IV: necrosis extending to a thigh (total hind-limb loss) [Tokai. J. et al].

In vivo assessment of limb function and ischemic damage—Semiquantitative assessment of impaired use of the ischemic limb was be performed serially as follows: 3=dragging of foot, 2=no dragging but no plantar flexion, 1=plantar flexion, and 0=flexing the toes to resist gentle traction of the tail (Rutherford et al., 1997).

Molecular and biochemical analysis—In addition to clinical evaluation, molecular and biochemical samples were obtained at day 21 and are currently being analyzed in order to better understand the molecular mechanisms underlying improved healing in the placental derived adherent cells (PLX-C) injected group.

Experimental Results

Figure 17:
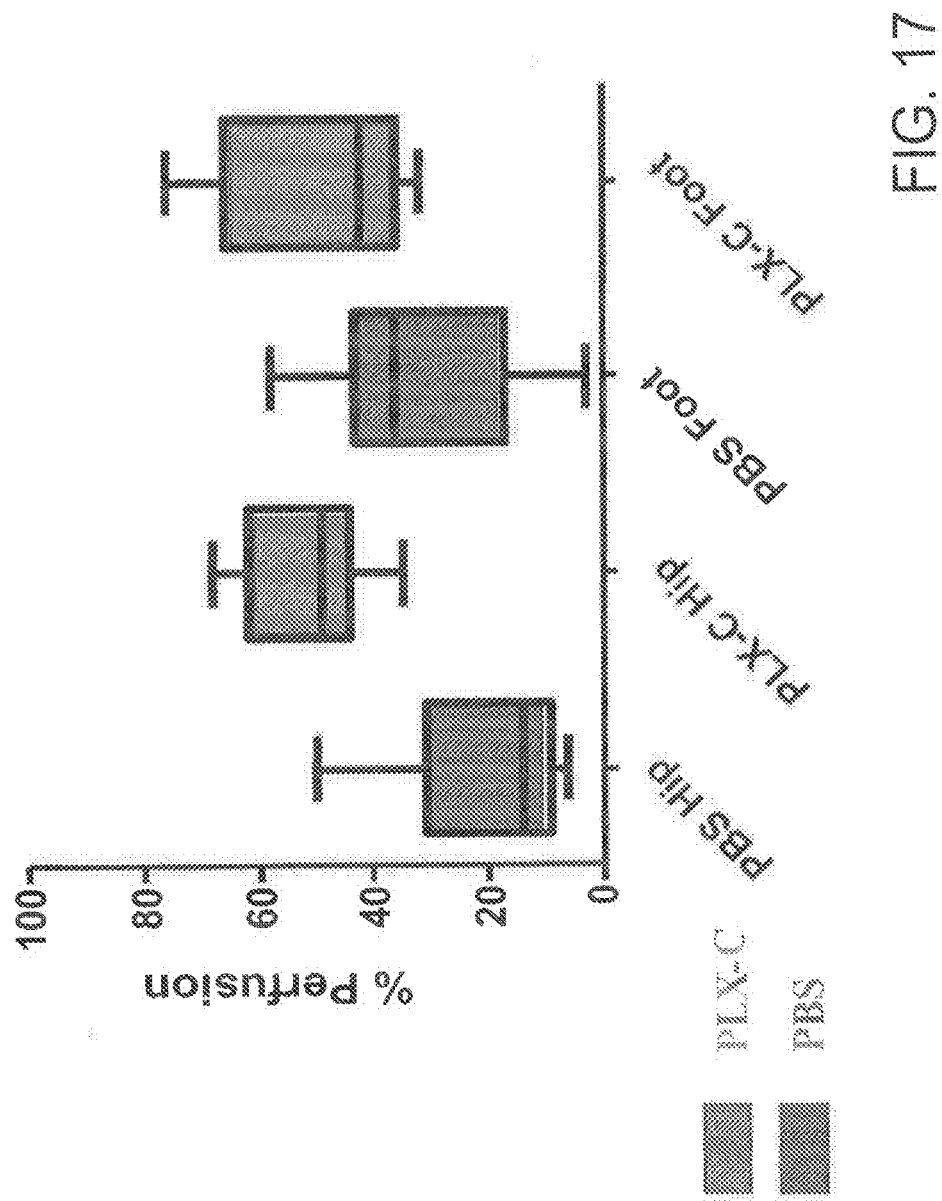
FIG. 17 is a graph depicting increased perfusion in hip and foot of mice treated with the adherent cells of the invention (designated PLX-C). The figure depicts the median of the percent of perfusion in the mouse hip and foot. Blood flows on hip and foot was measured using a non contact laser Doppler from both sides on days 0, 6, 9, 14 and 21 post operation (shown are measurements on day 21). Results are expressed as the ratio of the blood flow in the ischemic limb to that in the normal limb during the experiment.

Implantation of placental derived adherent cells significantly induces blood flow in the hip and foot of the ischemic hind limb model—To test the efficacy of the adherent cells in vivo, mice were subjected artery ligation followed by intramuscular injections of placental derived adherent cells and the blood flow was measured in the hips and foot (both body sides) using a non contact laser Doppler at predetermined time period following treatment. As is shown in FIG. 17, injection of PLX-C markedly improved blood flow (BF) to the damaged limb, as determined by blood flow assessments, increase in limb function, increase in capillary density, decrease in oxidative stress and endothelial damage. In terms of blood flow, the effect was demonstrated 9 days following injection and was observed throughout the entire study. In the PLX-C treated group, BF increased from 24±2.3 to 80±4.7%, while in the control, vehicle-treated group BF was in the range of 35±2 to 54±4.5%—in the hip/implantation area (day 0 vs. day 21, respectively). Similarly to the hip area, but to a lesser extent, an increase in BF was also demonstrated in the paw area of PLX-C treated mice. Thus, in the vehicle treated group BF increased from 12±0.6 to 46±4.9%, while in the PLX-C group BF increased from 10±0.7 to 52±5.5% (day 0 vs. day 21 respectively), as shown in FIG. 17.

Figure 18:
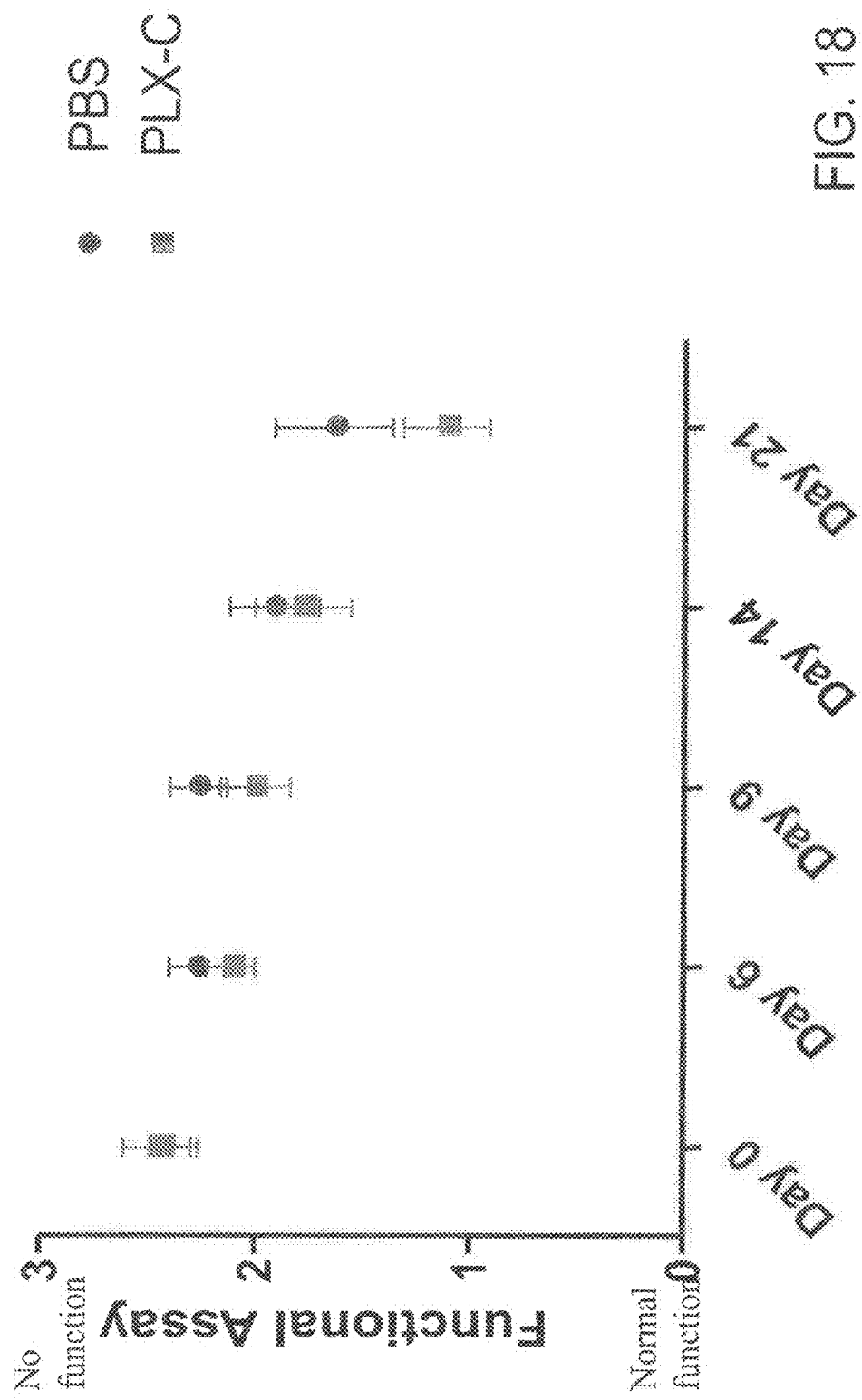
FIG. 18 is a graph depicting the in vivo assessment of limb function and ischemic damage. Semiquantitative assessment of impaired use of the ischemic limb was performed serially using the following score system: 3=dragging of foot, 2=no dragging but no plantar flexion, 1=plantar flexion, and 0=flexing the toes to resist gentle traction of the tail.

The adherent cells are capable of improving limb function in vivo—To further evaluate the in vivo effects of the placental derived adherent cells, the limb functions in the treated mice were assessed using the scoring system described under Materials and Experimental Methods, hereinabove. As is shown in FIG. 18, mice treated with the adherent cells exhibited a significant improvement in the limb function (2.5±0.2 vs. 2.1±0.2 control vs. PLX-C group, respectively, note the significant effect at day 21 post treatment). However, the degree of improvement in limb function during the 21 days observation was comparable, suggesting that PLX-C, under the conditions of the present study did not exhibit a major change of function recovery.

Macroscopic assessment of ischemic severity revealed that in the control, vehicle treated group, necrosis limited to the toes was observed in two animals on day 6. In the PLX-C treated group, necrosis limited to the toes, was demonstrated only in one animal and only after 14 days. Post mortem immunohistochemical analyses of the limbs treated with PLX-C indicated a significant increase in the number of new capillaries (vessels) supplying the limb and suggesting PLX-C possess the ability to promote angiogenesis (FIG. 19).

Finally, a decreased oxidative stress and a reduction in endothelial inflammation (which was a surrogate parameter for improved endothelial function) in the treated animals were observed in the PLX-C treated mice (FIGS. 20A-B). This was likely due to increased oxygen supply in mice treated with PLX-C cells, but not in control mice treated with PBS.

In conclusion, when compared to control, PBS-injected mice, none of the PLX-C injected mice exhibited any adverse clinical signs or symptoms in response to intra mascular (i.m.) cell administration. Thus, PLX-C induces an increase in blood flow, likely resulting from angiogenesis as supported by histological evaluation of the damaged limb. In addition, the delay in development of necrosis and the difference in number of affected animals are suggestive of a clinical response.

Implantation of Placental Derived Adherent Cells

Another efficacy study was carried out in Balb/C mice comprising safety endpoints (i.e., gross necropsis and histopathological analysis of selected organs) as was described in the materials and methods section above.

In this study, seven groups of mice, each consisting of 10 male Balb/c mice (Ischemic hind limb) were used as detailed in Table 7, hereinbelow. A single group of 10 mice did not have ischemia induced (in order to test the overall safety and tolerability of PLX-C cells in normal, healthy animals). Following induction of ischemia, control buffer or PLX-C cells were administered i.m. to the affected limb, and mice were observed for up to 1 month post dosing. A single group of mice received two separate injections in the affected limb, separated by 1 week (Days 1 and 8). Blood flow was monitored by Laser Doppler analysis, and ischemic severity was assessed macroscopically and behaviorally out to 30 days post-dose, at which time, mice were sacrificed, and tissues retained for histological analysis.

TABLE 7

Efficacy study of PLX-C in Mouse Hind limb Ischemia Model

| Test Group no. | Treatment | Cell Amount (Dose) | Number of Treatments | Lot | Time of Sacrifice Post-dosing 30 days |
|---|---|---|---|---|---|
| 1 | PLX-C | 1 × 10$^6$ | 1 | C.G.13.0 | 10 ♂ |
| 2 | PLX-C | 1 × 10$^6$ | 1 | C.G.25.0 | 10 ♂ |
| 3 | PLX-C | 1 × 10$^6$ | 2 | C.G.25.0 | 10 ♂ |
| 4 | PLX-C | 0.5 × 10$^6$ | 1 | C.G.13.0 | 10 ♂ |
| 5 | PLX-C | 0.1 × 10$^6$ | 1 | C.G.13.0 | 10 ♂ |
| 6 | Control Freezing Medium | N/A | 1 | N/A | 10 ♂ |
| 7* | PLX-C | 1 × 10$^6$ | 1 | C.G.13.0 C.G.25.0 | 10 ♂ |

In this study, different PLX-C batches at three concentrations were administered. The results showed that 0.1×10$^6$ and 0.5×10$^6$ PLX-C had a minor therapeutic benefit. A noticeable improvement in blood flow was observed by day 29 (end of experiment) in animals treated with 1×10$^6$. This improvement in blood flow was significant (p<0.05) in group 2M (batch G.C25) in comparison to control, vehicle injected mice. Additionally, a second injection of the same batch of cells significantly improved BF on day 15 compared to the single injection (55±24 compared to 31±12.9 and 27 f 12.5%, respectively). Macroscopic assessment of ischemic severity revealed that there was a trend for improvement in the groups receiving 1×10$^6$ (IM & 2M) in comparison to the control vehicle treated group (6M).

Altogether, these results demonstrate the efficacy of the adherent cells in inducing vascularization (e.g., blood flow) and improving limb function in hind limb ischemic mice model and suggest the use of these cells (e.g., placental derived adherent cells) for treating ischemic limb diseases.

Example 7

PLX-C for the Treatment of Stroke

The aim of this study was to evaluate the therapeutic efficacy of systemic (intravenous) human PLX-C—placenta derived adherent cells transplantation in the treatment of stroke.

Materials and Experimental Methods

Subjects, Surgery and Transplantation

Male spontaneously hypertensive rats, suffering from hypertension, hypercholesterolemia, diabetes and microangiopathies were used. The animals were kept under constant conditions concerning temperature, air humidity and light/dark cycle. Subjects were assigned experimental groups randomly (see Table 8, below).

TABLE 8

Rat treatment groups in the treatment of stroke

| Group no. | Treatment | No. of animals |
|---|---|---|
| 1 | PLX-C, batch 1 single administration | N = 8 |
| 2 | PLX-C, batch 1 double administration | N = 7 |
| 3 | PLX-C, batch 2 single administration | N = 8 |
| 4 | PLX-C, batch 2 double administration | N = 7 |
| 5 | Control - Vehicle solution | N = 12 |

Animals received a single or double dose of 1×10$^6$ PLX-C of different batches. All transplantation procedures were conducted intravenously. The double injected group was transplanted 10 and 24 hours following brain ischemia, while single transplantations were performed 24 hours upon stroke. All transplanted cells were pre-labeled with the fluorescence dye PKH26.

Experimental brain ischemia was conducted via permanent occlusion of the right cerebral artery. Of note, one animal died following anesthesia.

Magnetic Resonance Investigation (MRI)

MRI of lesion development was carried out on days 1, 8, 29 and 60 using a 1.5 T scanner (Philips). Infarct volumetry and brain atrophy was measured and calculated as means of values obtained by three blinded investigators using coronal T2-sequences.

Behavioral Tests

Functional changes were measured by using two dependent behavioral test arrays. The Beam Walk test is a common test used to quantify sensory-motor deficits. The rats were conditioned to run across a horizontal mounted bar with the rat's home cage at the end. The time of transit was measured for five times and documented as diurnal mean value. Hanging at the beam was assessed with 20 seconds and falling down with 30 seconds. Measurements took place daily within the first week and every seventh day until the end of the observation period.

The second test, the modified neurological severity score (mNSS) contained additional sensory, motor and reflex items. Outcome of the mNSS was expressed as a score between 1 and 18, whereas points between 1 and 6 implied a mild, 7 to 12 a moderate and 13 to 18 a sever injury. Evaluation of mNSS score was performed on days 1, 4, 7, 14, 21, 28, 35, 42, 49 and 56 following brain ischemia.

Histology

Subsequent to the end of the experimental period, all rats were sacrificed and transcardially perfused with 4% formalin solution. Extracted brains were cryopreserved and cut into 30 μm thick sections. For the appraisal of glia reaction, an immunohistochemical investigation was performed with primary antibody against GFAP. A 750 μm broad area was examined (semi-quantitatively) close to the infarct border for density of GFAP+ cells. For inspection of astroglial reactivity, 15 regions where included with average interspaces of 0.6 mm.

Statistics

All data concerning weight, MRI analysis and histological examinations were investigated for Gaussian distribution and analyzed for statistically significant differences using the ANOVA and accordingly the ANOVA on ranks.

Data collected in the Beam Walk and mNSS test were subjected to detailed statistical analysis making allowance for repeated measurements of subjects as well as for temporal development of subjects individually (stratified analysis). For balancing of inter-individual differences concerning the degree of brain damage a random intercept model was used. The data collected within the Beam Walk test therefore had to be transformed to a categorical system. Here, time values of less than 5 seconds were considered as category (0), 5 to 10 seconds as category (1), 10 to 15 seconds as category (2), 15 to 20 seconds as category (3), hanging as category (4) and falling as category (5).

Experimental Results

Weight

Periodic weighing allowed a good estimation of the subject's general state of health. An initial reduction of weight was observed in all groups due to anesthesia and the surgical intervention (data not shown). Subsequently, a quick normalization of weight and a stable course until the end of the experiment at day 60 was observed (data not shown). The experimental groups showed a homologous progression of body weight.

Beam Walk Test

All experimental groups showed a significant reduction of Beam Walk categories during the course of the experiment (data not shown). A significant lower decrease of Beam Walk categories were observed in the experimental group 1 (PLX-C batch 1 single administration) compared to the control group (−0.01247 vs. −0.02931, respectively). There was no evidence for statistically significant differences between the experimental group 3 (PLX-C batch 2 single administration) and the control group (data not shown).

Modified Neurological Severity Score (mNss)

All experimental groups displayed a significant reduction of neurological score points (data not shown). Comparing the mNSS results of subjects treated with PLX-2 (PLX-C double administration) revealed a statistically significant superiority compared to the control group. The duplicate transplantation of batch2 (group 3) showed a significant improvement in the mNSS test compared to the simple injection of the same batch (data not shown).

Infarct Volumetry

Magnetic resonance imaging is a highly sophisticated method to estimate the degree of brain damage and tissue lost in vivo. Taking inter-individual fluctuations into consideration, the development of infarct volume was denoted as percentage of the infarct volume at day 1, individually. The infarct volume on day 1 did not differ significantly between the experimental groups. The general development of infarct volume displayed an approximate decrease of 50% between day 1 and day 8. This was mainly due to a retrogression of the initial brain edema. Examination of lesion development in vivo using MRI revealed that group 4 (PLX-C batch 2 double administration) subjects showed a significant reduced infarct quotient at Day 60 (0.48±0.02 vs. 0.60±0.03, respectively, results not shown).

Taken together, these results indicate that intravascular administration of PLX-C resulted in a significant improvement of functional recovery in both behavioral tests in the treatment of stroke. Moreover, a considerable and as well statistically significant superiority of PLX-C double transplantations was observed compared to the analogous single injection.

A corroboration of measured behavioral improvements by MRI was evident in subjects treated twice with PLX-C. In addition, a significant reduction of the infarct volume and the brain atrophy was observed at the end of the experiment. Moreover, in both functional tests a stable improvement of functional recovery following double-dosed transplantation of PLX-C was observed compared to controls and unverifiable effects upon single injections.

Example 8

Treatment of Pathologies Requiring Connective Tissue Regeneration and/or Repair

Treating Pathologies Requiring Bone Regeneration and/or Repair Using the Adherent Cells of the Invention Animal models (e.g., Mature New Zealand white rabbits) are used to examine the effect of the adherent cells of the invention (which are derived from placenta or adipose tissue and are obtained from a 3D culture, e.g., PIX-C cells) on the healing of critical-sized segmental defects in the femora. The animals are randomly assigned to one of three groups. Animals of group A, are injected with $1\text{-}10\times10^6$ of the adherent cells (PLX-C cells) into the defect site. Animals of group B are injected with PBS. In animals of group C, the defect was left untreated. Radiographs are made immediately after the operation and at one-week intervals. At 12 weeks, the animals are sacrificed, the involved femora are removed, and undecalcified histological sections from the defects and adjacent bone are prepared. Mechanical, histological and histomorphometric studies are carried out to examine the healing of the defects and the formation of bone in and around the defected site. In addition a reverse transcription-polymerase chain reaction (RT-PCR) is performed to detect mRNA of type-I and type-II collagen.

Treating Pathologies Requiring Tendon Regeneration and/or Repair Using the Adherent Cells of the Invention Animal models (e.g., skeletally mature New Zealand white rabbits) are used to examine the effect of the adherent cells of the invention (e.g., PLX-C cells) on the healing of tendons. The hallucis longus tendons are translated into 2.5-mm diameter calcaneal bone tunnels. The bone tunnels are treated with or without PLX-C. The animals are randomly assigned to one of three groups. Animals of group A, are injected with $1\text{-}10 \times 10^6$ PLX-C cells into the defect site or IV. Animals of group B are injected with PBS. In, animals of group C the defect is left untreated. Three specimens from each group are harvested at 2, 4, and 6 weeks postoperatively and evaluation for morphologic characteristics of the healing tendon to bone interface is performed by the use of conventional histology and immunohistochemical localization of collagen Types I, II, and III.

Treating Pathologies Requiring Cartilage Regeneration and/or Repair Using the Adherent Cells of the Invention Animal models (e.g., skeletally mature New Zealand white rabbits) are used to examine the effect of the adherent cells of the invention (e.g., PLX-C cells) on the healing of cartilage. A full-thickness defect of the articular cartilage of the patellar groove of the left distal femur is performed. A flap of about 6 mm is removed from the fascia overlying the quadriceps muscle and sutured to the peripheral rim of the artificial defect with 6-0 catgut. The animals are randomly assigned to one of three groups. Animals of group A are injected with $1\text{-}10 \times 10^6$ PLX-C cells into the defect site or IV. Animals of group B are injected with PBS. In animals of group C, the defect is left untreated. The animals are sacrificed. Fourteen weeks after the implantation of the PLX-C cells onto the osteochondral defect, the distal femora are resected and histological evaluation are performed and the specimens are graded semiquantitatively based on the predominant nature of the repair tissue, matrix staining, regularity of the surface, structural integrity, thickness of the repair, apposition between the repaired cartilage and surrounding normal cartilage, freedom from degenerative signs in repair tissue, and freedom from degenerative changes of the surrounding normal cartilage.

Treating Pathologies Requiring Ligament Regeneration and/or Repair Using the Adherent Cells of the Invention Animal models (e.g., skeletally mature New Zealand white rabbits) are used to examine the effect of the adherent cells of the invention (e.g., PLX-C cells) on the healing of ligament. Unicortical circular defects of 8 mm in diameter will be performed. The animals are randomly assigned to one of three groups. Animals of group A are injected with $1\text{-}10 \times 10^6$ PLX-C cells into the defect site or IV. Animals of group B are injected with PBS. In animals of group C, the defect is left untreated. The animals are sacrificed fourteen weeks after the implantation of the PLX-C cells onto the oligamental defect. Histological evaluation are performed and the specimens are graded semiquantitatively based on the predominant nature of the repaired tissue.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the invention.

REFERENCES

Additional References are Cited in Text

Bauer, Thomas W., Muschler, George F., Bone Graft Materials: An Overview of the Basic Science. Clinical Orthopaedics & Related Research. 371:10-27, February 2000.

Carstanjen B, Desbois C., Hekmati M, and Behr L. Successful engraftment of cultured autologous mesenchymal stem cells in a surgically repaired soft palate defect in an adult horse. Can J Vet Res. 2006 April; 70(2): 143-147.

Bruder S P, et al. 1998 The effect of implants loaded with autologous mesenchymal stem cells on the healing of canine segmental bone defects. J Bone Joint Surg Am. 80(7):985-96

Chao Wan, Qiling He, Gang Li, 2006. Allogenic peripheral blood derived mesenchymal stem cells (MSCs) enhance bone regeneration in rabbit ulna critical-sized bone defect model. Journal of Orthopaedic Research 24 (4) 610-618.

Herthel D. J. 2001, Enhanced Suspensory Ligament Healing in 100 Horses by Stem Cells and Other Bone Marrow Components. AAEP PROCEEDINGS/Vol. 47.

Gordon et al., Tendon Regeneration Using Mesenchymal Stem Cells. p 313-320 in Tendon Injuries. Springer London. 2005.

Horwitz et al., 1999. Transplantability and therapeutic effects of bone marrow derived mesenchymal cells in children with osteogenesis imperfecta. Nat. Med. 5:309-313.

Horwitz et al., 2002. Isolated allogeneic bone marrow-derived mesenchymal cells engraft and stimulate growth in children with osteogenesis imperfecta: Implications for cell therapy of bone. PNAS 99(13)8932-8937.

Livingston, T. L. 2003 Mesenchymal stem cells combined with biphasic calcium phosphate ceramics promote bone regeneration. Journal of Materials Science: Volume 14 (3):211-218.

Young et al. 1998. Use of mesenchymal stem cells in a collagen matrix for Achilles tendon repair. J Orthop Res. 16(4):406-13.

What is claimed is:

1. A method of treating a wound in a subject in need thereof, comprising systemically administering to the subject a therapeutically effective amount of undifferentiated placenta-derived adherent stromal cells in a liquid suspension, wherein the adherent stromal cells do not express CD34, thereby treating the wound.

2. The method of claim 1, wherein at least 10% of said cells are at a proliferative phase.

3. The method of claim 1, wherein the wound is a wound to the skin.

4. The method of claim 1, wherein said cells have been propagated in three-dimensional (3D) culturing conditions.

5. The method of claim 4, wherein said three-dimensional (3D) culturing conditions comprise a 3D bioreactor.

6. The method of claim 4, wherein said three-dimensional (3D) culturing conditions are effected under perfusion.

7. The method of claim 4, wherein said three-dimensional (3D) culturing conditions comprise an adherent material selected from the group consisting of a polystyrene, a polyester, and a polypropylene.

8. The method of claim 1, wherein said cells have been cultured for at least 3 days.

9. The method of claim 1, wherein said cells have been cultured until at least 10% of said cells are proliferating.

10. The method of claim 4, wherein said cells express a marker selected from the group consisting of CD73, CD90, CD29 and CD105.

11. The method of claim 4, wherein said cells do not express a marker selected from the group consisting of CD3, CD4, CD45, CD80, HLA-DR, CD11b, CD14, CD19 and CD79.

12. The method of claim 6, wherein said perfusion rate is adjusted in order to maintain a constant glucose concentration in the culture medium.

13. The method of claim 12, wherein said constant glucose concentration is about 550 mg/L.

14. The method of claim 1, wherein said cells have been propagated in two-dimensional (2D) culturing conditions.

15. The method of claim 14, wherein said cells express a marker selected from the group consisting of CD90, CD105, CD73 and CD29.

16. The method of claim 1, wherein treating the wound comprises treating delayed wound healing.

17. The method of claim 16, wherein the wound is an ulcer.

18. The method of claim 17, wherein the ulcer wound is to the skin.

19. The method of claim 3, wherein the wound to the skin is an ulcer.

20. The method of claim 1, wherein the undifferentiated placenta-derived adherent stromal cells are non-autologous to the subject.

21. A method of preparing cells for treating a wound in a subject in need thereof, the method comprising expanding placenta-derived adherent stromal cells in culture, wherein when the culture-expanded placenta-derived adherent stromal cells are subsequently systemically administered in a liquid suspension to a subject in a therapeutically effective amount they treat a wound in the subject.

22. The method of claim 21, wherein the culture is a 3D culture.

23. The method of claim 22, wherein said placenta-derived adherent stromal cells are non-autologous to the subject.

24. A method of preparing cells for treating a wound in a subject in need thereof, the method comprising expanding non-autologous placenta-derived adherent stromal cells in three-dimensional culture, wherein when the culture-expanded placenta-derived adherent stromal cells are subsequently systemically administered in a liquid suspension to the subject in a therapeutically effective amount they treat a wound in the subject.

* * * * *